(12) United States Patent
Mamet

(10) Patent No.: US 10,041,069 B2
(45) Date of Patent: Aug. 7, 2018

(54) GENE EXPRESSION AND PAIN

(71) Applicant: Adynxx, Inc., San Francisco, CA (US)

(72) Inventor: Julien Mamet, San Francisco, CA (US)

(73) Assignee: Adynxx, Inc., San Francisco, CA (US)

( * ) Notice: Subject to any disclaimer, the term of this patent is extended or adjusted under 35 U.S.C. 154(b) by 0 days.

(21) Appl. No.: 15/019,791

(22) Filed: Feb. 9, 2016

(65) Prior Publication Data

US 2016/0222382 A1 Aug. 4, 2016

Related U.S. Application Data

(63) Continuation of application No. 14/258,927, filed on Apr. 22, 2014, now Pat. No. 9,290,762, which is a continuation of application No. 13/316,321, filed on Dec. 9, 2011, now Pat. No. 8,741,864, which is a continuation of application No. 13/048,793, filed on Mar. 15, 2011, now Pat. No. 8,093,225, which is a continuation of application No. 12/119,435, filed on May 12, 2008, now Pat. No. 7,943,591.

(60) Provisional application No. 60/917,583, filed on May 11, 2007.

(51) Int. Cl.
*C12N 15/113* (2010.01)
*C07H 21/04* (2006.01)

(52) U.S. Cl.
CPC ........... *C12N 15/113* (2013.01); *C07H 21/04* (2013.01); *C12N 2310/13* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 5,206,152 A | 4/1993 | Sukhatme |
| 5,504,075 A | 4/1996 | Burrows et al. |
| 5,683,985 A | 11/1997 | Chu et al. |
| 6,004,813 A | 12/1999 | Serlupi-Crescenzi et al. |
| 6,008,048 A | 12/1999 | Monia et al. |
| 6,011,143 A | 1/2000 | Shionoya et al. |
| 6,022,863 A | 2/2000 | Peyman |
| 6,034,234 A | 3/2000 | Matsuo |
| 6,060,310 A | 5/2000 | Cho-Chung |
| 6,140,128 A | 10/2000 | Cohen et al. |
| 6,262,033 B1 | 7/2001 | Morishita et al. |
| 6,270,761 B1 | 8/2001 | Russell et al. |
| 6,316,190 B1 | 11/2001 | Rein et al. |
| 6,333,408 B1 | 12/2001 | Motojima et al. |
| 6,395,029 B1 | 5/2002 | Levy |
| 6,410,516 B1 | 6/2002 | Baltimore et al. |
| 6,410,721 B1 | 6/2002 | Hunt et al. |
| 6,432,641 B1 | 8/2002 | Lee et al. |
| 6,555,525 B2 | 4/2003 | Burke |
| 6,599,741 B1 | 7/2003 | Hecker et al. |
| 6,774,118 B1 | 8/2004 | Dzau et al. |
| 6,818,626 B1 | 11/2004 | Wolff et al. |
| 6,821,956 B2 | 11/2004 | Dzau et al. |
| 6,867,289 B1 | 3/2005 | Gorenstein et al. |
| 6,890,909 B1 | 5/2005 | Ono et al. |
| 6,927,027 B2 | 8/2005 | Erikson et al. |
| 6,969,704 B1 | 11/2005 | Pinsky et al. |
| 7,014,861 B2 | 3/2006 | Roorda et al. |
| 7,060,690 B2 | 6/2006 | Klem |
| 7,108,844 B2 | 9/2006 | Carpentier |
| 7,160,869 B2 | 1/2007 | Lee et al. |
| 7,186,556 B2 | 3/2007 | Hecker et al. |
| 7,256,182 B2 | 8/2007 | Lawrence, III et al. |
| 7,320,964 B2 | 1/2008 | Hecker et al. |
| 7,482,158 B2 | 1/2009 | Mathison |
| 7,524,949 B2 | 4/2009 | Hecker et al. |
| 7,585,848 B2 | 9/2009 | Masuda et al. |
| 7,777,014 B2 | 8/2010 | Cattaruzza et al. |
| 7,943,591 B2 | 5/2011 | Mamet |
| 8,093,225 B2 | 1/2012 | Mamet |
| 8,741,864 B2 | 6/2014 | Mamet |
| 8,808,747 B2 | 8/2014 | Brown et al. |
| 9,290,762 B2 | 3/2016 | Mamet |
| 9,700,624 B2 | 7/2017 | Mamet et al. |
| 2002/0192184 A1 | 12/2002 | Carpentier et al. |
| 2003/0166555 A1 | 9/2003 | Alberini et al. |
| 2004/0048820 A1 | 3/2004 | Hecker et al. |
| 2004/0192598 A1 | 9/2004 | Kragie |
| 2004/0229833 A1 | 11/2004 | Dzau et al. |
| 2005/0192238 A1 | 9/2005 | Hecker et al. |
| 2006/0069055 A1 | 3/2006 | Dajee et al. |
| 2006/0116344 A1 | 6/2006 | Morishita et al. |
| 2006/0122134 A1 | 6/2006 | Cattaruzza et al. |
| 2006/0153847 A1 | 7/2006 | Masuda |
| 2006/0154886 A1 | 7/2006 | Weihe et al. |
| 2006/0166916 A1 | 7/2006 | Mathison |
| 2006/0189564 A1 | 8/2006 | Burright et al. |
| 2006/0293264 A1 | 12/2006 | Grandis et al. |
| 2008/0300209 A1 | 12/2008 | Mamet |
| 2010/0305492 A1 | 12/2010 | Lad et al. |
| 2011/0166212 A1 | 7/2011 | Mamet |
| 2012/0046348 A1 | 2/2012 | Valliant et al. |
| 2012/0232131 A1 | 9/2012 | Mamet |
| 2013/0309201 A1 | 11/2013 | Bazinet et al. |
| 2014/0221490 A1 | 8/2014 | Lacouture et al. |
| 2014/0343132 A1 | 11/2014 | Mamet |
| 2015/0111956 A1 | 4/2015 | Mamet et al. |
| 2017/0247694 A1 | 8/2017 | Mamet et al. |

(Continued)

FOREIGN PATENT DOCUMENTS

CA 2583576 4/2006
EP 0572287 A2 12/1993

(Continued)

OTHER PUBLICATIONS

Kajimura et al.,Gene (Feb. 2007) 388(1-2)34-42.*

(Continued)

*Primary Examiner* — James D Schultz
(74) *Attorney, Agent, or Firm* — Cooley LLP

(57) ABSTRACT

The present invention relates to double-stranded oligonucleotides, pharmaceutical compositions thereof, and use of such double-stranded oligonucleotides and pharmaceutical compositions to modulate nociceptive signaling in a cell or prevent and/or treat pain in a patient.

11 Claims, 8 Drawing Sheets

(56) References Cited

FOREIGN PATENT DOCUMENTS

| | | |
|---|---|---|
| EP | 1281763 A2 | 2/2003 |
| EP | 1298141 A1 | 4/2003 |
| EP | 1357184 A2 | 10/2003 |
| EP | 1690544 A2 | 8/2006 |
| JP | 2005-336081 A | 12/2005 |
| JP | 2010-526541 A | 9/2013 |
| JP | 2013-536195 A | 9/2013 |
| KR | 2005-0016361 A | 2/2005 |
| WO | WO 1996/029433 A1 | 9/1996 |
| WO | WO 1999/026634 A1 | 6/1999 |
| WO | WO 2002/029044 A2 | 4/2002 |
| WO | WO 2002/041922 A1 | 5/2002 |
| WO | WO 2002/066071 A2 | 8/2002 |
| WO | WO 2002/070668 A2 | 9/2002 |
| WO | WO 2003/063799 A2 | 8/2003 |
| WO | WO 2003/091432 A1 | 11/2003 |
| WO | WO 2004/052401 A2 | 5/2004 |
| WO | WO 2005/004702 A2 | 1/2005 |
| WO | WO 2005/027830 A2 | 3/2005 |
| WO | WO 2006/035434 A2 | 4/2006 |
| WO | WO 2006/043722 A1 | 4/2006 |
| WO | WO 2006/086105 A2 | 8/2006 |
| WO | WO 2006/096498 A2 | 9/2006 |
| WO | WO 2008/141308 A2 | 11/2008 |
| WO | WO 2012/021985 A1 | 2/2012 |
| WO | WO 2012/177906 A1 | 12/2012 |
| WO | WO 2013/170086 A2 | 11/2013 |
| WO | WO 2016/025829 A1 | 2/2016 |
| WO | WO 2017/151644 A1 | 9/2017 |

OTHER PUBLICATIONS

Lei et al., Development, (2001) 128:1147-1158.*
van Vliet et al., Genomics 87 (2006) 474-482.*
Matsumoto, Nobukyuki, et al. "Cloning the cDNA for a new human zinc finger protein defines a group of closely related Krüppel-like transcription factors." Journal of Biological Chemistry (1998); 273.43: 28229-28237.
Shields, Janiel M., and Yang, Vincent W. "Identification of the DNA sequence that interacts with the gut-enriched Krüppel-like factor." Nucleic Acids Research (1998); 26.3: 796-802.
Dobi, A., and Agoston, D. V. "Submillimolar levels of calcium regulates DNA structure at the dinucleotide repeat (TG/AC) n." Proceedings of the National Academy of Sciences (1998); 95.11: 5981-5986.
European Search Report, European Patent Application No. 13787024.2, dated Apr. 13, 2017 [dated Apr. 21, 2017], 8 pages.
International Preliminary Report on Patentability, International Application No. PCT/US2015/045268, dated Feb. 21, 2017, 12 pages.
Altschul et al., "Blast Help Manual", Nall. Cent. Biotechnol. Inf., Nall. Library Medicine, 9 pages. [downloaded May 5, 2015] http://dir.nhlbi.nih.gov/papers/lkem/imcd/docs/Help.aspx?blast_help.html.
Altschul et al., "Gapped BLAST and PSI-BLAST: a new generation of protein database search programs", Nucelic Acid Research, 1997, pp. 3389-3402, vol. 25, No. 17.
Australian Application No. 2014201462, Examination Report dated Sep. 4, 2015, 4 pages.
Australian Application No. 2014201462, Examination Report dated Jun. 30, 2016, 3 pages.
Canadian Application No. 2,723,672, Office Action dated Nov. 30, 2015, 4 pages.
Daftary, Gaurang S., et al. "A novel role of the Sp/KLF transcription factor KLF11 in arresting progression of endometriosis." PloS One (2013); 8.3: e60165.
Enomoto, Takashi, et al. "Transcriptional regulation of an insulin-sensitizing adipokine adipolin/CTRP12 in adipocytes by Kruppel-like factor 15." PloS One (2013); 8.12: e83183.

Dzau, Victor J., "Transcription Factor Decoy," Circulation Research, 2002, vol. 90, pp. 1234-1236.
European Application No. 14179247.3, Supplementary European Search Report dated Dec. 3, 2014, 7 pages.
European Search Report, European Patent Application No. 13787024, dated Dec. 8, 2015, 9 pages.
Hasan and MacDonald, "Sp/Kruppel-like transcription factors are essential for the expression of mitochondrial glycerol phosphate dehydrogenase promoter B," Gene, 296(1-2):221-234 (2002).
International Preliminary Report on Patentability, International Application No. PCT/US2008/063471, dated Nov. 17, 2009, 6 pages.
International Preliminary Report on Patentability for PCT Application No. PCT/US2013/040426 dated Nov. 11, 2014 (7 pages).
Written Opinion for PCT Application No. PCT/US2013/040426 dated Nov. 26, 2013 (6 pages).
International Search Report for PCT Application No. PCT/US2013/040426 dated Jan. 20, 2014 (5 pages).
International Search Report and Written Opinion, International Application No. PCT/US2015/045268, dated Oct. 28, 2015, 16 pages.
Lei, Lei, et al. "The zinc finger transcription factor Klf7 is required for TrkA gene expression and development of nociceptive sensory neurons." Genes & development 19.11 (2005): 1354-1364.
Office Action, Japanese Application No. 201380036825.2, dated Jan. 15, 2016, 5 pages.
Search Report, Japanese Application No. 201380036825.2, dated Jan. 7, 2016, 5 page.
Xu, Yisheng et al., "Multimerization and Aggregation of Native-State Insulin: Effect of Zinc," Langmuir, Jan. 10, J012, pp. 579-586, vol. 28, No. 1.
Ahn et al., "Inhibitory effects of novel AP-1 decoy oligodeoxynucleotides on vascular smooth muscle cell proliferation in vitro and neointimal formation in vivo", Circ Res, 90:1325-1332 (2002).
Australian Application No. 2008251320, Examination Report dated Sep. 4, 2012.
Borner et al., State transcription factor binding sites with mismatches within the canonicai 5'-TTC . . . GAA-3' motif involved in regulation of delta- and mu-opioid receptors, J Neurochem, 91[6]:1493-1500 (2004).
Buchwald et al., "Decoy oligodeoxynucleotide against activator protein-1 reduces neointimal proliferation after coronary angioplasty in hypercholesterolemic minipigs", JACC, 39:732-738 (2002).
Cattaruzza et al., "Mechanosensitive transcription factors involved in endothelin B receptor expression", J Biol. Chem, 276[40]:36999-37003 (2001).
Chen et al., "Up-regulation of Egr1 by 1.25-dihydroxyvitamin D3 contributes to increased expression of p35 activator of cyclin-dependent kinase 5 and consequent onset of the terminal phase of HL60 cell differentiation", Cancer Res, 64[15]:5425-5433 (2004).
Cho et al., "A genomic-scale view of the cAMP response element-enhancer decoy: a tumor target based genetic tool", PNAS, 99[24]:15626-15631 (2002).
Cho et al., "Potentiation of lipopolysaccharide-inducible cyclooxygenase 2 expression by C2-ceramide via c-Jun N-terminal kinase-mediated activation of CCAAT/enhancer binding protein in macrophages", Mol Pharmacol, 63[3]:512-523 (2003).
D'Acquisto et al., "Local administration of transcription factor decoy oligonucleotides to nuclear factor-kB prevents carrageenin-induced inflammation in rat hind paw", Gene Ther, 7[20]:1731-1737 (2000).
Dash et al., "Sequestration of serum response factor in the hippocampus impairs long-term spatial memory", J Neuroch, 93:269-278 (2005).
European Application No. 08755344.2, Extended European Search Report dated Oct. 11, 2012, 9 pages.
Foti et al., "A nucleoprotein complex containing Sp1, C/EBPbeta, and HMGI-Y controls human insulin receptor gene transcription", Mol Cell Biol, 23[8]:2720-2732 (2003).

(56) References Cited

OTHER PUBLICATIONS

Gao et al., "A single decoy oligodeoxynucleotides targeting multiple oncoproteins produces strong anticancer effects", *Mol Pharmacal*, 70[5]:1621-1629 (2006).
Grote et al., "Stech-inducible expession of the angogenic facor CCN1 in vasular smooth muscle cells is mediated by Egr-1", *J Biol Chem.*, 279[53]:55675-555681 (2004).
Gupta, A.K. et al., "USF-1 and USF-2 trans-repress IL-1beta-induced iNOS transcription in mesangial cells", *Am J Physical Cell Physiol*, 283:C1065-1072 (2002).
Herdegen, T. et al., "Inducible and constitutive transcription factors in the mammalian nervous system: control of gene expression by Jun, Fos and Krox, and CREB/ATF proteins", *Brain Res Brain Res Rev.*, 28[3]:370-490 (1998).
Igwe, O.J., "Modulation of peripheral inflammation in sensory ganglia by nuclear factor kB decoy oligodeoxynucleotide: involvement of SRC kinase pathway", *Neurosci Lett.*, 381[1-2]:114-119 (2005).
Ishibashi et al., "Sp1 decoy transfected to carcinoma cells suppresses the expression of vascular endothelial growth factor, transforming growth factor b1, and tissue factor and also cell growth and invasion activities", *Cancer Res.*, 60:6531-6536 (2000).
International Search Report and Written Opinion, International Application No. PCT/US2008/063471, dated Jan. 14, 2009.
Japanese Application No. 2010-507728, Office Action dated Feb. 1, 2013.
Kamimura et al., "Platelet-derived growth factor induces tissue factor expression in vascular smooth muscle cells via activation of Egr-1", *Hypertension*, 44[6]:944-951 (2004).
Kelkenberg et al., "CCAAT/enhancer-binding protein decoy oligodeoxynucleotide inhibition of macrophage-rich vascular lesion formation in hypercholesterolemic rabbits", *Arterioscler Thromb Vase Biol.*, 22:949-954 (2004).
Ko, S.W. et al., "Selective Contribution of Egr1 (Zif/268) to Persistent Inflammatory Pain", *Journal of Pain*, 6[1]:12-20 (2005).
Kohlstedt, K. et al., "Signaling via the angiotensin-converting enzyme enhances the expression of cyclooxygenase-2 in endothelial cells", *Hypertension*, 45:126-132 (2005).
Kraus et al., "The role of nuclear factor kappaB in tumor necrosis factor-regulated transcription of the human mu-opioid receptor gene", *Mol Pharmacol*, 64[4]:876-884 (2003).
Lee et al., "Spinal NFKB activation induces COX2 upregulation and contributes to inflammatory pain hypersensitivity", *Eur J Neurosci*, 19:3375-3381 (2004).
Leong et al., "Targeted inhibition of Stat3 with a decoy oligonucleotide abrogates head and neck cancer cell growth", *PNAS*, 100[7]:4138-4143 (2003).
Lesniak et al., "Binding and functional characteristics of two E-box motifs within the S1OOA6 (calcyclin) gene promoter", *J Cell Biochem*, 97[5]:1017-1024 (2006).
Lim et al., "Sequence-independent inhibition of RNA transcription by DNA dumbbells and other decoys", *Nucl Acids Res.*, 25[3]:575-581 (1997).
Ma et al., "Intrathecal injection of cAMP response element binding protein (CREB) antisense oligonucloetide attenuates tactile allodynia caused by partial sciatic nerve ligation", *Brain Research*, 988:97-104 (2003).
Mann et al., "Ex-vivo gene therapy of human vascular bypass grafts with E2F decoy: the PREVENT single-centre randomised controlled trial", *The Lancet*, 354:1493-1498 (1999).
Morishita et al., "A gene therapy strategy using a transcription factor decoy of the E2F binding site inhibits smooth muscle proliferation in vivo", *PNAS*, 92:5855-5859 (1995).
Motojima et al., "Sp1-like activity mediates angotensin-II-induced plasminogen-activator inhibitor type-1 (PAI-1) gene expression in mesangial cells", *Biochem J.*, 349:435-441 (2000).
Ohtani et al., "Inhibition of neointimal hyperplasia after balloon injury by cis-element 'decoy' of early growth response gene-1 in hypercholesterolemic rabbits", *Gene Ther*, 11[2]:126-132 (2004).

Park et al., "Dual blockade of cyclic AMP response element—(CRE) and AP-1-directed transcription by CRE-transcription factor decoy oligonucleotide gene-specific inhibition of tumor growth", *J Biol Chem.*, 274[3]:1573-1580 (1999).
Rygh et al., "Local and descending circuits regulate long-term potentiation and zif268 expression in spinal neurons", *Eur J Neuroscience*, 24[3]:761-772 (2006).
Sahin et al., "Inactivation of Ets 1 transcription factor by a specific decoy strategy reduces rat C6 glioma cell proliferation and mmp-9 expression", *Int J Mol Med*, 15:771-776 (2005).
Sakaue, G. et al, "NF-kB decoy supresses cytokine expression and thermal hyperalgesia in a rat neuropathic pain model", *NeuroReport*, 12[10]:2079-2084 (2001).
Sassa, Y. et al., "Functional role of Egr-1 mediating VEGF-induced tissue factor expression in the retinal capillary endothelium", *Graefes Arch Clin Exp Ophthalmol*, 240[12]:1003-1010 (2002).
Steiger et al., "cAMP response element-binding protein, activating transcription factor-4, and upstream stimulatory factor differentially control hippocampal $GABA_BR1a$ and $GABA_BR1b$ subunit gene expression through alternative promoters", *J Neurosci*, 24[27]:6115-6126 (2004).
Sun, T. et al., "Alleviation of neuropathic pain by intrathecal injection of antisense oligonucleotides to p65 subunit of NF-kappa B", *British Journal of Anaesthesia*, 97(4):553-558 (2006).
Suzuki et al., "Initial clinical cases of the use of a NF-kB decoy at the site of coronary stenting for the prevention of restenosis", *Circ Journal*, 68:270-271 (2004).
Swirnoff et al., "DNA-Binding Specificity of NGFI-A and Related Zinc Finger Transcription Factors", *Molecular and Cellular Biology*, 15[4]:2275-2287 (1995).
Taimor et al., "Transcription activator protein 1 (AP-1) mediates alpha- but not beta-adrenergic hypertrophic growth responses in adult cardiomyocytes", *Am J Physiol Heart Circ Physiol*, 286[6]:H2369-H2375 (2004).
Tanaka et al., "Sequence-specific interaction of alpha-beta-anomeric double stranded DNA with the p50 subunit of NFKB: application to the decoy approach", *Nucl Acids Res*, 22[15]:3069-3074 (1994).
Uchida et al., "Ceramide reduction and transcriptional up-regulation of glucosylceramide synthase through doxorubicin-activated Sp1 in drug-resistant HL-60/ADR cells", *Cancer Res*, 64:6271-6279 (2004).
Verrecchia et al., "Blocking Sp1 transcription factor broadly inhibits extracellular matrix gene expression in vitro and in vivo: implications for the treatment of tissue fibrosis", *J Invest Dermatol*, 116[5]:755-763 (2001).
Viedt et al., "The terminal complement complex C5b-9 stimulates interleukin-6 production in human smooth muscle cells through activation of transcription factors NF-kB and AP-1", *FASEB J*, 14:2370-2372 (2000).
Wagner et al., "Decoy Oligodeoxoynucleotide characterization of transcription factors controlling endothelin-B receptor expression in vascular smooth muscle cells", *Mol Pharmacol*, 58[6]:1333-1340 (2000).
Wang et al., "Dose-related antiallodynic effects of cyclic AMP response element-binding protein-antisense oligonucleotide in the spared nerve injury model of neuropathic pain", *Neuroscience*, 139[3]:1083-1093 (2006).
Xiang et al., "Egr-1 mediates SiO(2-driven transcription of membrane type I matrix metalloproteinase in macrophages", *J Huazhong Univ Sci Technolog Med Sci*, 27[1]:13-16 (2007).
Yang et al., "Thrombospondin-1 mediates distal tubule hypertrophy induced by glycated albumin", *Biochem J*, 379:89-97 (2004).
Zanetti et al., "Inhibition of Sp1 activity by a decoy PNA-DNA chimera prevents urokinase receptor expression and migration of breast cancer cells", *Biochem Pharmacol.*, 70[9]:1277-1287 (2005).
Zhang, P. et al., "Egr-1 mediates hypoxia-inducible transcription of the NORG1 gene through an overlapping Egr-1/Sp1 binding site in the promoter", *Cancer Research*, 67(19):9125-9133 (2007).
Database EMBL [Online] Jul. 14, 2005 (Jul. 14, 2005), "EST1078622 Normalized pine embryo library, Lib_D Pinus taeda cDNA clone PWAC753 3-end, mRNA sequence.", XP002769924, retrieved from EBI Accession No. EM_EST:DR688537, 2 pages.

(56) References Cited

OTHER PUBLICATIONS

Engleman and Marsala, "Efficacy of adding clonidine to intrathecal morphine in acute postoperative pain: meta-analysis." Br J Anaesth. (2013); 110(1): 21-27. Epub Sep. 21, 2012.
European Application No. EP 16199871.1, Extended European Search Report dated May 19, 2017, 9 pages.
International Search Report and Written Opinion, International Application No. PCT/US2017/019989, dated Jul. 19, 2017, 23 pages.
Mamet, J., et al., "Single intrathecal administration of the transcription factor decoy AYX1 prevents acute and chronic pain after incisional, inflammatory, or neuropathic injury." Pain (2013); 155(2): 322-333.
Szpara, M.L., et al., "Analysis of gene expression during neurite outgrowth and regeneration." BMC Neurosci. (2007); 8: 100, 17 pages.
Todorovic, et al., "T-type voltage-gated calcium channels as targets for the development of novel pain therapies." Br J Pharmacol. (2011); 163(3): 484-495.

\* cited by examiner

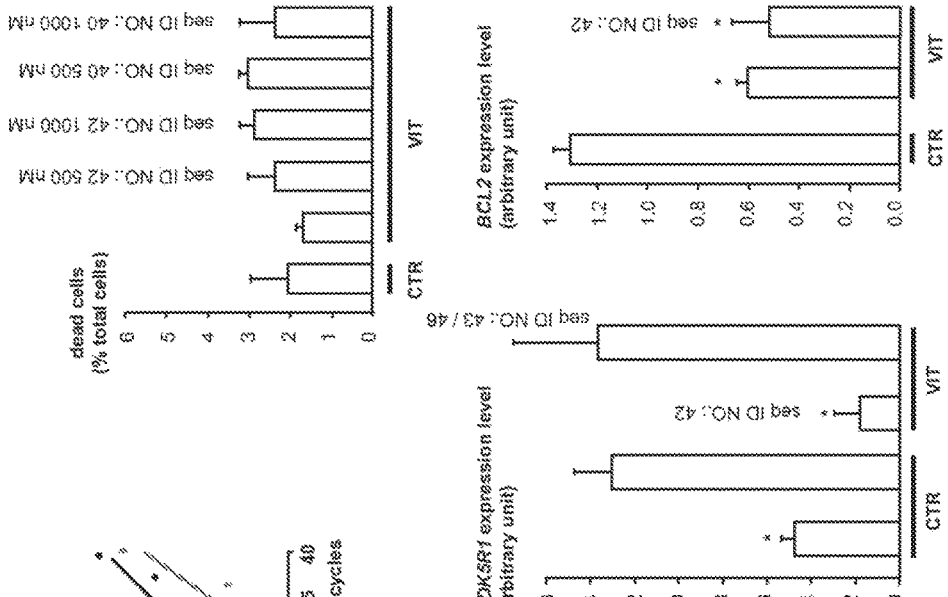
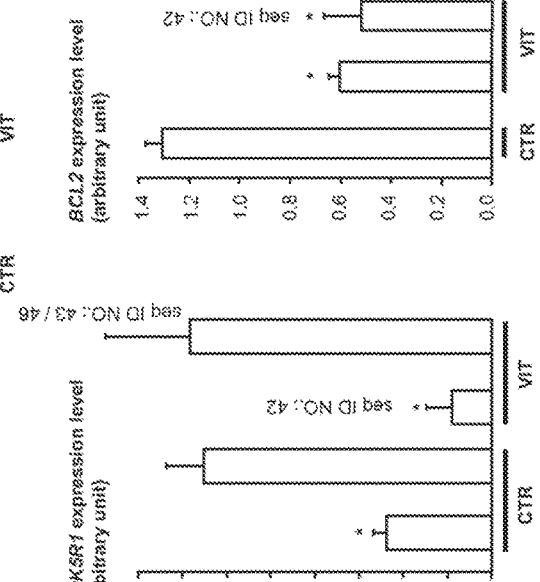
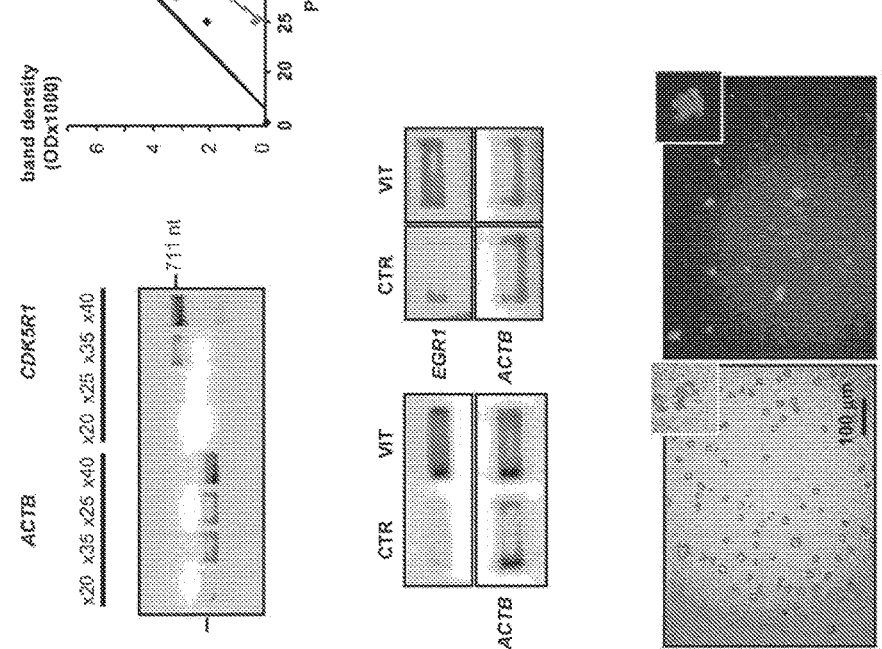
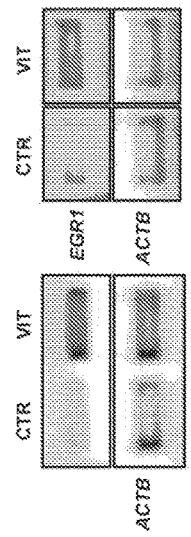
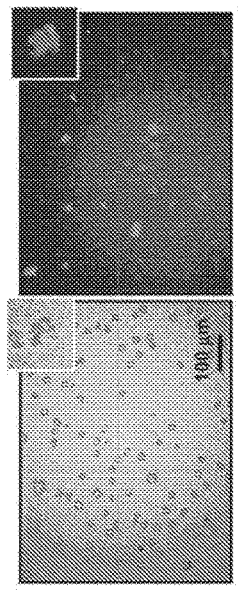

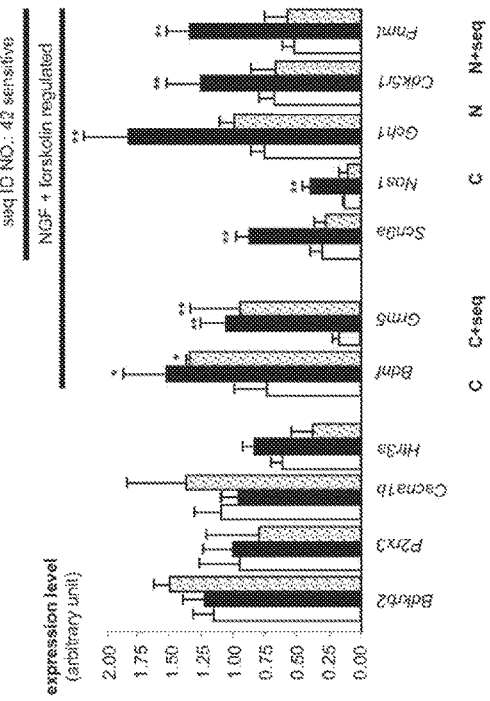
FIG. 5A
FIG. 5C
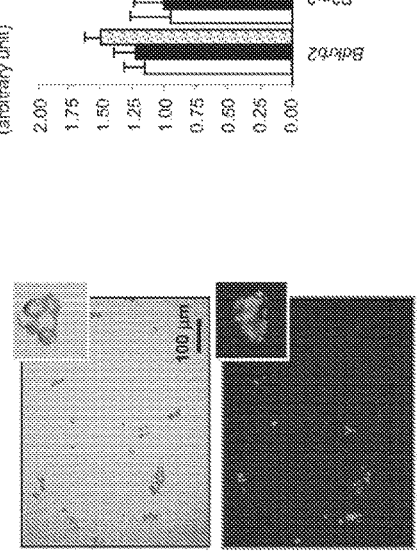
FIG. 5B
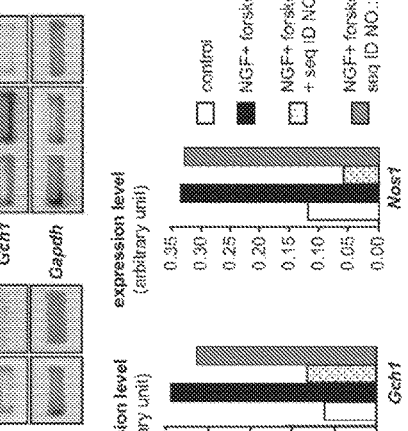
FIG. 5D
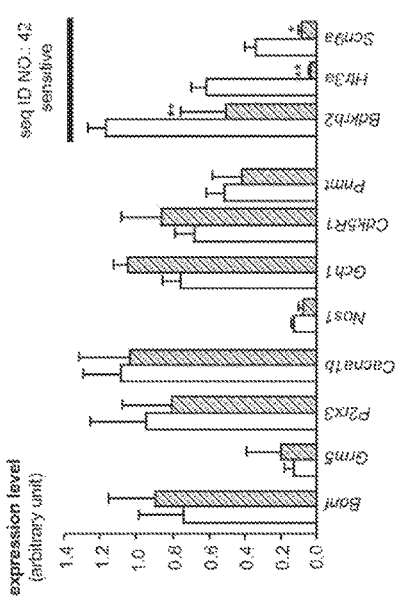
FIG. 5E

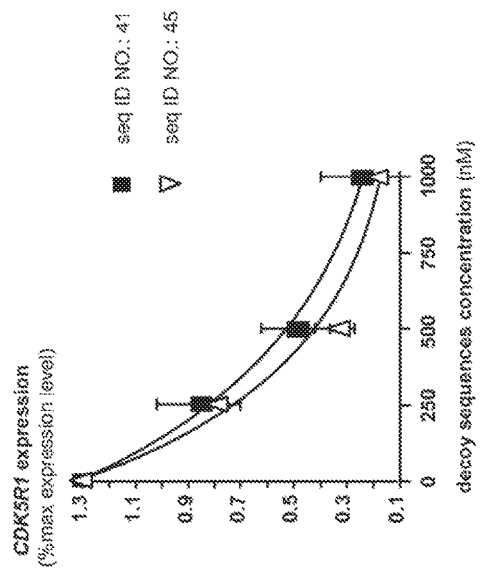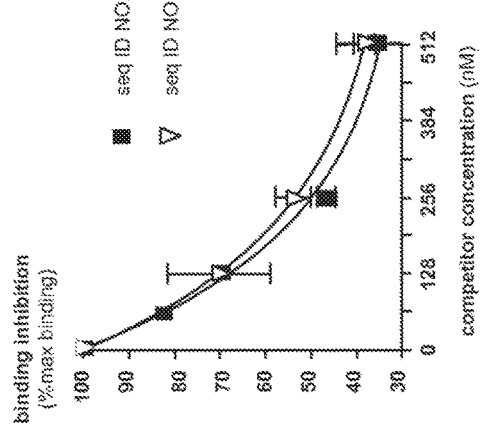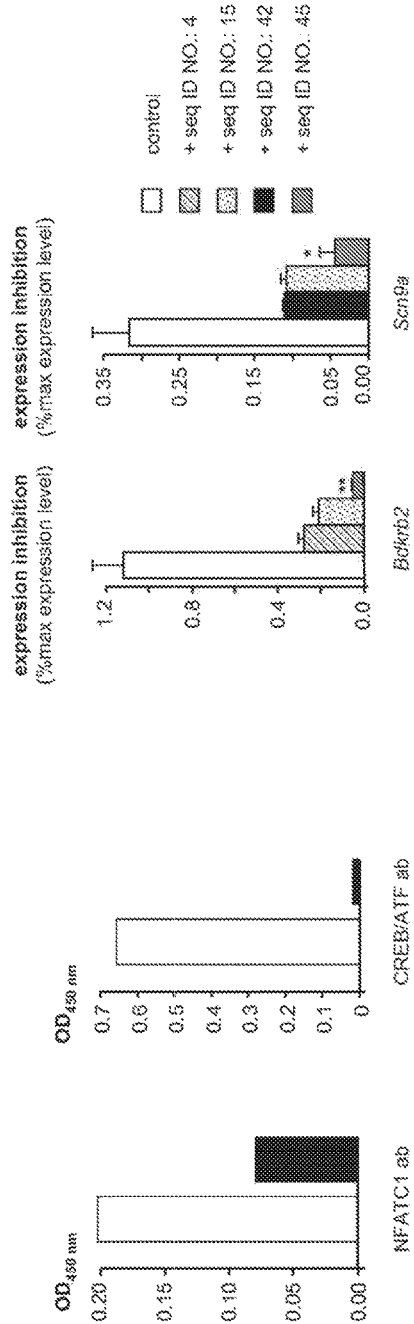
FIG. 7A
FIG. 7B
FIG. 7C
FIG. 7D

GENE EXPRESSION AND PAIN

CROSS-REFERENCE TO RELATED APPLICATIONS

The present application is a Continuation of U.S. patent application Ser. No. 14/258,927, filed Apr. 22, 2014; which is a Continuation of U.S. patent application Ser. No. 13/316,321, filed Dec. 9, 2011, now U.S. Pat. No. 8,741,864, issued Jun. 3, 2014; which is a Continuation of U.S. patent application Ser. No. 13/048,793, filed Mar. 15, 2011, now U.S. Pat. No. 8,093,225, issued Jan. 10, 2012, which is a Continuation of U.S. patent application Ser. No. 12/119,435, filed May 12, 2008, now U.S. Pat. No. 7,943,591 issued May 17, 2011, which claims priority to U.S. Provisional Application No. 60/917,583, filed May 11, 2007, all of which are incorporated by reference herein in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ADDY_001_05US_ST25.txt. The text file is 35 KB, was created on Feb. 8, 2016, and is being submitted electronically via EFS-Web.

TECHNICAL FIELD

The present invention relates to double-stranded nucleic acids, termed oligonucleotide decoys, pharmaceutical compositions thereof, and the use of such oligonucleotide decoys and pharmaceutical compositions to modulate nociceptive signaling and to prevent and/or treat pain.

BACKGROUND OF THE INVENTION

Pain may be defined as an unpleasant sensory and emotional experience associated with actual or potential tissue damage, or described in terms of such damage. Chronic pain afflicts 40% of the U.S. population and is associated with numerous deleterious medical conditions. Persistent and highly debilitating, chronic pain is generally accompanied by weakness, sleeplessness, a lack of appetite, irritability and depression. Over time, the quality of life is profoundly affected and patients are often incapable of accomplishing the simple tasks of everyday life.

Currently used pain treatments apply a three-step pain ladder which recommends the administration of drugs as follows: non-opioids (e.g., aspirin, acetaminophen, etc.), then, as necessary, mild opioids (e.g., codeine) and finally strong opioids (e.g., morphine). Despite this arsenal of drugs, over 50% of patients with chronic pain are not effectively treated.

The ineffectiveness of current pain treatments is, inter alia, due to significant toxicity issues with existing drug therapies. Mild to severe toxicity is induced by all classes of pain drugs: non steroidal inflammatory drugs cause gastrointestinal damage, coxibs are associated with heart failure, and opioids are responsible for numerous side effects including respiratory depression, sedation, digestive malfunctions and addiction.

Transcription factors are important factors in multiple signaling pathways and frequently control the concurrent expression of numerous genes. Many transcription factors are involved in the regulation of the expression of genes that are involved in pain including, but not limited to, POU factors, upstream stimulatory factors (USF), EGR1, cAMP-response element binding protein/activating transcription factors (CREB/ATF), activating protein 1 (AP1), serum response factor (SRF), promoter selective transcription factor (SP1) and the runt related transcription factor 1 (RUNX1).

Thus, there may be significant therapeutic potential in inhibiting transcription factors in order to monitor the expression of genes involved in pain. Accordingly, what is needed are selective, readily available non-toxic transcription factor inhibitors.

SUMMARY OF THE INVENTION

The present invention satisfies these and other needs by providing oligonucleotide decoys, e.g., double-stranded oligonucleotides, pharmaceutical compositions thereof, and use of such oligonucleotide decoys and pharmaceutical compositions to modulate nociceptive signaling and to prevent and/or treat pain. Generally, the oligonucleotide decoys are transcription factor inhibitors.

In one aspect, oligonucleotide decoys comprising one or more transcription factor binding sites are provided. In certain embodiments, each transcription factor binding site binds to a transcription factor selected from the group consisting of POU1F1, POU2F, POU3F, POU4F1, POU5F1, USF, EGR1, CREB/ATF, AP1, CEBP, SRF, ETS1, MEF2, SP1, RUNX, NFAT, ELK1, ternary complex factors, STAT, GATA1, ELF1, nuclear factor—granulocyte/macrophage a, HNF1, ZFHX3, IRF, TEAD1, TBP, NFY, caccc-box binding factors, KLF4, KLF7, IKZF, MAF, REST, HSF, KCNIP3 and PPAR transcription factors. In certain embodiments, the transcription factor that binds to a transcription factor binding site is a human transcription factor. In other embodiments, the transcription factor that binds to a transcription factor binding site is a non-human transcription factor (e.g., an avian, mammal (e.g., mouse, rat, dog, cat, horse, cow, etc.), or primate transcription factor).

In a related aspect, oligonucleotide decoys comprising two or more transcription factor binding sites are provided. In certain embodiments, each transcription factor binding site binds to a transcription factor selected from the group consisting of POU1F1, POU2F, POU3F, POU5F1, USF, EGR1, CREB/ATF, AP1, CEBP, SRF, ETS1, MEF2, SP1, RUNX, NFAT, ELK1, ternary complex factors, STAT, GATA1, ELF1, nuclear factor—granulocyte/macrophage a, POU4F1, HNF1, ZFHX3, IRF, TEAD1, TBP, NFY, caccc-box binding factors, KLF4, KLF7, IKZF, MAF, REST, HSF, KCNIP3 and PPAR transcription factors. In certain embodiments, the relative position of the two transcription factor binding sites within the decoy modulates (e.g., increases) the binding affinity between a transcription factor and its transcription factor binding site, as compared to the binding affinity between the transcription factor and a decoy having a single transcription factor binding site. In certain embodiments, the relative position of the two transcription factor binding sites within the decoy promotes dimerization of transcription factors bound to the sites.

In certain embodiments, the oligonucleotide decoys comprise: (a) a sequence selected from the group consisting of SEQ ID NOs.: 1-40, 42, 45 and 47-53; or (b) a sequence having at least 50% identity with a sequence selected from the group consisting of SEQ ID NOs.: 1-40, 42, 45 and 47-53.

In certain embodiments, the oligonucleotide decoys can be provided as salts, hydrates, solvates or N-oxides derivatives.

In another aspect, pharmaceutical compositions comprising oligonucleotide decoys are provided. The pharmaceutical compositions generally comprise one or more oligonucleotide decoys and a pharmaceutically acceptable vehicle.

In another aspect, methods for treating or preventing pain are provided. The methods generally involve administering to a patient in need of such treatment or prevention a therapeutically effective amount of an oligonucleotide decoy of the invention, or a pharmaceutical composition thereof.

In another aspect, methods for modulating the transcription of a gene in a cell involved in nociceptive signaling, such as a dorsal root ganglion and/or spinal cord neuron, are provided. The methods generally comprise administering to the cell an effective amount of an oligonucleotide decoy.

In another aspect, methods for modulating nociceptive signaling in a cell involved in nociceptive signaling, such as a dorsal root ganglion and/or spinal cord neuron, are provided. The methods generally comprise administering to the cell an effective amount of an oligonucleotide decoy.

In yet another aspect, methods for monitoring the proteolytic degradation of proteins involved in nociceptive signaling in a cell are provided. The methods generally comprise administering to the cell an effective amount of an oligonucleotide decoy.

BRIEF DESCRIPTION OF THE DRAWINGS

FIGS. 3A-3E. A. SqRT-PCR sensitivity. PCR detection of CDK5R1 and ACTB mRNA was performed using a constant amount of starting cDNA material and increasing PCR cycles numbers. CDK5R1 and ACTB bands sizes are respectively 711 nt and 198 nt (left panel). Results indicated a linear relationship between signal intensities and PCR cycles number (right); black line: ACTB, grey line: CDK5R1, OD=band optical density. B. CDK5R1 mRNA up-regulation. Typical gel images of CDK5R1 cDNA detection before and after vitamin treatment are shown. The presence of EGR1 mRNA in control and vitamin-treated HL60 cells is also displayed. C. Decoy transfection in HL60 cells. Bright field and corresponding fluorescent pictures of HL60 cells 24 h after SEQ ID NO.: 40—fluorescein transfection (500 nM). Calculated transfection yield is 70%; n=3. D. Decoy toxicity. The percentage of dead HL60 cells 48 h after transfection of either SEQ ID NO.: 40 or SEQ ID NO.: 42 (500 and 1000 µM) was measured using the tryptan blue exclusion technique; values are given as Mean±SEM, n=2-4. E. Decoy specificity control. cDNA detection revealed a three-fold increase of CDK5R1 mRNA expression level after 1,25-Dihydroxyvitamin D3 treatment. Specificity of the decoy treatment was controlled by comparing the inhibition level of CDK5R1 mRNA expression conferred by SEQ ID NO.: 42 and the control sequence SEQ ID NO.: 43/46 (left graph). The specificity is further controlled by showing the lack of effect of SEQ ID NO.: 42 on the BCL2 gene regulation (right graph). Decoy sequences were transfected at 500 nM. Values are given as mean±SEM, mRNA expression levels are normalized against ACTB mRNA (arbitrary units); CTR=control, VIT=1,25-Dihydroxyvitamin D3 treatment. *=different from control, p<0.01, n=2-4.

FIGS. 5A-5E. A. Decoy transfection in PC12 cells. Bright field and corresponding fluorescent pictures of PC12 cells 24 h after fluorescein-conjugated SEQ ID NO.: 40 transfection. Calculated transfection yield is 80%; n=3. B. Inhibition of basal expression of pain genes. The expression levels of eleven pain genes expressed in PC12 cells are shown before (white bars) and 24 h after SEQ ID NO.: 42 transfection (dashed bars); values are given as Mean±SEM, *p≤0.1, **p≤0.05, n=2-5. C. Inhibition of up-regulation of pain genes. The expression level of eleven pain genes 24 h after NGF+forskolin treatment, before and after SEQ ID NO.: 42 transfection is shown; values are given as Mean±SEM, *p≤0.1, **p≤0.05 for different from control, n=2-4. D. Decoy inhibition illustration. Left panel: representative gel showing Bdkrb2 cDNA detection in control condition (C) and after SEQ ID NO.: 42 treatment (C+seq). Right panel: representative gel showing detection of Gch1 cDNA in control (C), NGF+forskolin (N) and NGF+forskolin+SEQ ID NO.: 42 (N+seq) conditions. E. Decoy specificity control. Gch1 and Nos1 genes were strongly up-regulated by NGF+ forskolin treatment (control=white bars, NGF+ forskolin=black bars). The specificity of the decoy treatment in PC12 cells was checked by showing the lack of effect by the control sequence SEQ ID NO.: 43/46 (grey bars) on the up-regulation of the Gch1 and Nos1 genes, as compare to SEQ ID NO.: 42 (dotted bars). Decoys were transfected at 500 nM. Values are given as Mean±SEM, expression values were normalized based on Gapdh expression level (arbitrary units).

FIGS. 7A-7D. A. Composite decoy EGR1 binding. Biotinylated SEQ ID NO.: 40 was used as a probe (128 nM) in the presence of increasing concentrations of competitor, the composite oligonucleotide decoy SEQ ID NO.: 45, in ELISA. The inhibition curve obtained for SEQ ID NO.: 41 competitor is given as a comparison. Data are given as a percentage of the maximum hEGR1 binding obtained with the probe in the absence of competitor; n=1-3. B. CREB/ATF and NFAT binding. The binding of SEQ ID NO.: 45 to hCREB/hATF and hNFATC1 factors was measured using competition ELISA. For hCREB/hATF binding, biotinylated SEQ ID NO.: 4 was used as a probe and SEQ ID NO.: 45 as a competitor. For hNFATC1 binding, biotinylated SEQ ID NO.: 15 was used as a probe and SEQ ID NO.: 45 as a competitor. White bars represent the binding of each probe alone (128 nM), black bars represents the binding of each probe in presence of competitor (2 µM). C. Dose response. The efficacy of SEQ ID NO.: 45 in inhibiting hEGR1 activity in HL60 cells was measured following the inhibition of CDK5R1 expression. CDK5R1 mRNA inhibition curves of both SEQ ID NO.: 45 and SEQ ID NO.: 41 are displayed for comparison; CDK5R1 expression level is normalized against ACTB, Mean±SEM are given as a percentage of inhibition of the maximum CDK5R1 expression level 48 h after 1,25-Dihydroxyvitamin D3 application; n=2-4. D. Pain genes inhibition. Relative inhibition of Bdkrb2 and Scn9a genes in PC12 cells by independent treatments with either SEQ ID NO.: 4, SEQ ID NO.: 15, SEQ ID NO.: 42, or SEQ ID NO.: 45. Decoys are transfected at 500 nM; values are given as mean±SEM, expression values were normalized on Gapdh expression level (arbitrary units); *p<0.1, **p<0.05 for different from either SEQ ID NO.: 4, SEQ ID NO.: 15 or SEQ ID NO.: 42.

DETAILED DESCRIPTION OF THE INVENTION

Definitions

Figure 1A:
FIGS. 1A-1C. A. Decoy duplex annealing control. SEQ ID NO.: 40 (34 bp) and SEQ ID NO.: 44 (20 bp) were used to control the annealing of different sizes decoys sequences on a 2.5 agarose gel. Individual single strands migrate faster than double stranded decoys. B. Transcription factor ELISA sensitivity. hEGR1 binding to biotin-coupled SEQ ID NO.: 40 in the presence of either 5 µg, 10 µg or 15 µg of K-562 cells (TPA stimulated) nuclear extracts was measured. $OD_{450\ nm}$ values obtained for each protein quantity are shown. C. Specificity control. The absence of non-specific binding by decoy sequences in ELISA experiments was controlled by comparing the hEGR1 binding activity of SEQ ID NO.: 40 to a mismatched and mutated oligonucleotide formed by annealing the sequence of SEQ ID NO.: 43 with the sequence of SEQ ID NO.: 46 (referred to hereinafter as SEQ ID NO.: 43/46). Both SEQ ID NO.: 40 and SEQ ID NO.: 43/46 were biotinylated. $OD_{450\ nm}$ values obtained for each sequence are shown.

"Binding," as used in the context of transcription factors binding to oligonucleotide decoys, refers to a direct interaction (e.g., non-covalent bonding between the transcription factor and oligonucleotide decoy, including hydrogen-bonding, van der Waals bonding, etc.) between a transcription factor and an oligonucleotide decoy. Accordingly, an oligonucleotide that does not bind to a transcription factor does not directly interact with said transcription factor.

"Chronic" refers to a period of time comprising months (e.g., at least two months) or years.

"Compounds" refers to double-stranded oligonucleotides, also referred to herein as oligonucleotide decoys. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. Compounds may also exist in several tautomeric forms including the enol form, the keto form and mixtures thereof. Accordingly, the chemical structures depicted herein encompass all possible tautomeric forms of compounds. Compounds described herein also include isotopically labeled compounds where one or more atoms have an atomic mass different from the atomic mass conventionally found in nature. Examples of isotopes that may be incorporated into the compounds of the invention include, but are not limited to, $^{2}H$, $^{3}H$, $^{11}C$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. All physical forms are equivalent for the uses contemplated herein. Further, it should be understood, when partial structures of the compounds are illustrated, that brackets indicate the point of attachment of the partial structure to the rest of the molecule.

"Modulation of gene expression level" refers to any change in gene expression level, including an induction or activation (e.g., an increase in gene expression), an inhibition or suppression (e.g., a decrease in gene expression), or a stabilization (e.g., prevention of the up-regulation or down-regulation of a gene that ordinarily occurs in response to a stimulus, such as a pain-inducing stimulus).

"Nociceptive signaling" refers to molecular and cellular mechanisms involved in the detection of a noxious stimulus or of a potentially harmful stimulus, which leads to the perception of pain, including neurotransmitter synthesis and release, neurotransmitter-induced signaling, membrane depolarization, and related intra-cellular and inter-cellular signaling events.

"Oligonucleotide" refers to any double-stranded, nucleic acid-containing polymer generally less than approximately 200 nucleotides (or 100 base pairs) and including, but not limited to, DNA, RNA and RNA-DNA hybrids. The term encompasses sequences that include any of the known base analogs of DNA and RNA including, but not limited to, 2,6-diaminopurine, 5-carboxymethylaminomethyl-2-thiouracil, 5-carboxymethylaminomethyluracil, dihydrouracil, inosine, uracil-5-oxyacetic acid, N6-isopentenyladenine, 1-methyladenine, N-uracil-5-oxyacetic acid methylester, queosine, 2-thiocytosine, 5-bromouracil, methylphosphonate, phosphorodithioate, ormacetal, 3'-thioformacetal, nitroxide backbone, sulfone, sulfamate, morpholino derivatives, locked nucleic acid (LNA) derivatives, and/or peptide nucleic acid (PNA) derivatives. In some embodiments, the oligonucleotide is composed of two complementary single-stranded oligonucleotides that are annealed together. In other embodiments, the oligonucleotide is composed of one single-stranded oligonucleotide that forms intramolecular base pairs to create a substantially double-stranded structure.

"Pain" refers to an unpleasant sensory and emotional experience that is associated with actual or potential tissue damage or described in such terms. All of the different manifestations and qualities of pain, including mechanical pain (e.g., induced by a mechanical stimulus or by body motion), temperature-induced pain (e.g., pain induced by hot, warm and/or cold temperatures), and chemically-induced pain (e.g., pain induced by a chemical). In certain embodiments, pain is chronic, sub-chronic, acute, or sub-acute. In certain embodiments, pain features hyperalgesia (i.e., an increased sensitivity to a painful stimulus) and/or allodynia (i.e., a painful response to a usually non-painful stimulus). In certain embodiments, pain is pre-existing in a patient. In other embodiments, pain is iatrogenic, induced in a patient (e.g., post-operative pain).

"Pharmaceutically acceptable salt" refers to a salt of a compound, which possesses the desired pharmacological activity of the parent compound. Such salts include, but are not limited to: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Patient" includes any animal, including birds, mammals, primates, and humans.

"Preventing" or "prevention" refers to (1) a reduction in the risk of acquiring a disease or disorder (e.g., causing at least one of the clinical symptoms of a disease not to develop in a patient that may be exposed to or predisposed to the disease but does not yet experience or display symptoms of the disease), or (2) a reduction in the likely severity of a symptom associated with a disease or disorder (e.g., reducing the likely severity of at least one of the clinical symptoms of a disease in a patient that may be exposed to or predisposed to the disease but does not yet experience or display symptoms of the disease).

"Sub-acute" refers to a period of time comprising hours (e.g., 1 h-24 h)

"Sub-chronic" refers to a period of time comprising days or months (e.g., less than two months).

"Treating" or "treatment" of any disease or disorder refers, in some embodiments, to ameliorating the disease or disorder (i.e., arresting or reducing the development of the disease or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

"Therapeutically effective amount" means the amount of a compound that, when administered to a patient, is sufficient to effect such treatment of a particular disease or condition. The "therapeutically effective amount" will vary depending on the compound, the disease, the severity of the disease, and the age, weight, etc., of the patient to be treated.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

Oligonucleotide Decoys

The present invention relates to oligonucleotide decoys, pharmaceutical compositions thereof, and use of such oligonucleotide decoys and pharmaceutical compositions to modulate nociceptive signaling and to prevent and/or treat pain.

In certain embodiments, the invention features oligonucleotide decoys comprising one or more (e.g., 1, 2, 3, 4, 5, etc.) transcription factor binding sites. In related embodiments, each transcription factor binding site binds to a transcription factor selected from the group consisting of POU1F1, POU2F, POU3F, POU4F1, POU5F1, USF, EGR1, CREB/ATF, AP1, CEBP, SRF, ETS1, MEF2, SP1, RUNX, NFAT, ELK1, ternary complex factors, STAT, GATA1, ELF1, nuclear factor—granulocyte/macrophage a, HNF1, ZFHX3, IRF, TEAD1, TBP, NFY, caccc-box binding factors, KLF4, KLF7, IKZF, MAF, REST, HSF, KCNIP3 and PPAR transcription factors. In certain embodiments, transcription factor binding sites bind to two or more members of a family of closely-related transcription factors. Representative members of such transcription factor families can be selected from the group consisting of POU1F1, POU2F, POU3F, POU4F1, POU5F1, USF, EGR1, CREB/ATF, AP1, CEBP, SRF, ETS1, MEF2, SP1, RUNX, NFAT, ELK1, ternary complex factors, STAT, GATA1, ELF1, nuclear factor—granulocyte/macrophage a, HNF1, ZFHX3, IRF, TEAD1, TBP, NFY, caccc-box binding factors, KLF4, KLF7, IKZF, MAF, REST, HSF, KCNIP3 and PPAR transcription factors. Thus, in certain embodiments, an oligonucleotide decoy that binds to, e.g., EGR1, can also bind to one or more additional family members, e.g., EGR2, EGR3, EGR4.

In certain embodiments, the oligonucleotide decoys comprise two or more (e.g., 2, 3, 4, 5, etc.) transcription factor binding sites. In related embodiments, each transcription factor binding site binds to a transcription factor selected from the group consisting of POU1F1, POU2F, POU3F, POU4F1, POU5F1, USF, EGR1, CREB/ATF, AP1, CEBP, SRF, ETS1, MEF2, SP1, RUNX, NFAT, ELK1, ternary complex factors, STAT, GATA1, ELF1, nuclear factor—granulocyte/macrophage a, HNF1, ZFHX3, IRF, TEAD1, TBP, NFY, caccc-box binding factors, KLF4, KLF7, IKZF, MAF, REST, HSF, KCNIP3 and PPAR transcription factors. In certain embodiments, the relative position of the two or more transcription factor binding sites within the decoy modulates (e.g., increases or decreases) the binding affinity between a target transcription factor (i.e., the transcription factor that a particular binding site is designed to bind to) and its transcription factor binding site, e.g., as compared to the binding affinity between the transcription factor and a decoy having a single transcription factor binding site (e.g., a consensus binding site) specific to the transcription factor. Thus, the relative position of the two transcription factor binding sites within an oligonucleotide decoy of the invention can increase the affinity of the oligonucleotide decoy for a target transcription factor (e.g., for one or more of the transcription factors targeted by the decoy). In certain embodiments, the increase in affinity of the oligonucleotide decoy for a target transcription factor is 1.2 fold or greater (e.g., about 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 fold, or more). In certain embodiments, the relative position of the two transcription factor binding sites within an oligonucleotide decoy promotes protein-protein interactions between transcription factors bound to the sites, e.g., homodimerization or heterodimerization of the transcription factors. In certain embodiments, such protein-protein interactions between transcription factors stabilize their interactions, e.g., binding, to the oligonucleotide decoy, thereby increasing the binding affinity of the oligonucleotide decoy for one or more of the target transcription factors.

In certain embodiments, a transcription factor that binds to a transcription factor binding site present in an oligonucleotide decoy is a human transcription factor. In other embodiments, the transcription factor that binds to a transcription factor binding site in an oligonucleotide decoy is a non-human, e.g., an avian, mammal (e.g., mouse, rat, dog, cat, horse, cow, etc.), or primate, transcription factor.

In certain embodiments, the transcription factor binding sites of an oligonucleotide decoy each bind to the same transcription factor, e.g., EGR1. In other embodiments, the transcription factor binding sites of an oligonucleotide decoy bind to different transcription factors, e.g., different members of a closely related family of transcription factors (e.g., different members of the EGR1 family) or a combination of transcription factors selected from the group consisting of POU1F1, POU2F, POU3F, POU4F1, POU5F1, USF, EGR1, CREB/ATF, AP1, CEBP, SRF, ETS1, MEF2, SP1, RUNX, NFAT, ELK1, ternary complex factors, STAT, GATA1, ELF1, nuclear factor—granulocyte/macrophage a, HNF1, ZFHX3, IRF, TEAD1, TBP, NFY, caccc-box binding factors, KLF4, KLF7, IKZF, MAF, REST, HSF, KCNIP3 and PPAR transcription factors.

In certain embodiments, the transcription factor binding sites of an oligonucleotide decoy are separated from each other by a linker sequence. Linker sequences can be 1, 2, 3, 4, 5, 6, 7, 8, 9, 10, or more base pairs in length. Typically, linker sequences will be two to five base pairs in length. In other embodiments, the transcription factor binding sites can be immediately adjacent to one another (e.g., no linker sequence is present) or overlapping. In cases where the transcription factor binding sites are overlapping, the transcription factor binding sites may share 1, 2, 3, 4, 5, or more base pairs. Alternatively, one or both of the transcription factor binding sites may be lacking base pairs that otherwise form part of a consensus binding sequence for the transcription factor(s) that bind to the site. In general, however, base pairs that are critical to the binding interaction between a transcription factor binding site and the transcription factors that bind to the site (e.g., base pairs that are essentially invariant in a consensus binding sequence for a particular transcription factor) are not shared or missing when transcription binding sequences are overlapping.

In certain embodiments, oligonucleotide decoys comprise flanking sequences located at each end of the decoy sequence. Flanking sequences can be 1, 2, 3, 4, 5, 6, or more base pairs in length. In general, flanking sequences are two to five base pairs in length. In preferred embodiments, 5' flanking sequences starts with a G/C base pair and 3' flanking sequences terminate in a G/C base pair. In preferred embodiments, flanking sequences do not form part of a transcription factor binding site and/or do not interact with or bind to transcription factors. In other embodiments, flanking sequences form weak interactions with transcription factors bound to an adjacent transcription factor binding site.

In certain embodiments, oligonucleotide decoys are generally at least 10, 11, 12, 13, 14, 15, or more base pairs in length. In related embodiments, oligonucleotide decoys are generally less than 65, 60, 55, 50, or 45 base pairs in length. In preferred embodiments, oligonucleotide decoys are about 20 to 40 base pairs in length. In other embodiments, oligonucleotide decoys are about 20 to 35, 25 to 40, or 25 to 35 base pairs in length.

In certain embodiments, the oligonucleotide decoys comprise: (a) a sequence selected from the group consisting of SEQ ID NOs.: 1-40, 42, 45 and 47-53; or (b) a sequence having at least 50%, 55%, 60%, 65%, 70%, 75%, 80%, 85%, 88%, 89%, 90%, 91%, 92%, 93%, 94%, 95%, 96%, 97%, 98%, or 99% identity with a sequence selected from the group consisting of SEQ ID NOs.: 1-40, 42, 45 and 47-53. In related embodiments, the oligonucleotide decoys comprise a sequence having at least 90% identity with a sequence selected from the group consisting of SEQ ID NOs.: 1-39, 42, 45 and 47-52. In other embodiments, the oligonucleotide decoys comprise a sequence having at least 85% identity with a sequence selected from the group consisting of SEQ ID NOs.: 1-17, 19-39, 42, 45 and 47-53. In other embodiments, the oligonucleotide decoys comprise a sequence having at least 80% identity with a sequence selected from the group consisting of SEQ ID NOs.: 1-5, 7-17, 19-39, 42, 45 and 47-53. In other embodiments, the oligonucleotide decoys comprise a sequence having at least 75% identity with a sequence selected from the group consisting of SEQ ID NOs.: 1-4, 7-9, 13, 15-17, 19-23, 26-39, 45, 48, 50, 51 and 53. In other embodiments, the oligonucleotide decoys comprise a sequence having at least 70% identity with a sequence selected from the group consisting of SEQ ID NOs.: 1-3, 7-9, 13, 15-17, 19-23, 26, 28, 30, 32, 34-36, 38-39 and 48. In other embodiments, the oligonucleotide decoys comprise a sequence having at least 65% identity with a sequence selected from the group consisting of SEQ ID NOs.: 2-3, 9, 13, 15-16, 19-23, 26, 28, 30, 32, 34-36, 38 and 39. In other embodiments, the oligonucleotide decoys comprise a sequence having at least 60% identity with a sequence selected from the group consisting of SEQ ID NOs.: 2, 13, 15-16, 21, 23, 26, 30, 32, 34-36, 38 and 39. In still other embodiments, the oligonucleotide decoys comprise a sequence having at least 55% identity with a sequence selected from the group consisting of SEQ ID NOs.: 16, 23, 30, 32, 34, 35, 38 and 39. In still other embodiments, the oligonucleotide decoys comprise a sequence having at least 50% identity with a sequence selected from the group consisting of SEQ ID NOs.: 30, 32, 35, and 38.

In certain embodiments, an oligonucleotide decoy comprises a double-stranded sequence represented by formula (1):

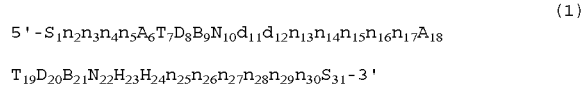

$$5'-S_1n_2n_3n_4n_5A_6T_7D_8B_9N_{10}d_{11}d_{12}n_{13}n_{14}n_{15}n_{16}n_{17}A_{18}$$
$$T_{19}D_{20}B_{21}N_{22}H_{23}H_{24}n_{25}n_{26}n_{27}n_{28}n_{29}n_{30}S_{31}-3'$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "D" can be an A, G, or T nucleotide, "B" can be a C, G, or T nucleotide, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (1) has at least about 70%, 75%, 80%, 85%, 88%, 90%, 91%, 92%, 93%, 94%, 95%, 96%, 97%, 98%, or 99% sequence identity to the nucleotide sequence of SEQ ID NO.: 1. Such oligonucleotide decoys can bind to POU2F1 transcription factor. In certain embodiments, such oligonucleotide decoys can bind to one or more transcription factors closely related to POU2F1 transcription factor, such as POU2F2, POU3F1-2, and POU5F1.

In certain embodiments, an oligonucleotide decoy represented by formula (1) comprises a deletion of one or more (e.g., 1, 2, 3, 4, 5, 6, or 7) nucleotides selected from the group consisting of $d_{11}$, $d_{12}$, $n_{13}$, $n_{14}$, $n_{15}$, $n_{16}$, and $n_{17}$. In certain embodiments, oligonucleotide decoys comprising a deletion of one or more nucleotides selected from the group consisting of $d_{11}$, $d_{12}$, $n_{13}$, $n_{14}$, $n_{15}$, $n_{16}$, and $n_{17}$ have at least 70% identity to the nucleotide sequence of SEQ ID NO.: 1.

In certain embodiments, an oligonucleotide decoy comprises a double-stranded sequence represented by formula (2):

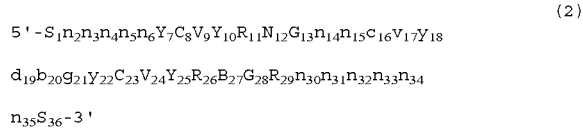

$$5'-S_1n_2n_3n_4n_5n_6Y_7C_8V_9Y_{10}R_{11}N_{12}G_{13}n_{14}n_{15}c_{16}v_{17}y_{18}$$
$$d_{19}b_{20}g_{21}y_{22}C_{23}V_{24}Y_{25}R_{26}B_{27}G_{28}R_{29}n_{30}n_{31}n_{32}n_{33}n_{34}$$
$$n_{35}S_{36}-3'$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "D" can be an A, G, or T nucleotide, "B" can be a C, G, or T nucleotide, "R" can be a G or an A, "V" can be an A, C, or G, "Y" can be a C or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (2) has at least about 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 2. Such oligonucleotide decoys can bind to USF1 transcription factor. In certain embodiments, such oligonucleotide decoys can bind to one or more transcription factors closely related to USF1 transcription factor, such as USF2.

In certain embodiments, an oligonucleotide decoy represented by formula (2) comprises a deletion of one or more (e.g., 1, 2, 3, 4, 5, 6, 7, 8 or 9) nucleotides selected from the group consisting of $n_{14}$, $n_{15}$, $c_{16}$, $v_{17}$, $y_{18}$, $d_{19}$, $b_{20}$, $g_{21}$, and $y_{22}$. In certain embodiments, oligonucleotide decoys comprising a deletion of one or more nucleotides selected from the group consisting of $n_{14}$, $n_{15}$, $c_{16}$, $v_{17}$, $y_{18}$, $d_{19}$, $b_{20}$, $g_{21}$, and $y_{22}$ have at least 60% identity to the nucleotide sequence of SEQ ID NO.: 2.

In certain embodiments, an oligonucleotide decoy comprises a double-stranded sequence represented by formula (3):

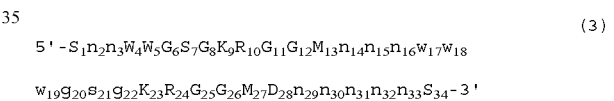

$$5'-S_1n_2n_3W_4W_5G_6S_7G_8K_9R_{10}G_{11}G_{12}M_{13}n_{14}n_{15}n_{16}w_{17}w_{18}$$
$$w_{19}g_{20}s_{21}g_{22}K_{23}R_{24}G_{25}G_{26}M_{27}D_{28}n_{29}n_{30}n_{31}n_{32}n_{33}S_{34}-3'$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, 'W' can be a A or a T, "D" can be an A, G, or T nucleotide, "R" can be a G or an A, "K" can be a T or a G, "M" can be a C or a A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (3) has at least about 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 3. Such oligonucleotide decoys can bind to EGR1 transcription factor. In certain embodiments, such oligonucleotide decoys can bind to one or more transcription factors closely related to EGR1 transcription factor, such as EGR2-4.

In certain embodiments, an oligonucleotide decoy represented by formula (3) comprises a deletion of one or more (e.g., 1, 2, 3, 4, 5, 6, 7, 8 or 9) nucleotides selected from the group consisting of $n_{14}$, $n_{15}$, $n_{16}$, $w_{17}$, $w_{18}$, $w_{19}$, $g_{20}$, $s_{21}$, and $g_{22}$. In certain embodiments, oligonucleotide decoys comprising a deletion of one or more nucleotides selected from the group consisting of $n_{14}$, $n_{15}$, $n_{16}$, $w_{17}$, $w_{18}$, $w_{19}$, $g_{20}$, $s_{21}$, and $g_{22}$ have at least 65% identity to the nucleotide sequence of SEQ ID NO.: 3.

In certain embodiments, an oligonucleotide decoy comprises a double-stranded sequence represented by formula (4):

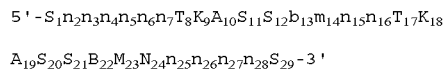

(4)

wherein "A" is an adenine nucleotide, "C" is a cytosine nucleotide, "G" is a guanine nucleotide, "T" is a thymine nucleotide, "S" can be a G or C nucleotide, "N" can be any nucleotide, "B" can be a C, G or T, "K" can be a T or a G, "M" can be a C or a A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (4) has at least about 75%, 80%, 85%, 88%, 90%, 91%, 92%, 93%, 94%, 95%, 96%, 97%, 98%, or 99% sequence identity to the nucleotide sequence of SEQ ID NO.: 4. Such oligonucleotide decoys can bind to CREB1 transcription factor. In certain embodiments, such oligonucleotide decoys can bind to one or more transcription factors closely related to CREB1 transcription factor, such as CREB3-5 and ATF1-7.

In certain embodiments, an oligonucleotide decoy represented by formula (4) comprises a deletion of one or more (e.g., 1, 2, 3 or 4) nucleotides selected from the group consisting of $b_{13}$, $m_{14}$, $n_{15}$, and $n_{16}$. In certain embodiments, oligonucleotide decoys comprising a deletion of one or more nucleotides selected from the group consisting of $b_{13}$, $m_{14}$, $n_{15}$, and $n_{16}$ have at least 75% identity to the nucleotide sequence of SEQ ID NO.: 4.

In certain embodiments, an oligonucleotide decoy comprises a double-stranded sequence represented by formula (5):

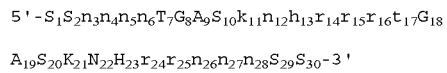

(5)

wherein "A" is an adenine nucleotide, "C" is a cytosine nucleotide, "G" is a guanine nucleotide, "T" is a thymine nucleotide, "S" can be a G or C nucleotide, "N" can be any nucleotide, "R" can be a G or an A, "K" can be a T or a G, "H" can be a C, T or a A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (5) has at least about 80%, 85%, 88%, 90%, 91%, 92%, 93%, 94%, 95%, 96%, 97%, 98%, or 99% sequence identity to the nucleotide sequence of SEQ ID NO.: 5. Such oligonucleotide decoys can bind to AP1/JUN transcription factors. In certain embodiments, such oligonucleotide decoys can bind to one or more transcription factors closely related to AP1/JUN transcription factors, such as AP1/JUN-B, -D and AP1/FOS.

In certain embodiments, an oligonucleotide decoy represented by formula (5) comprises a deletion of one or more (e.g., 1, 2, 3, 4, 5, 6 or 7) nucleotides selected from the group consisting of $k_{11}$, $n_{12}$, $h_{13}$, $r_{14}$, $r_{15}$, $r_{16}$, and $t_{17}$. In certain embodiments, oligonucleotide decoys comprising a deletion of one or more nucleotides selected from the group consisting of $k_{11}$, $n_{12}$, $h_{13}$, $r_{14}$, $r_{15}$, $r_{16}$, and $t_{17}$ have at least 80% identity to the nucleotide sequence of SEQ ID NO.: 5.

In certain embodiments, an oligonucleotide decoy comprises a double-stranded sequence represented by formula (6):

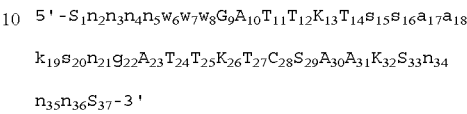

(6)

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be A or T, "K" can be a T or a G, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (6) has at least about 85%, 88%, 90%, 91%, 92%, 93%, 94%, 95%, 96%, 97%, 98%, or 99% sequence identity to the nucleotide sequence of SEQ ID NO.: 6. Such oligonucleotide decoys can bind to CEBPA transcription factor. In certain embodiments, such oligonucleotide decoys can bind to one or more transcription factors closely related to CEBPA transcription factor, such as CEBP-B, -D, -E, -G, -Z.

In certain embodiments, an oligonucleotide decoy represented by formula (6) comprises a deletion of one or more (e.g., 1, 2, 3, 4, 5, 6, 7 or 8) nucleotides selected from the group consisting of $s_{15}$, $s_{16}$, $a_{17}$, $a_{18}$, $k_{19}$, $s_{20}$, $n_{21}$, and $g_{22}$. In certain embodiments, oligonucleotide decoys comprising a deletion of one or more nucleotides selected from the group consisting of $s_{15}$, $s_{16}$, $a_{17}$, $a_{18}$, $k_{19}$, $s_{20}$, $n_{21}$, and $g_{22}$ have at least 85% identity to the nucleotide sequence of SEQ ID NO.: 6.

In certain embodiments, an oligonucleotide decoy comprises a double-stranded sequence represented by formula (7):

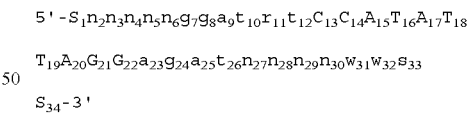

(7)

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be a A or T, Y can be a C or T, "R" can be a G or A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (7) has at least about 70%, 75%, 80%, 85%, 88%, 90%, 91%, 92%, 93%, 94%, 95%, 96%, 97%, 98%, or 99% sequence identity to the nucleotide sequence of SEQ ID NO.: 7. Such oligonucleotide decoys can bind to SRF transcription factor. In certain embodiments, such oligonucleotide decoys can bind to one or more transcription factors closely related to SRF transcription factor, such as ELK1.

In certain embodiments, an oligonucleotide decoy represented by formula (7) comprises a deletion of one or more (e.g., 1, 2, 3, 4, 5, 6, 7, 8, 9, 10, 11, 12, 13, 14, 15, 16 or 17) nucleotides selected from the group consisting of $g_7$, $g_8$, $a_9$, $t_{10}$, $r_{11}$, $t_{12}$, $a_{23}$, $g_{24}$, $a_{25}$, $t_{26}$, $n_{27}$, $n_{28}$, $n_{29}$, $n_{30}$, $w_{31}$, $w_{32}$ and $s_{33}$. In certain embodiments, oligonucleotide decoys comprising a deletion of one or more nucleotides selected from the group consisting of $g_7$, $g_8$, $a_9$, $t_{10}$, $r_{11}$, $t_{12}$, $a_{23}$, $g_{24}$, $a_{25}$, $t_{26}$, $n_{27}$, $n_{28}$, $n_{29}$, $n_{30}$, $w_{31}$, $w_{32}$ and $s_{33}$ have at least 70% identity to the nucleotide sequence of SEQ ID NO.: 7.

In certain embodiments, an oligonucleotide decoy comprises a double-stranded sequence represented by formula (8):

$$5'-S_1n_2n_3n_4n_5C_6A_7G_8G_9A_{10}d_{11}d_{12}d_{13}d_{14}d_{15}d_{16}d_{17}d_{18}$$
$$d_{19}T_{20}C_{21}C_{22}A_{23}T_{24}A_{25}T_{26}T_{27}A_{28}G_{29}n_{30}n_{31}n_{32}n_{33}$$
$$S_{34}-3' \quad (8)$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "D" can be a A, T or G, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (8) has at least about 70%, 75%, 80%, 85%, 88%, 90%, 91%, 92%, 93%, 94%, 95%, 96%, 97%, 98%, or 99% sequence identity to the nucleotide sequence of SEQ ID NO.: 8. Such oligonucleotide decoys can bind to SRF transcription factor. In certain embodiments, such oligonucleotide decoys can bind to one or more transcription factors closely related to SRF transcription factor, such as ETS1.

In certain embodiments, an oligonucleotide decoy represented by formula (8) comprises a deletion of one or more (e.g., 1, 2, 3, 4, 5, 6, 7, 8 or 9) nucleotides selected from the group consisting of $d_{11}$, $d_{12}$, $d_{13}$, $d_{14}$, $d_{15}$, $d_{16}$, $d_{17}$, $d_{18}$ and $d_{19}$. In certain embodiments, oligonucleotide decoys comprising a deletion of one or more nucleotides selected from the group consisting of $d_{11}$, $d_{12}$, $d_{13}$, $d_{14}$, $d_{15}$, $d_{16}$, $d_{17}$, $d_{18}$ and $d_{19}$ have at least 70% identity to the nucleotide sequence of SEQ ID NO.: 8.

In certain embodiments, an oligonucleotide decoy comprises a double-stranded sequence represented by formula (9):

$$5'-S_1n_2n_3n_4n_5C_6T_7A_8W_9A_{10}M_{11}W_{12}T_{13}A_{14}A_{15}n_{16}n_{17}n_{18}$$
$$n_{19}C_{20}t_{21}A_{22}W_{23}A_{24}A_{25}A_{26}T_{27}A_{28}A_{29}A_{30}A_{31}n_{32}n_{33}$$
$$n_{34}S_{35}-3' \quad (9)$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be a A or an T, "M" can be a C or an A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (9) has at least about 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 9. Such oligonucleotide decoys can bind to MEF2A transcription factor. In certain embodiments, such oligonucleotide decoys can bind to one or more transcription factors closely related to MEF2A transcription factor, such as MEF2B-C.

In certain embodiments, an oligonucleotide decoy represented by formula (9) comprises a deletion of one or more (e.g., 1, 2, 3, 4, 5 or 6) nucleotides selected from the group consisting of $n_{16}$, $n_{17}$, $n_{18}$, $n_{19}$, $c_{20}$ and $t_{21}$. In certain embodiments, oligonucleotide decoys comprising a deletion of one or more nucleotides selected from the group consisting of $n_{16}$, $n_{17}$, $n_{18}$, $n_{19}$, $c_{20}$ and $t_{21}$ have at least 65% identity to the nucleotide sequence of SEQ ID NO.: 9.

In certain embodiments, an oligonucleotide decoy comprises a double-stranded sequence represented by formula (10):

$$5'-n_1n_2n_3n_4R_5R_6G_7S_8C_9S_{10}K_{11}r_{12}r_{13}n_{14}n_{15}n_{16}r_{17}r_{18}$$
$$G_{19}S_{20}C_{21}K_{22}R_{23}R_{24}N_{25}n_{26}n_{27}n_{28}n_{29}n_{30}-3' \quad (10)$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "K" can be a T or a G, "R" can be a G or an A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (10) has at least about 80%, 85%, 88%, 90%, 91%, 92%, 93%, 94%, 95%, 96%, 97%, 98%, or 99% sequence identity to the nucleotide sequence of SEQ ID NO.: 10. Such oligonucleotide decoys can bind to SP1 transcription factor. In certain embodiments, such oligonucleotide decoys can bind to one or more transcription factors closely related to SP1 transcription factor, such as SP2-8.

In certain embodiments, an oligonucleotide decoy represented by formula (10) comprises a deletion of one or more (e.g., 1, 2, 3, 4, 5, 6 or 7) nucleotides selected from the group consisting of $r_{12}$, $r_{13}$, $n_{14}$, $n_{15}$, $n_{16}$, $r_{17}$, and $r_{18}$. In certain embodiments, oligonucleotide decoys comprising a deletion of one or more nucleotides selected from the group consisting of $n_{16}$, $n_{17}$, $n_{18}$, $n_{19}$, $c_{20}$ and $t_{21}$ have at least 80% identity to the nucleotide sequence of SEQ ID NO.: 10.

In certain embodiments, an oligonucleotide decoy comprises a double-stranded sequence represented by formula (11):

$$5'-n_1n_2n_3n_4n_5G_6G_7C_8G_9G_{10}G_{11}G_{12}s_{13}s_{14}s_{15}s_{16}s_{17}s_{18}$$
$$s_{19}s_{20}s_{21}s_{22}s_{23}C_{24}G_{25}G_{26}G_{27}C_{28}G_{29}G_{30}T_{31}T_{32}T_{33}A_{34}$$
$$C_{35}-3' \quad (11)$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (11) has at least about 80%, 85%, 88%, 90%, 91%, 92%, 93%, 94%, 95%, 96%, 97%, 98%, or 99% sequence identity to the nucleotide sequence of SEQ ID NO.: 11. Such oligonucleotide decoys can bind to SP1 transcription factor. In certain embodiments, such oligonucleotide decoys can bind to one or more transcription factors closely related to SP1 transcription factor, such as SP2-8.

In certain embodiments, an oligonucleotide decoy represented by formula (11) comprises a deletion of one or more (e.g., 1, 2, 3, 4, 5, 6, 7, 8, 9 10 or 11) nucleotides selected from the group consisting of $s_{13}$, $s_{14}$, $s_{15}$, $s_{16}$, $s_{17}$, $s_{18}$, $s_{19}$, $s_{20}$, $s_{21}$, $s_{22}$, and $s_{23}$. In certain embodiments, oligonucleotide decoys comprising a deletion of one or more nucleotides selected from the group consisting of $s_{13}$, $s_{14}$, $s_{15}$, $s_{16}$, $s_{17}$, $s_{18}$, $s_{19}$, $s_{20}$, $s_{21}$, $s_{22}$, and $s_{23}$ have at least 80% identity to the nucleotide sequence of SEQ ID NO.: 11.

In certain embodiments, an oligonucleotide decoy comprises a double-stranded sequence represented by formula (12):

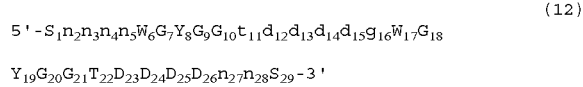

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be a A or a T, Y can be a C or a T, "D" can be a A, T or a G, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (12) has at least about 80%, 85%, 88%, 90%, 91%, 92%, 93%, 94%, 95%, 96%, 97%, 98%, or 99% sequence identity to the nucleotide sequence of SEQ ID NO.: 12. Such oligonucleotide decoys can bind to RUNX1 transcription factor. In certain embodiments, such oligonucleotide decoys can bind to one or more transcription factors closely related to RUNX1 transcription factor, such as RUNX2-3.

In certain embodiments, an oligonucleotide decoy represented by formula (12) comprises a deletion of one or more (e.g., 1, 2, 3, 4, 5 or 6) nucleotides selected from the group consisting of $t_{11}$, $h_{12}$, $h_{13}$, $h_{14}$, $h_{15}$, and $g_{16}$. In certain embodiments, oligonucleotide decoys comprising a deletion of one or more nucleotides selected from the group consisting of $t_{11}$, $h_{12}$, $h_{13}$, $h_{14}$, $h_{15}$, and $g_{16}$ have at least 80% identity to the nucleotide sequence of SEQ ID NO.: 12.

In certain embodiments, an oligonucleotide decoy comprises a double-stranded sequence represented by formula (13):

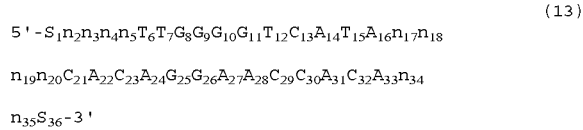

wherein "A" is an adenine nucleotide, "C" is a cytosine nucleotide, "G" is a guanine nucleotide, "T" is a thymine nucleotide, "S" can be a G or C nucleotide, "N" can be any nucleotide, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (13) has at least about 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 13. Such oligonucleotide decoys can bind to RUNX1 transcription factor. In certain embodiments, such oligonucleotide decoys can bind to one or more transcription factors closely related to RUNX1 transcription factor, such as RUNX2-3.

In certain embodiments, an oligonucleotide decoy represented by formula (13) comprises a deletion of one or more (e.g., 1, 2, 3 or 4) nucleotides selected from the group consisting of $n_{17}$, $n_{18}$, $n_{19}$ and $n_{20}$. In certain embodiments, oligonucleotide decoys comprising a deletion of one or more nucleotides selected from the group consisting of $n_{17}$, $n_{18}$, $n_{19}$ and $n_{20}$ have at least 60% identity to the nucleotide sequence of SEQ ID NO.: 13.

In certain embodiments, an oligonucleotide decoy comprises a double-stranded sequence represented by formula (14):

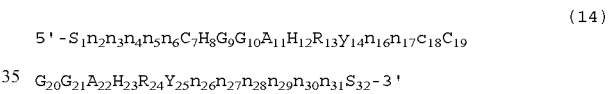

wherein "A" is an adenine nucleotide, "C" is a cytosine nucleotide, "G" is a guanine nucleotide, "T" is a thymine nucleotide, "S" can be a G or C nucleotide, "N" can be any nucleotide, "R" can be G or A, "H" can be A, T or C, "Y" can be a C or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (14) has at least about 80%, 85%, 88%, 90%, 91%, 92%, 93%, 94%, 95%, 96%, 97%, 98%, or 99% sequence identity to the nucleotide sequence of SEQ ID NO.: 14. Such oligonucleotide decoys can bind to ETS1 transcription factor. In certain embodiments, such oligonucleotide decoys can bind to one or more transcription factors closely related to ETS1 transcription factor, such as ELK1.

In certain embodiments, an oligonucleotide decoy represented by formula (14) comprises a deletion of one or more (e.g., 1, 2, 3, 4 or 5) nucleotides selected from the group consisting of $y_{14}$, $n_{15}$, $n_{16}$, $n_{17}$ and $c_{18}$. In certain embodiments, oligonucleotide decoys comprising a deletion of one or more nucleotides selected from the group consisting of $y_{14}$, $n_{15}$, $n_{16}$, $n_{17}$ and $c_{18}$ have at least 80% identity to the nucleotide sequence of SEQ ID NO.: 14.

In certain embodiments, an oligonucleotide decoy comprises a double-stranded sequence represented by formula (15):

$$5'-S_1n_2n_3M_4W_5W_6G_7G_8A_9A_{10}A_{11}A_{12}n_{13}n_{14}d_{15}W_{16}W_{17}g_{18} \quad (15)$$

$$g_{19}a_{20}a_{21}a_{22}a_{23}n_{24}n_{25}d_{26}W_{27}G_{28}G_{29}A_{30}A_{31}A_{32}A_{33}n_{34}$$

$$n_{35}n_{36}n_{37}n_{38}n_{39}S_{40}-3'$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "D" can be a A, G or a T, "W" can be a A or a T, "M" can be C or A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (15) has at least about 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 15. Such oligonucleotide decoys can bind to NFATC1 transcription factor. In certain embodiments, such oligonucleotide decoys can bind to one or more transcription factors closely related to NFATC1 transcription factor, such as NFATC2-4.

In certain embodiments, an oligonucleotide decoy represented by formula (15) comprises a deletion of one or more (e.g., 1, 2, 3, 4, 5, 6, 7, 8, 9, 10, 11, 12, 13, 14 or 15) nucleotides selected from the group consisting of $n_{13}$, $n_{14}$, $d_{15}$, $w_{16}$, $w_{17}$, $g_{18}$, $g_{19}$, $a_{20}$, $a_{21}$, $a_{22}$, $a_{23}$, $n_{24}$, $n_{25}$, $d_{26}$ and $w_{27}$. In certain embodiments, oligonucleotide decoys comprising a deletion of one or more nucleotides selected from the group consisting of $n_{13}$, $n_{14}$, $d_{15}$, $w_{16}$, $w_{17}$, $g_{18}$, $g_{19}$, $a_{20}$, $a_{21}$, $a_{22}$, $a_{23}$, $n_{24}$, $n_{25}$, $d_{26}$ and $w_{27}$ have at least 60% identity to the nucleotide sequence of SEQ ID NO.: 15.

In certain embodiments, an oligonucleotide decoy comprises a double-stranded sequence represented by formula (16):

$$5'-S_1n_2n_3n_4n_5n_6C_7A_8C_9T_{10}T_{11}C_{12}C_{13}Y_{14}V_{15}m_{16}n_{17}n_{18} \quad (16)$$

$$n_{19}y_{20}v_{21}C_{22}T_{23}T_{24}C_{25}C_{26}T_{27}G_{28}C_{29}n_{30}n_{31}n_{32}S_{33}-3'$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "Y" can be T or C, "V" can be G, A or C, "M" can be C or A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (16) has at least about 55%, 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 16. Such oligonucleotide decoys can bind to ELK1 transcription factor. In certain embodiments, such oligonucleotide decoys can bind to one or more transcription factors closely related to ELK1 transcription factor, such as ETS1.

In certain embodiments, an oligonucleotide decoy represented by formula (16) comprises a deletion of one or more (e.g., 1, 2, 3, 4, 5, 6, 7 or 8) nucleotides selected from the group consisting of $y_{14}$, $v_{15}$, $m_{16}$, $n_{17}$, $n_{18}$, $n_{19}$, $y_{20}$ and $v_{21}$. In certain embodiments, oligonucleotide decoys comprising a deletion of one or more nucleotides selected from the group consisting of $y_{14}$, $v_{15}$, $m_{16}$, $n_{17}$, $n_{18}$, $n_{19}$, $y_{20}$ and $v_{21}$ have at least 55% identity to the nucleotide sequence of SEQ ID NO.: 16.

In certain embodiments, an oligonucleotide decoy comprises a double-stranded sequence represented by formula (17):

$$5'-S_1n_2n_3n_4n_5n_6C_7T_8A_9T_{10}A_{11}A_{12}A_{13}T_{14}g_{15}g_{16}c_{17}c_{18} \quad (17)$$

$$t_{19}A_{20}T_{21}A_{22}A_{23}A_{24}T_{25}G_{26}g_{27}g_{28}g_{29}g_{30}g_{31}g_{32}S_{33}-3'$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (17) has at least about 70%, 75%, 80%, 85%, 88%, 90%, 91%, 92%, 93%, 94%, 95%, 96%, 97%, 98%, or 99% sequence identity to the nucleotide sequence of SEQ ID NO.: 17. Such oligonucleotide decoys can bind to ternary complex factors. In certain embodiments, such oligonucleotide decoys can bind to one or more transcription factors closely related to ternary complex factors, such as SRF.

In certain embodiments, an oligonucleotide decoy represented by formula (17) comprises a deletion of one or more (e.g., 1, 2, 3, 4 or 5) nucleotides selected from the group consisting of $g_{15}$, $g_{16}$, $c_{17}$, $c_{18}$ and $t_{19}$. In certain embodiments, oligonucleotide decoys comprising a deletion of one or more nucleotides selected from the group consisting of $g_{15}$, $g_{16}$, $c_{17}$, $c_{18}$ and $t_{19}$ have at least 70% identity to the nucleotide sequence of SEQ ID NO.: 17.

In certain embodiments, an oligonucleotide decoy comprises a double-stranded sequence represented by formula (18):

$$5'-S_1n_2n_3n_4n_5n_6n_7W_8W_9C_{10}G_{11}C_{12}G_{13}G_{14}w_{15}w_{16}g_{17}g_{18} \quad (18)$$

$$w_{19}w_{20}w_{21}C_{22}C_{23}G_{24}G_{25}W_{26}W_{27}n_{28}n_{29}n_{30}n_{31}n_{32}S_{33}-3'$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can a A or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (18) has at least about 90%, 91%, 92%, 93%, 94%, 95%, 96%, 97%, 98%, or 99% sequence identity to the nucleotide sequence of SEQ ID NO.: 18. Such oligonucleotide decoys can bind to STAT1 transcription factor. In certain embodiments, such oligonucleotide decoys can bind to one or more transcription factors closely related to STAT1 transcription factor, such as STAT2-6.

In certain embodiments, an oligonucleotide decoy represented by formula (18) comprises a deletion of one or more (e.g., 1, 2, 3, 4, 5, 6 or 7) nucleotides selected from the group consisting of $w_{15}$, $w_{16}$, $g_{17}$, $g_{18}$, $w_{19}$, $w_{20}$ and $w_{21}$. In certain embodiments, oligonucleotide decoys comprising a deletion of one or more nucleotides selected from the group consisting of $w_{15}$, $w_{16}$, $g_{17}$, $g_{18}$, $w_{19}$, $w_{20}$ and $w_{21}$ have at least 90% identity to the nucleotide sequence of SEQ ID NO.: 18.

In certain embodiments, an oligonucleotide decoy comprises a double-stranded sequence represented by formula (19):

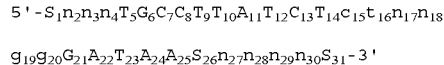

$$5'\text{-}S_1n_2n_3n_4T_5G_6C_7C_8T_9T_{10}A_{11}T_{12}C_{13}T_{14}c_{15}t_{16}n_{17}n_{18}g_{19}g_{20}G_{21}A_{22}T_{23}A_{24}A_{25}S_{26}n_{27}n_{28}n_{29}n_{30}S_{31}\text{-}3' \quad (19)$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (19) has at least about 65%, 70%, 75%, 80%, 85%, 90%, 91%, 92%, 93%, 94%, 95%, 96%, 97%, 98%, or 99% sequence identity to the nucleotide sequence of SEQ ID NO.: 19. Such oligonucleotide decoys can bind to GATA1 transcription factor. In certain embodiments, such oligonucleotide decoys can bind to one or more transcription factors closely related to GATA1 transcription factor, such as GATA2-4.

In certain embodiments, an oligonucleotide decoy represented by formula (19) comprises a deletion of one or more (e.g., 1, 2, 3, 4, 5 or 6) nucleotides selected from the group consisting of $c_{15}$, $t_{16}$, $n_{17}$, $n_{18}$, $g_{19}$ and $g_{20}$. In certain embodiments, oligonucleotide decoys comprising a deletion of one or more nucleotides selected from the group consisting of $c_{15}$, $t_{16}$, $n_{17}$, $n_{18}$, $g_{19}$ and $g_{20}$ have at least 65% identity to the nucleotide sequence of SEQ ID NO.: 19.

In certain embodiments, an oligonucleotide decoy comprises a double-stranded sequence represented by formula (20):

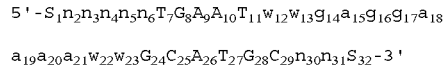

$$5'\text{-}S_1n_2n_3n_4n_5n_6T_7G_8A_9A_{10}T_{11}w_{12}w_{13}g_{14}a_{15}g_{16}g_{17}a_{18}a_{19}a_{20}a_{21}w_{22}w_{23}G_{24}C_{25}A_{26}T_{27}G_{28}C_{29}n_{30}n_{31}S_{32}\text{-}3' \quad (20)$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can a A or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (20) has at least about 65%, 70%, 75%, 80%, 85%, 90%, 91%, 92%, 93%, 94%, 95%, 96%, 97%, 98%, or 99% sequence identity to the nucleotide sequence of SEQ ID NO.: 20. Such oligonucleotide decoys can bind to ELF1 transcription factor. In certain embodiments, such oligonucleotide decoys can bind to one or more transcription factors closely related to ELF1 transcription factor, such as POU1F1.

In certain embodiments, an oligonucleotide decoy represented by formula (20) comprises a deletion of one or more (e.g., 1, 2, 3, 4, 5, 6, 7, 8, 9, 10, 11 or 12) nucleotides selected from the group consisting of $w_{12}$, $w_{13}$, $g_{14}$, $a_{15}$, $g_{16}$, $g_{17}$, $a_{18}$, $a_{19}$, $a_{20}$, $a_{21}$, $w_{22}$ and $w_{23}$. In certain embodiments, oligonucleotide decoys comprising a deletion of one or more nucleotides selected from the group consisting of $w_{12}$, $w_{13}$, $g_{14}$, $a_{15}$, $g_{16}$, $g_{17}$, $a_{18}$, $a_{19}$, $a_{20}$, $a_{21}$, $w_{22}$ and $w_{23}$ have at least 65% identity to the nucleotide sequence of SEQ ID NO.: 20.

In certain embodiments, an oligonucleotide decoy comprises a double-stranded sequence represented by formula (21):

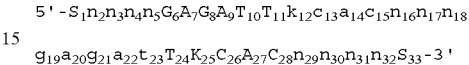

$$5'\text{-}S_1n_2n_3n_4n_5G_6A_7G_8A_9T_{10}T_{11}k_{12}c_{13}a_{14}c_{15}n_{16}n_{17}n_{18}g_{19}a_{20}g_{21}a_{22}t_{23}T_{24}K_{25}C_{26}A_{27}C_{28}n_{29}n_{30}n_{31}n_{32}S_{33}\text{-}3' \quad (21)$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "K" can be a G or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (21) has at least about 60%, 65%, 70%, 75%, 80%, 85%, 90%, 91%, 92%, 93%, 94%, 95%, 96%, 97%, 98%, or 99% sequence identity to the nucleotide sequence of SEQ ID NO.: 21. Such oligonucleotide decoys can bind to "nuclear factor—granulocyte/macrophage a" transcription factors. In certain embodiments, such oligonucleotide decoys can bind to one or more transcription factors closely related to "nuclear factor—granulocyte/macrophage a" transcription factors, such as "nuclear factor—granulocyte/macrophage b-c".

In certain embodiments, an oligonucleotide decoy represented by formula (21) comprises a deletion of one or more (e.g., 1, 2, 3, 4, 5, 6, 7, 8, 9, 10, 11 or 12) nucleotides selected from the group consisting of $k_{12}$, $c_{13}$, $a_{14}$, $c_{15}$, $n_{16}$, $n_{17}$, $n_{18}$, $g_{19}$, $a_{20}$, $g_{21}$, $a_{22}$ and $t_{23}$. In certain embodiments, oligonucleotide decoys comprising a deletion of one or more nucleotides selected from the group consisting of $k_{12}$, $c_{13}$, $a_{14}$, $c_{15}$, $n_{16}$, $n_{17}$, $n_{18}$, $g_{19}$, $a_{20}$, $g_{21}$, $a_{22}$ and $t_{23}$ have at least 60% identity to the nucleotide sequence of SEQ ID NO.: 21.

In certain embodiments, an oligonucleotide decoy comprises a double-stranded sequence represented by formula (22):

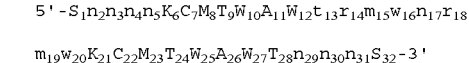

$$5'\text{-}S_1n_2n_3n_4n_5K_6C_7M_8T_9W_{10}A_{11}W_{12}t_{13}r_{14}m_{15}w_{16}n_{17}r_{18}m_{19}w_{20}K_{21}C_{22}M_{23}T_{24}W_{25}A_{26}W_{27}T_{28}n_{29}n_{30}n_{31}S_{32}\text{-}3' \quad (22)$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can a A or a T, "K" can be a G or a T, "M" can be a A or a C, "R" can be a A or a G, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (22) has at least about 65%, 70%, 75%, 80%, 85%, 90%, 91%, 92%, 93%, 94%, 95%, 96%, 97%, 98%, or 99% sequence identity to the nucleotide sequence of SEQ ID NO.: 22. Such oligonucleotide decoys can bind to POU4F1 transcription factor. In certain embodiments, such oligonucleotide decoys can bind to one or more transcription factors closely related to POU4F1 transcription factor, such as POU4F2-3.

In certain embodiments, an oligonucleotide decoy represented by formula (22) comprises a deletion of one or more (e.g., 1, 2, 3, 4, 5, 6, 7 or 8) nucleotides selected from the group consisting of $t_{13}$, $r_{14}$, $m_{15}$, $w_{16}$, $n_{17}$, $r_{18}$, $m_{19}$ and $w_{20}$. In certain embodiments, oligonucleotide decoys comprising a deletion of one or more nucleotides selected from the group consisting of $t_{13}$, $r_{14}$, $m_{15}$, $w_{16}$, $n_{17}$, $r_{18}$, $m_{19}$ and $w_{20}$ have at least 65% identity to the nucleotide sequence of SEQ ID NO.: 22.

In certain embodiments, an oligonucleotide decoy comprises a double-stranded sequence represented by formula (23):

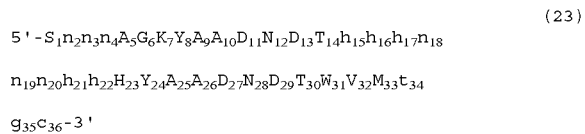

wherein "A" is an adenine nucleotide, "C" is a cytosine nucleotide, "G" is a guanine nucleotide, "T" is a thymine nucleotide, "S" can be a G or C nucleotide, "N" can be any nucleotide, "Y" can be T or C, "V" can be G, A or C, "K" can be T or G, "D" can be G, A or T, "H" can be A, T or C, "W" can be A or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (23) has at least about 55%, 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 23. Such oligonucleotide decoys can bind to HNF1A transcription factor. In certain embodiments, such oligonucleotide decoys can bind to one or more transcription factors closely related to HNF1A transcription factor, such as HNF1B-C.

In certain embodiments, an oligonucleotide decoy represented by formula (23) comprises a deletion of one or more (e.g., 1, 2, 3, 4, 5, 6, 7 or 8) nucleotides selected from the group consisting of $h_{15}$, $h_{16}$, $h_{17}$, $n_{18}$, $n_{19}$, $n_{20}$, $h_{21}$ and $h_{22}$. In certain embodiments, oligonucleotide decoys comprising a deletion of one or more nucleotides selected from the group consisting of $h_{15}$, $h_{16}$, $h_{17}$, $n_{18}$, $n_{19}$, $n_{20}$, $h_{21}$ and $h_{22}$ have at least 55% identity to the nucleotide sequence of SEQ ID NO.: 23.

In certain embodiments, an oligonucleotide decoy comprises a double-stranded sequence represented by formula (24):

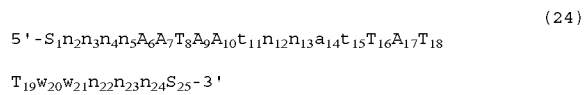

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be a A or a T, lower case letters can optionally be deleted, and the numbers in subscript represent the position of a nucleotide in the sequence. Although the formula shows a single strand, it should be understood that a complementary strand is included as part of the structure.

In preferred embodiments, an oligonucleotide decoy having a sequence represented by formula (24) has at least about 80%, 85%, 90%, 91%, 92%, 93%, 94%, 95%, 96%, 97%, 98%, or 99% sequence identity to the nucleotide sequence of SEQ ID NO.: 24. Such oligonucleotide decoys can bind to ZFHX3 transcription factor. In certain embodiments, such oligonucleotide decoys can bind to one or more transcription factors closely related to ZFHX3 transcription factor, such as ZFHX-2, -4.

In certain embodiments, an oligonucleotide decoy represented by formula (24) comprises a deletion of one or more (e.g., 1, 2, 3, 4 or 5) nucleotides selected from the group consisting of $t_{11}$, $n_{12}$, $n_{13}$, $a_{14}$ and $t_{15}$. In certain embodiments, oligonucleotide decoys comprising a deletion of one or more nucleotides selected from the group consisting of $t_{11}$, $n_{12}$, $n_{13}$, $a_{14}$ and $t_{15}$ have at least 80% identity to the nucleotide sequence of SEQ ID NO.: 24.

In certain embodiments, an oligonucleotide decoy comprises a double-stranded sequence represented by formula (25):

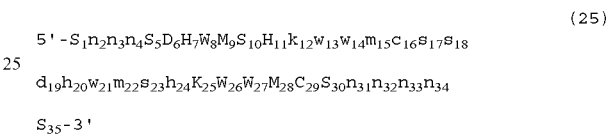

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be a A or T, "D" can be A, G or T, "H" can be A, C or T, "M" can be A or C, "K" can be G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (25) has at least about 80%, 85%, 90%, 91%, 92%, 93%, 94%, 95%, 96%, 97%, 98%, or 99% sequence identity to the nucleotide sequence of SEQ ID NO.: 25. Such oligonucleotide decoys can bind to IRF1 transcription factor. In certain embodiments, such oligonucleotide decoys can bind to one or more transcription factors closely related to IRF1 transcription factor, such as IRF2.

In certain embodiments, an oligonucleotide decoy represented by formula (25) comprises a deletion of one or more (e.g., 1, 2, 3, 4, 5, 6, 7, 8, 9, 10, 11, 12 or 13) nucleotides selected from the group consisting of $k_{12}$, $w_{13}$, $w_{14}$, $m_{15}$, $c_{16}$, $s_{17}$, $s_{18}$, $d_{19}$, $h_{20}$, $w_{21}$, $m_{22}$, $s_{23}$ and $h_{24}$. In certain embodiments, oligonucleotide decoys comprising a deletion of one or more nucleotides selected from the group consisting of $k_{12}$, $w_{13}$, $w_{14}$, $m_{15}$, $c_{16}$, $s_{17}$, $s_{18}$, $d_{19}$, $h_{20}$, $w_{21}$, $m_{22}$, $s_{23}$ and $h_{24}$ have at least 80% identity to the nucleotide sequence of SEQ ID NO.: 25.

In certain embodiments, an oligonucleotide decoy comprises a double-stranded sequence represented by formula (26):

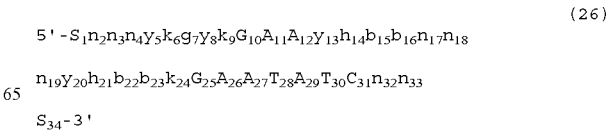

wherein "A" is an adenine nucleotide, "C" is a cytosine nucleotide, "G" is a guanine nucleotide, "T" is a thymine nucleotide, "S" can be a G or C nucleotide, "N" can be any nucleotide, "Y" can be T or C, "V" can be G, A or C, "K" can be T or G, "D" can be G, A or T, "H" can be A, T or G, "B" can be C, G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (26) has at least about 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 26. Such oligonucleotide decoys can bind to TEAD1 transcription factor. In certain embodiments, such oligonucleotide decoys can bind to one or more transcription factors closely related to TEAD1 transcription factor, such as TEAD2-4.

In certain embodiments, an oligonucleotide decoy represented by formula (26) comprises a deletion of one or more (e.g., 1, 2, 3, 4, 5, 6, 7, 8, 9, 10, 11 or 12) nucleotides selected from the group consisting of $y_{13}$, $h_{14}$, $b_{15}$, $b_{16}$, $n_{17}$, $n_{18}$, $n_{19}$, $y_{20}$, $h_{21}$, $b_{22}$, $b_{23}$ and $k_{24}$. In certain embodiments, oligonucleotide decoys comprising a deletion of one or more nucleotides selected from the group consisting of $y_{13}$, $h_{14}$, $b_{15}$, $b_{16}$, $n_{17}$, $n_{18}$, $n_{19}$, $y_{20}$, $h_{21}$, $b_{22}$, $b_{23}$ and $k_{24}$ have at least 60% identity to the nucleotide sequence of SEQ ID NO.: 26.

In certain embodiments, an oligonucleotide decoy comprises a double-stranded sequence represented by formula (27):

$$5'-S_1n_2n_3n_4T_5A_6T_7A_8W_9W_{10}W_{11}n_{12}n_{13}d_{14}n_{15}t_{16}a_{17}t_{18}$$
$$A_{19}W_{20}w_{21}w_{22}n_{23}n_{24}w_{25}W_{26}T_{27}A_{28}A_{29}D_{30}W_{31}n_{32}n_{33}n_{34}$$
$$n_{35}n_{36}S_{37}-3' \quad (27)$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be a A or a T, "D" can be a A, G or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (27) has at least about 75%, 80%, 85%, 90%, 91%, 92%, 93%, 94%, 95%, 96%, 97%, 98%, or 99% sequence identity to the nucleotide sequence of SEQ ID NO.: 27. Such oligonucleotide decoys can bind to TBP transcription factor. In certain embodiments, such oligonucleotide decoys can bind to one or more transcription factors closely related to TBP transcription factor, such as TBPL1-2.

In certain embodiments, an oligonucleotide decoy represented by formula (27) comprises a deletion of one or more (e.g., 1, 2, 3, 4, 5, 6, 7, 8, 9, 10, 11, 12, 13 or 14) nucleotides selected from the group consisting of $w_{10}$, $w_{11}$, $n_{12}$, $n_{13}$, $d_{14}$, $n_{15}$, $t_{16}$, $a_{17}$, $t_{18}$, $w_{21}$, $w_{22}$, $n_{23}$, $n_{24}$, and $w_{25}$. In certain embodiments, oligonucleotide decoys comprising a deletion of one or more nucleotides selected from the group consisting of $w_{10}$, $w_{11}$, $n_{12}$, $n_{13}$, $d_{14}$, $n_{15}$, $t_{16}$, $a_{17}$, $t_{18}$, $w_{21}$, $w_{22}$, $n_{23}$, $n_{24}$, and $w_{25}$ have at least 75% identity to the nucleotide sequence of SEQ ID NO.: 27.

In certain embodiments, an oligonucleotide decoy comprises a double-stranded sequence represented by formula (28):

$$5'-S_1n_2n_3n_4T_5A_6T_7A_8A_9W_{10}W_{11}n_{12}n_{13}n_{14}n_{15}W_{16}W_{17}W_{18}$$
$$A_{19}A_{20}W_{21}W_{22}k_{23}n_{24}n_{25}n_{26}n_{27}n_{28}S_{29}-3' \quad (28)$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be a A or a T, "K" can be a G or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (28) has at least about 65%, 70%, 75%, 80%, 85%, 90%, 91%, 92%, 93%, 94%, 95%, 96%, 97%, 98%, or 99% sequence identity to the nucleotide sequence of SEQ ID NO.: 28. Such oligonucleotide decoys can bind to TBP transcription factors. In certain embodiments, such oligonucleotide decoys can bind to one or more transcription factors closely related to TBP transcription factors, such as TBPL1-2.

In certain embodiments, an oligonucleotide decoy represented by formula (28) comprises a deletion of one or more (e.g., 1, 2, 3, 4, 5, 6 or 7) nucleotides selected from the group consisting of $n_{12}$, $n_{13}$, $n_{14}$, $n_{15}$, $w_{16}$, $w_{17}$ and $w_{18}$. In certain embodiments, oligonucleotide decoys comprising a deletion of one or more nucleotides selected from the group consisting of $n_{12}$, $n_{13}$, $n_{14}$, $n_{15}$, $w_{16}$, $w_{17}$ and $w_{18}$ have at least 65% identity to the nucleotide sequence of SEQ ID NO.: 28.

In certain embodiments, an oligonucleotide decoy comprises a double-stranded sequence represented by formula (29):

$$5'-N_1n_2n_3C_4T_5G_6M_7K_8Y_9K_{10}K_{11}Y_{12}t_{13}m_{14}b_{15}Y_{16}C_{17}A_{18}$$
$$A_{19}T_{20}s_{21}d_{22}n_{23}n_{24}n_{25}S_{26}-3' \quad (29)$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "M" can be a A or a C, "K" can be a G or a T, "Y" can be a C or a T, "B" can be a C, G or T, "D" can be a A, G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (29) has at least about 75%, 80%, 85%, 90%, 91%, 92%, 93%, 94%, 95%, 96%, 97%, 98%, or 99% sequence identity to the nucleotide sequence of SEQ ID NO.: 29. Such oligonucleotide decoys can bind to NFYA transcription factor. In certain embodiments, such oligonucleotide decoys can bind to one or more transcription factors closely related to NFYA transcription factor, such as NFYB-C.

In certain embodiments, an oligonucleotide decoy represented by formula (29) comprises a deletion of one or more (e.g., 1, 2, 3 or 4) nucleotides selected from the group consisting of $t_{13}$, $m_{14}$, $b_{15}$ and $y_{16}$. In certain embodiments, oligonucleotide decoys comprising a deletion of one or more nucleotides selected from the group consisting of $t_{13}$, $m_{14}$, $b_{15}$ and $y_{16}$ have at least 75% identity to the nucleotide sequence of SEQ ID NO.: 29.

In certain embodiments, an oligonucleotide decoy comprises a double-stranded sequence represented by formula (30):

(30)

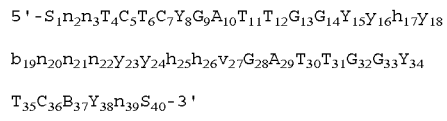

wherein "A" is an adenine nucleotide, "C" is a cytosine nucleotide, "G" is a guanine nucleotide, "T" is a thymine nucleotide, "S" can be a G or C nucleotide, "N" can be any nucleotide, "Y" can be T or C, "H" can be A, T or C, "B" can be C, G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (30) has at least about 50%, 55%, 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 30. Such oligonucleotide decoys can bind to NFYA transcription factor. In certain embodiments, such oligonucleotide decoys can bind to one or more transcription factors closely related to NFYA transcription factor, such as NFYB-C.

In certain embodiments, an oligonucleotide decoy represented by formula (30) comprises a deletion of one or more (e.g., 1, 2, 3, 4, 5, 6, 7, 8, 9, 10, 11 or 12) nucleotides selected from the group consisting of $y_{16}$, $h_{17}$, $y_{18}$, $b_{19}$, $n_{20}$, $n_{21}$, $n_{22}$, $y_{23}$, $y_{24}$, $h_{25}$, $h_{26}$ and $v_{27}$. In certain embodiments, oligonucleotide decoys comprising a deletion of one or more nucleotides selected from the group consisting of $y_{16}$, $h_{17}$, $y_{18}$, $b_{19}$, $n_{20}$, $n_{21}$, $n_{22}$, $y_{23}$, $y_{24}$, $h_{25}$, $h_{26}$ and $v_{27}$ have at least 50% identity to the nucleotide sequence of SEQ ID NO.: 30.

In certain embodiments, an oligonucleotide decoy comprises a double-stranded sequence represented by formula (31):

(31)

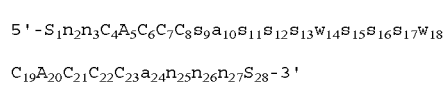

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be a A or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (31) has at least about 75%, 80%, 85%, 90%, 91%, 92%, 93%, 94%, 95%, 96%, 97%, 98%, or 99% sequence identity to the nucleotide sequence of SEQ ID NO.: 31. Such oligonucleotide decoys can bind to CACCC-box binding factors.

In certain embodiments, an oligonucleotide decoy represented by formula (31) comprises a deletion of one or more (e.g., 1, 2, 3, 4, 5, 6, 7, 8, 9 or 10) nucleotides selected from the group consisting of $s_9$, $a_{10}$, $s_{11}$, $s_{12}$, $s_{13}$, $w_{14}$, $s_{15}$, $s_{16}$, $s_{17}$ and $w_{18}$. In certain embodiments, oligonucleotide decoys comprising a deletion of one or more nucleotides selected from the group consisting of $s_9$, $a_{10}$, $s_{11}$, $s_{12}$, $s_{13}$, $w_{14}$, $s_{15}$, $s_{16}$, $s_{17}$ and $w_{18}$ have at least 75% identity to the nucleotide sequence of SEQ ID NO.: 31.

In certain embodiments, an oligonucleotide decoy comprises a double-stranded sequence represented by formula (32):

(32)

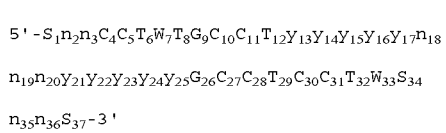

wherein "A" is an adenine nucleotide, "C" is a cytosine nucleotide, "G" is a guanine nucleotide, "T" is a thymine nucleotide, "S" can be a G or C nucleotide, "N" can be any nucleotide, "Y" can be T or C, "W" can be A or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (32) has at least about 50%, 55%, 60%, 65%70%, 75%, 80%, 85%, 88%, 90%, 91%, 92%, 93%, 94%, 95%, 96%, 97%, 98%, or 99% sequence identity to the nucleotide sequence of SEQ ID NO.: 32. Such oligonucleotide decoys can bind to KLF4 transcription factor. In certain embodiments, such oligonucleotide decoys can bind to one or more transcription factors closely related to KLF4 transcription factor, such as KLF-1, -5.

In certain embodiments, an oligonucleotide decoy represented by formula (32) comprises a deletion of one or more (e.g., 1, 2, 3, 4, 5, 6, 7, 8, 9, 10, 11, 12 or 13) nucleotides selected from the group consisting of $y_{13}$, $y_{14}$, $y_{15}$, $y_{16}$, $y_{17}$, $n_{18}$, $n_{19}$, $n_{20}$, $y_{21}$, $y_{22}$, $y_{23}$, $y_{24}$ and $y_{25}$. In certain embodiments, oligonucleotide decoys comprising a deletion of one or more nucleotides selected from the group consisting of $y_{13}$, $y_{14}$, $y_{15}$, $y_{16}$, $y_{17}$, $n_{18}$, $n_{19}$, $n_{20}$, $y_{21}$, $y_{22}$, $y_{23}$, $y_{24}$ and $y_{25}$ have at least 50% identity to the nucleotide sequence of SEQ ID NO.: 32.

In certain embodiments, an oligonucleotide decoy comprises a double-stranded sequence represented by formula (33):

(33)

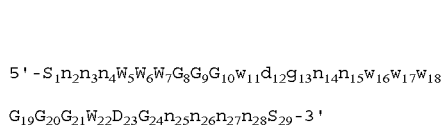

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be a A or a T, "D" can be a A, G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (33) has at least about 75%, 80%, 85%, 90%, 91%, 92%, 93%, 94%, 95%, 96%, 97%, 98%, or 99% sequence identity to the nucleotide sequence of SEQ ID NO.: 33. Such oligonucleotide decoys can bind to KLF7 transcription factor. In certain embodiments, such oligonucleotide decoys can bind to one or more transcription factors closely related to KLF7 transcription factor, such as KLF-1, -2, and -5.

In certain embodiments, an oligonucleotide decoy represented by formula (33) comprises a deletion of one or more (e.g., 1, 2, 3, 4, 5, 6, 7 or 8) nucleotides selected from the group consisting of $w_{11}$, $d_{12}$, $g_{13}$, $n_{14}$, $n_{15}$, $w_{16}$, $w_{17}$ and $w_{18}$. In certain embodiments, oligonucleotide decoys comprising a deletion of one or more nucleotides selected from the group consisting of $w_{11}$, $d_{12}$, $g_{13}$, $n_{14}$, $n_{15}$, $w_{16}$, $w_{17}$ and $w_{18}$ have at least 75% identity to the nucleotide sequence of SEQ ID NO.: 33.

In certain embodiments, an oligonucleotide decoy comprises a double-stranded sequence represented by formula (34):

$$5'-S_1w_2w_3w_4w_5w_6C_7A_8C_9T_{10}C_{11}A_{12}G_{13}C_{14}w_{15}w_{16}w_{17}w_{18}$$
$$c_{19}g_{20}g_{21}w_{22}g_{23}w_{24}G_{25}G_{26}G_{27}W_{28}W_{29}g_{30}W_{31}w_{32}w_{33}w_{34}$$
$$w_{35}S_{36}-3' \tag{34}$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be a A or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (34) has at least about 55%, 60%, 65%, 70%, 75%, 80%, 85%, 90%, 91%, 92%, 93%, 94%, 95%, 96%, 97%, 98%, or 99% sequence identity to the nucleotide sequence of SEQ ID NO.: 34. Such oligonucleotide decoys can bind to MAFG transcription factor. In certain embodiments, such oligonucleotide decoys can bind to one or more transcription factors closely related to MAFG transcription factor, such as MAF-A, -B, -F, -K.

In certain embodiments, an oligonucleotide decoy represented by formula (34) comprises a deletion of one or more (e.g., 1, 2, 3, 4, 5, 6, 7, 8, 9 or 10) nucleotides selected from the group consisting of $w_{15}$, $w_{16}$, $w_{17}$, $w_{18}$, $c_{19}$, $g_{20}$, $g_{21}$, $w_{22}$, $g_{23}$ and $w_{24}$. In certain embodiments, oligonucleotide decoys comprising a deletion of one or more nucleotides selected from the group consisting of $w_{15}$, $w_{16}$, $w_{17}$, $w_{18}$, $c_{19}$, $g_{20}$, $g_{21}$, $w_{22}$, $g_{23}$ and $w_{24}$ have at least 55% identity to the nucleotide sequence of SEQ ID NO.: 34.

In certain embodiments, an oligonucleotide decoy comprises a double-stranded sequence represented by formula (35):

$$5'-S_1n_2n_3W_4B_5Y_6A_7G_8Y_9A_{10}C_{11}C_{12}D_{13}N_{14}R_{15}G_{16}H_{17}S_{18}$$
$$A_{19}G_{20}C_{21}N_{22}N_{23}H_{24}n_{25}n_{26}n_{27}W_{28}B_{29}Y_{30}A_{31}G_{32}Y_{33}A_{34}$$
$$C_{35}C_{36}D_{37}N_{38}R_{39}G_{40}H_{41}S_{42}A_{43}G_{44}C_{45}N_{46}N_{47}H_{48}n_{49}n_{50}$$
$$S_{51}-3' \tag{35}$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be a A or a T, Y can be a C or a T, "H" can be a A, T or a C, "R" can be G or A, "D" can be G, A or T, "Y" can be C or T, "B" can be C, G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (35) has at least about 50%, 55%, 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 35. Such oligonucleotide decoys can bind to REST transcription factor.

In certain embodiments, an oligonucleotide decoy represented by formula (35) comprises a deletion of one or more (e.g., 1, 2 or 3) nucleotides selected from the group consisting of $n_{25}$, $n_{26}$ and $n_{27}$. In certain embodiments, oligonucleotide decoys comprising a deletion of one or more nucleotides selected from the group consisting of $n_{25}$, $n_{26}$ and $n_{27}$ have at least 50% identity to the nucleotide sequence of SEQ ID NO.: 35.

In certain embodiments, an oligonucleotide decoy comprises a double-stranded sequence represented by formula (36):

$$5'-S_1n_2n_3n_4n_5G_6A_7R_8M_9A_{10}W_{11}k_{12}s_{13}a_{14}g_{15}k_{16}n_{17}n_{18}$$
$$n_{19}n_{20}g_{21}a_{22}r_{23}m_{24}A_{25}W_{26}K_{27}S_{28}A_{29}G_{30}K_{31}n_{32}n_{33}n_{34}$$
$$n_{35}S_{36}-3' \tag{36}$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be a A or a T, "M" can be A or C, "R" can be A or G, "K" can be G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (36) has at least about 60%, 65%, 70%, 75%, 80%, 85%, 90%, 91%, 92%, 93%, 94%, 95%, 96%, 97%, 98%, or 99% sequence identity to the nucleotide sequence of SEQ ID NO.: 36. Such oligonucleotide decoys can bind to KCNIP3 transcription factor.

In certain embodiments, an oligonucleotide decoy represented by formula (36) comprises a deletion of one or more (e.g., 1, 2, 3, 4, 5, 6, 7, 8, 9, 10, 11, 12 or 13) nucleotides selected from the group consisting of $k_{12}$, $s_{13}$, $a_{14}$, $g_{15}$, $k_{16}$, $n_{17}$, $n_{18}$, $n_{19}$, $n_{20}$, $g_{21}$, $a_{22}$, $r_{23}$ and $m_{24}$. In certain embodiments, oligonucleotide decoys comprising a deletion of one or more nucleotides selected from the group consisting of $k_{12}$, $s_{13}$, $a_{14}$, $g_{15}$, $k_{16}$, $n_{17}$, $n_{18}$, $n_{19}$, $n_{20}$, $g_{21}$, $a_{22}$, $r_{23}$ and $m_{24}$ have at least 60% identity to the nucleotide sequence of SEQ ID NO.: 36.

In certain embodiments, an oligonucleotide decoy comprises a double-stranded sequence represented by formula (37):

$$5'-S_1n_2n_3n_4n_5G_6A_7R_8G_9C_{10}C_{11}S_{12}s_{13}W_{14}g_{15}W_{16}n_{17}n_{18}$$
$$n_{19}n_{20}g_{21}a_{22}r_{23}G_{24}C_{25}C_{26}S_{27}S_{28}W_{29}G_{30}W_{31}n_{32}n_{33}$$
$$n_{34}S_{35}-3' \tag{37}$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be a A or a T, "M" can be A or C, "R" can be A or G, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (37) has at least about 75%, 80%, 85%, 90%, 91%, 92%, 93%, 94%, 95%, 96%, 97%, 98%, or 99% sequence identity to the nucleotide sequence of SEQ ID NO.: 37. Such oligonucleotide decoys can bind to KCNIP3 transcription factor.

In certain embodiments, an oligonucleotide decoy represented by formula (37) comprises a deletion of one or more (e.g., 1, 2, 3, 4, 5, 6, 7, 8, 9, 10 or 11) nucleotides selected from the group consisting of $s_{13}$, $w_{14}$, $g_{15}$, $w_{16}$, $n_{17}$, $n_{18}$, $n_{19}$, $n_{20}$, $g_{21}$, $a_{22}$ and $r_{23}$. In certain embodiments, oligonucleotide decoys comprising a deletion of one or more nucleotides selected from the group consisting of $s_{13}$, $w_{14}$, $g_{15}$, $w_{16}$, $n_{17}$, $n_{18}$, $n_1$, $n_{20}$, $g_{21}$, $a_{22}$ and $r_{23}$ have at least 75% identity to the nucleotide sequence of SEQ ID NO.: 37.

In certain embodiments, an oligonucleotide decoy comprises a double-stranded sequence represented by formula (38):

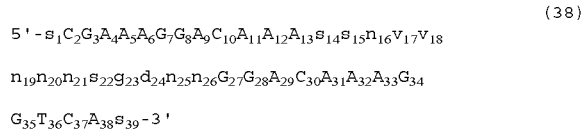

(38)
5'-$s_1C_2G_3A_4A_5A_6G_7G_8A_9C_{10}A_{11}A_{12}A_{13}s_{14}s_{15}n_{16}v_{17}v_{18}$
$n_{19}n_{20}n_{21}s_{22}g_{23}d_{24}n_{25}n_{26}G_{27}G_{28}A_{29}C_{30}A_{31}A_{32}A_{33}G_{34}$
$G_{35}T_{36}C_{37}A_{38}s_{39}$-3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "V" can be A, C or G, "D" can be G, A or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (38) has at least about 50%, 55%, 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 38. Such oligonucleotide decoys can bind to PPARA transcription factor. In certain embodiments, such oligonucleotide decoys can bind to one or more transcription factors closely related to PPARA transcription factor, such as PPAR-D, -G.

In certain embodiments, an oligonucleotide decoy represented by formula (38) comprises a deletion of one or more (e.g., 1, 2, 3, 4, 5, 6, 7, 8, 9 or 10) nucleotides selected from the group consisting of $s_{14}$, $s_{15}$, $n_{16}$, $v_{17}$, $v_{18}$, $n_{19}$, $n_{20}$, $n_{21}$, $s_{22}$ and $g_{23}$. In certain embodiments, oligonucleotide decoys comprising a deletion of one or more nucleotides selected from the group consisting of $s_{14}$, $s_{15}$, $n_{16}$, $v_{17}$, $v_{18}$, $n_{19}$, $n_{20}$, $n_{21}$, $s_{22}$ and $g_{23}$ have at least 50% identity to the nucleotide sequence of SEQ ID NO.: 38.

In certain embodiments, an oligonucleotide decoy comprises a double-stranded sequence represented by formula (39):

(39)
5'-$s_1n_2n_3n_4A_5R_6M_7R_8W_9W_{10}Y_{11}w_{12}m_{13}g_{14}n_{15}n_{16}a_{17}r_{18}$
$m_{19}r_{20}w_{21}w_{22}y_{23}W_{24}M_{25}G_{26}A_{27}A_{28}T_{29}T_{30}n_{31}n_{32}n_{33}$
$n_{34}s_{35}$-3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be a A or a T, "R" can be A or G, "M" can be a A or a C, "Y" can be a C or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (39) has at least about 55%, 60%, 65%, 70%, 75%, 80%, 85%, 90%, 91%, 92%, 93%, 94%, 95%, 96%, 97%, 98%, or 99% sequence identity to the nucleotide sequence of SEQ ID NO.: 39. Such oligonucleotide decoys can bind to HSF1 transcription factor. In certain embodiments, the oligonucleotide decoys can bind to one or more transcription factors closely related to HSF1 transcription factor, such as HSF2.

In certain embodiments, an oligonucleotide decoy represented by formula (39) comprises a deletion of one or more (e.g., 1, 2, 3, 4, 5, 6, 7, 8, 9, 10, 11, 12 or 13) nucleotides selected from the group consisting of $y_{11}$, $w_{12}$, $m_{13}$, $g_{14}$, $n_{15}$, $n_{16}$, $a_{17}$, $r_{18}$, $m_{19}$, $r_{20}$, $w_{21}$, $w_{22}$ and $y_{23}$. In certain embodiments, oligonucleotide decoys comprising a deletion of one or more nucleotides selected from the group consisting of $y_{11}$, $w_{1,2}$ $m_{13}$, $g_{14}$, $n_{15}$, $n_{16}$, $a_{17}$, $r_{18}$, $m_{19}$, $r_{20}$, $w_{21}$, $w_{22}$ and $y_{23}$ have at least 55% identity to the nucleotide sequence of SEQ ID NO.: 39.

In certain embodiments, an oligonucleotide decoy comprises a double-stranded sequence represented by formula (47):

(47)
5'-$s_1n_2n_3n_4n_5n_6C_7A_8C_9T_{10}T_{11}C_{12}C_{13}T_{14}G_{15}C_{16}n_{17}n_{18}$
$n_{19}n_{20}n_{21}s_{22}$-3' wherein "A" is an adenine nucleotide, "C" is a cytosine nucleotide, "G" is a guanine nucleotide, "T" is a thymine nucleotide, "S" can be a G or C nucleotide, "N" can be any nucleotide, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (47) has at least about 80%, 85%, 88%, 90%, 91%, 92%, 93%, 94%, 95%, 96%, 97%, 98%, or 99% sequence identity to the nucleotide sequence of SEQ ID NO.: 47. Such oligonucleotide decoys can bind to ELK1 transcription factor. In certain embodiments, such oligonucleotide decoys can bind to one or more transcription factors closely related to ELK1 transcription factor, such as ETS1.

In certain embodiments, an oligonucleotide decoy represented by formula (47) comprises a deletion of one or more (e.g., 1, 2, 3, 4, 5, 6, 7, 8, 9 or 10) nucleotides selected from the group consisting of $n_2$, $n_3$, $n_4$, $n_5$, $n_6$, $n_{17}$, $n_{18}$, $n_{19}$, $n_{20}$ and $n_{21}$. In certain embodiments, oligonucleotide decoys comprising a deletion of one or more nucleotides selected from the group consisting of $n_2$, $n_3$, $n_4$, $n_5$, $n_6$, $n_{17}$, $n_{18}$, $n_{19}$, $n_{20}$ and $n_{21}$ have at least 80% identity to the nucleotide sequence of SEQ ID NO.: 47.

In certain embodiments, an oligonucleotide decoy comprises a double-stranded sequence represented by formula (48):

$$5'-S_1n_2n_3n_4n_5n_6A_7G_8K_9Y_{10}A_{11}A_{12}D_{13}N_{14}D_{15}T_{16}W_{17}V_{18}M_{19}N_{20}n_{21}n_{22}n_{23}n_{24}n_{25}S_{26}-3' \quad (48)$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "Y" can be T or C, "V" can be G, A or C, "K" can be T or G, "D" can be G, A or T, "W" can be A or T, "M" can be C or A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (48) has at least about 70%, 75%, 80%, 85%, 88%, 90%, 91%, 92%, 93%, 94%, 95%, 96%, 97%, 98%, or 99% sequence identity to the nucleotide sequence of SEQ ID NO.: 48. Such oligonucleotide decoys can bind to HNF1A transcription factor. In certain embodiments, such oligonucleotide decoys can bind to one or more transcription factors closely related to HNF1A transcription factor, such as HNF1B-C.

In certain embodiments, an oligonucleotide decoy represented by formula (48) comprises a deletion of one or more (e.g., 1, 2, 3, 4, 5, 6, 7, 8, 9 or 10) nucleotides selected from the group consisting of $n_2$, $n_3$, $n_4$, $n_5$, $n_6$, $n_{21}$, $n_{22}$, $n_{23}$, $n_{24}$ and $n_{25}$. In certain embodiments, oligonucleotide decoys comprising a deletion of one or more nucleotides selected from the group consisting of $n_2$, $n_3$, $n_4$, $n_5$, $n_6$, $n_{21}$, $n_{22}$, $n_{23}$, $n_{24}$ and $n_{25}$ have at least 70% identity to the nucleotide sequence of SEQ ID NO.: 48.

In certain embodiments, an oligonucleotide decoy comprises a double-stranded sequence represented by formula (49):

$$5'-S_1n_2n_3T_4C_5T_6C_7Y_8G_9A_{10}T_{11}T_{12}G_{13}G_{14}Y_{15}T_{16}C_{17}B_{18}Y_{19}n_{20}S_{21}-3' \quad (49)$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "Y" can be T or C, "B" can be C, G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (49) has at least about 80%, 85%, 88%, 90%, 91%, 92%, 93%, 94%, 95%, 96%, 97%, 98%, or 99% sequence identity to the nucleotide sequence of SEQ ID NO.: 49. Such oligonucleotide decoys can bind to NFYA transcription factor. In certain embodiments, such oligonucleotide decoys can bind to one or more transcription factors closely related to NFYA transcription factor, such as NFYB-C.

In certain embodiments, an oligonucleotide decoy represented by formula (49) comprises a deletion of one or more (e.g., 1, 2 or 3) nucleotides selected from the group consisting of $n_2$, $n_3$ and $n_{20}$. In certain embodiments, oligonucleotide decoys comprising a deletion of one or more nucleotides selected from the group consisting of $n_2$, $n_3$ and $n_{20}$ have at least 80% identity to the nucleotide sequence of SEQ ID NO.: 49.

In certain embodiments, an oligonucleotide decoy comprises a double-stranded sequence represented by formula (50):

$$5'-S_1n_2n_3n_4n_5n_6C_7C_8T_9W_{10}T_{11}G_{12}C_{13}C_{14}T_{15}C_{16}C_{17}T_{18}W_{19}S_{20}r_{21}r_{22}n_{23}n_{24}n_{25}S_{26}-3' \quad (50)$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be A or T, "R" can be G or A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (50) has at least about 75%, 80%, 85%, 88%, 90%, 91%, 92%, 93%, 94%, 95%, 96%, 97%, 98%, or 99% sequence identity to the nucleotide sequence of SEQ ID NO.: 50. Such oligonucleotide decoys can bind to KLF4 transcription factor. In certain embodiments, such oligonucleotide decoys can bind to one or more transcription factors closely related to KLF4 transcription factor, such as KLF-1, -5.

In certain embodiments, an oligonucleotide decoy represented by formula (50) comprises a deletion of one or more (e.g., 1, 2, 3, 4, 5, 6, 7, 8, 9 or 10) nucleotides selected from the group consisting of $n_2$, $n_3$, $n_4$, $n_5$, $n_6$, $r_{21}$, $r_{22}$, $n_{23}$, $n_{24}$ and $n_{25}$. In certain embodiments, oligonucleotide decoys comprising a deletion of one or more nucleotides selected from the group consisting of $n_2$, $n_3$, $n_4$, $n_5$, $n_6$, $r_{21}$, $r_{22}$, $n_{23}$, $n_{24}$ and $n_{25}$ have at least 75% identity to the nucleotide sequence of SEQ ID NO.: 50.

In certain embodiments, an oligonucleotide decoy comprises a double-stranded sequence represented by formula (51):

$$5'-S_1n_2n_3n_4n_5W_6B_7Y_8A_9G_{10}Y_{11}A_{12}C_{13}C_{14}D_{15}N_{16}R_{17}G_{18}H_{19}S_{20}A_{21}G_{22}C_{23}N_{24}N_{25}H_{26}n_{27}n_{28}n_{29}n_{30}S_{31}-3' \quad (51)$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be a A or a T, "H" can be a A, T or a C, "R" can be G or A, "D" can be G, A or T, "Y" can be C or T, "B" can be C, G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (51) has at least about 75%, 80%, 85%, 88%, 90%, 91%, 92%, 93%, 94%, 95%, 96%, 97%, 98%, or 99% sequence identity to the nucleotide sequence of SEQ ID NO.: 51. Such oligonucleotide decoys can bind to REST transcription factor.

In certain embodiments, an oligonucleotide decoy represented by formula (51) comprises a deletion of one or more (e.g., 1, 2, 3, 4, 5, 6, 7 or 8) nucleotides selected from the group consisting of $n_2$, $n_3$, $n_4$, $n_5$, $n_{27}$, $n_{28}$, $n_{29}$ and $n_{30}$. In certain embodiments, oligonucleotide decoys comprising a deletion of one or more nucleotides selected from the group consisting of $n_2$, $n_3$, $n_4$, $n_5$, $n_{27}$, $n_{28}$, $n_{29}$ and $n_{30}$ have at least 75% identity to the nucleotide sequence of SEQ ID NO.: 51.

In certain embodiments, an oligonucleotide decoy comprises a double-stranded sequence represented by formula (52):

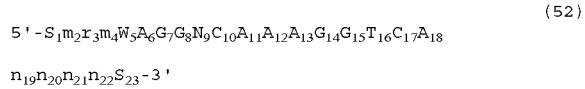

(52)

5'-$S_1 m_2 r_3 m_4 W_5 A_6 G_7 G_8 N_9 C_{10} A_{11} A_{12} A_{13} G_{14} G_{15} T_{16} C_{17} A_{18}$
$n_{19} n_{20} n_{21} n_{22} S_{23}$-3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be A or T, "R" can be G or A, "M" can be C or A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (52) has at least about 80%, 85%, 88%, 90%, 91%, 92%, 93%, 94%, 95%, 96%, 97%, 98%, or 99% sequence identity to the nucleotide sequence of SEQ ID NO.: 52. Such oligonucleotide decoys can bind to PPARA transcription factor. In certain embodiments, such oligonucleotide decoys can bind to one or more transcription factors closely related to PPARA transcription factor, such as PPAR-D, -G.

In certain embodiments, an oligonucleotide decoy represented by formula (52) comprises a deletion of one or more (e.g., 1, 2, 3, 4, 5, 6, 7 or 8) nucleotides selected from the group consisting of $m_2$, $r_3$, $m_4$, $n_{19}$, $n_{20}$, $n_{21}$, $n_{22}$ and $g_{23}$. In certain embodiments, oligonucleotide decoys comprising a deletion of one or more nucleotides selected from the group consisting of $m_2$, $r_3$, $m_4$, $n_{19}$, $n_{20}$, $n_{21}$, $n_{22}$ and $g_{23h}$ have at least 80% identity to the nucleotide sequence of SEQ ID NO.: 52.

In certain embodiments, an oligonucleotide decoy comprises a double-stranded sequence represented by formula (53):

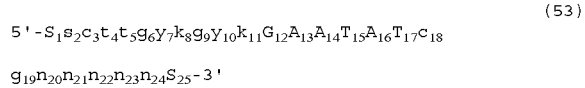

(53)

5'-$S_1 s_2 c_3 t_4 t_5 g_6 y_7 k_8 g_9 y_{10} k_{11} G_{12} A_{13} A_{14} T_{15} A_{16} T_{17} C_{18}$
$g_{19} n_{20} n_{21} n_{22} n_{23} n_{24} S_{25}$-3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "Y" can be T or C, "K" can be T or G, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (53) has at least about 75%, 80%, 85%, 88%, 90%, 91%, 92%, 93%, 94%, 95%, 96%, 97%, 98%, or 99% sequence identity to the nucleotide sequence of SEQ ID NO.: 53. Such oligonucleotide decoys can bind to TEAD1 transcription factor. In certain embodiments, such oligonucleotide decoys can bind to one or more transcription factors closely related to TEAD1 transcription factor, such as TEAD2-4.

In certain embodiments, an oligonucleotide decoy represented by formula (53) comprises a deletion of one or more (e.g., 1, 2, 3, 4, 5, 6, 7, 8, 9, 10, 11, 12, 13, 14, 15, 16 or 17) nucleotides selected from the group consisting of $s_2$, $c_3$, $t_4$, $t_5$, $g_6$, $y_7$, $k_8$, $g_9$, $y_{10}$, $k_{11}$, $c_{18}$, $g_{19}$, $n_{20}$, $n_{21}$, $n_{22}$, $n_{23}$ and $n_{24}$. In certain embodiments, oligonucleotide decoys comprising a deletion of one or more nucleotides selected from the group consisting of $s_2$, $c_3$, $t_4$, $t_5$, $g_6$, $y_7$, $k_8$, $g_9$, $y_{10}$, $k_{11}$, $c_{18}$, $g_{19}$, $n_{20}$, $n_{21}$, $n_{22}$, $n_{23}$ and $n_{24}$ have at least 75% identity to the nucleotide sequence of SEQ ID NO.: 53.

A double stranded oligonucleotide having a certain percent (e.g., 65%, 70%, 75%, 80%, 85%, 90%, 95%, or 99%) of sequence identity with another sequence means that, when aligned, that percentage determines the level of correspondence of bases arrangement in comparing the two sequences. This alignment and the percent homology or identity can be determined using any suitable software program known in the art that allows local alignment. The software program should be capable of finding regions of local identity between two sequences without the need to include the entire length of the sequences. In some embodiments, such program includes but is not limited to the EMBOSS Pairwise Alignment Algorithm (available from the European Bioinformatics Institute (EBI)), the ClustalW program (also available from the European Bioinformatics Institute (EBI)), or the BLAST program (BLAST Manual, Altschul et al., Natl Cent. Biotechnol. Inf., Natl Lib. Med. (NCIB NLM NIH), Bethesda, Md., and Altschul et al., (1997) NAR 25:3389 3402).

One skilled in the art will recognize that sequences encompassed by the invention include those that hybridize under stringent hybridization conditions with an exemplified sequence (e.g., SEQ ID NOs.: 1-42, 45, and 47-53). A nucleic acid is hybridizable to another nucleic acid when a single stranded form of the nucleic acid can anneal to the other single stranded nucleic acid under appropriate conditions of temperature and solution ionic strength. Hybridization conditions are well known in the art. In some embodiments, annealing may occur during a slow decrease of temperature from a denaturing temperature (e.g., 100° C.) to room temperature in a salt containing solvent (e.g., Tris-EDTA buffer).

Generally, the oligonucleotide decoys disclosed herein may be used to bind and, e.g., thereby inhibit, transcription factors that modulate the expression of genes involved nociceptive signaling and/or a subject's (e.g., patient's) perception of pain. A oligonucleotide decoy disclosed herein designed to bind to a specific transcription factor has a nucleic acid sequence mimicking the endogenous genomics DNA sequence normally bound by the transcription factor. Accordingly, the oligonucleotide decoys disclosed herein inhibit a necessary step for gene expression. Further, the oligonucleotide decoys disclosed herein may bind to a number of different transcription factors.

The oligonucleotide decoys disclosed herein may be chemically modified by methods well known to the skilled artisan (e.g., incorporation of phosphorothioate, methylphosphonate, phosphorodithioate, phosphoramidates, carbonate, thioether, siloxane, acetamidate or carboxymethyl ester linkages between nucleotides) to prevent degradation by nucleases within cells and extra-cellular fluids (e.g., serum, cerebrospinal fluid). Also, oligonucleotide decoys may be designed that form hairpin and dumbbell structures which also prevent or hinder nuclease degradation. Further, the oligonucleotide decoys may also be inserted as a portion of a larger plasmid capable of episomal maintenance or constitutive replication in the target cell in order to provide longer term, enhanced intracellular exposure to the decoy sequence and/or reduce its degradation. Accordingly, any chemical modification or structural alteration known in the art to enhance oligonucleotide stability is within the scope of the present disclosure. In some embodiments, the oligonucleotide decoys disclosed herein may be attached, for example, to polyethylene glycol polymers, peptides (e.g., a protein translocation domain) or proteins which improve the therapeutic effect of oligonucleotide decoys. Such modified oligonucleotide decoys may preferentially traverse the cell membrane.

In certain embodiments, the oligonucleotide decoys are provided as salts, hydrates, solvates, or N-oxide derivatives. In certain embodiments, the oligonucleotide decoys are provided in solution (e.g., a saline solution having a physiologic pH) or in lyophilized form. In other embodiments, the oligonucleotide decoys are provided in liposomes.

In certain embodiments, one or more oligonucleotide decoys are provided in a kit. In certain embodiments, the kit includes an instruction, e.g., for using said one or more oligonucleotide decoys. In certain embodiments, said instruction describes one or more of the methods of the present invention, e.g., a method for preventing or treating pain, a method of modulating gene expression in a cell, a method for modulating nociceptive signaling in a cell, a method for modulating protein degradation in a cell, etc. In certain embodiments, the oligonucleotide decoys provided in a kit are provided in lyophilized form. In certain related embodiments, a kit that comprises one or more lyophilized oligonucleotide decoys further comprises a solution (e.g., a pharmaceutically acceptable saline solution) that can be used to resuspend said one or more of the oligonucleotide decoys.

The double stranded oligonucleotides described herein may be made by conventional methods known in the art and thus are well within the ambit of the skilled artisan.

Pharmaceutical Compositions

The pharmaceutical compositions disclosed herein comprise a therapeutically effective amount of one or more oligonucleotide decoys, preferably, in purified form, together with a suitable amount of a pharmaceutically acceptable vehicle, so as to provide a form for proper administration to a patient. When administered to a patient, oligonucleotide decoys and pharmaceutically acceptable vehicles are preferably sterile. Water is a preferred vehicle when oligonucleotide decoys are administered intravenously. Saline solutions and aqueous dextrose and glycerol solutions can also be employed as liquid vehicles, particularly for injectable solutions. Suitable pharmaceutical vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds disclosed herein into preparations which can be used pharmaceutically. Proper formulation is dependent upon the route of administration chosen.

The present pharmaceutical compositions can take the form of solutions, suspensions, emulsions, tablets, pills, pellets, capsules, capsules containing liquids, powders, sustained-release formulations, suppositories, aerosols, sprays, suspensions, or any other form suitable for use. Other examples of suitable pharmaceutical vehicles have been described in the art (see Remington's Pharmaceutical Sciences, Philadelphia College of Pharmacy and Science, 19th Edition, 1995).

Pharmaceutical compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, when in tablet or pill form, the compositions may be coated to delay disintegration and absorption in the gastrointestinal tract, thereby providing a sustained action over an extended period of time. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol), oils, alcohols, slightly acidic buffers between pH 4 and pH 6 (e.g., acetate, citrate, or ascorbate at between about 5 mM to about 50 mM), etc. Additionally, flavoring agents, preservatives, coloring agents, bile salts, acylcarnitines and the like may be added.

Compositions for administration via other routes may also be contemplated. For buccal administration, the compositions may take the form of tablets, lozenges, etc., formulated in conventional manner. Liquid drug formulations suitable for use with nebulizers and liquid spray devices and EHD aerosol devices will typically include a compound with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611). A compound may also be formulated in rectal or vaginal compositions such as suppositories or retention enemas, e.g., containing conventional suppository bases such as cocoa butter or other glycerides. In addition to the formulations described previously, a compound may also be formulated as a depot preparation. Such long acting formulations may be administered by implantation (for example, subcutaneously or intramuscularly) or by intramuscular injection. Thus, for example, a compound may be formulated with suitable polymeric or hydrophobic materials (for example, as an emulsion in an acceptable oil) or ion exchange resins, or as sparingly soluble derivatives, for example, as a sparingly soluble salt.

An oligonucleotide decoy may be included in any of the above-described formulations, or in any other suitable formulation, as a pharmaceutically acceptable salt, a solvate or hydrate. Pharmaceutically acceptable salts substantially retain the activity of the parent compound and may be prepared by reaction with appropriate bases or acids and tend to be more soluble in aqueous and other protic solvents than the corresponding parent form.

Therapeutic Uses

In certain embodiments, an oligonucleotide decoy and/or pharmaceutical composition thereof is administered to a patient, such as an animal (e.g., a bird, mammal, primate, or human), suffering from pain including, but not limited to, mechanical pain (e.g., mechanical hyperalgesia and/or allodynia), chemical pain, temperature pain, chronic pain, subchronic pain, acute pain, sub-acute pain, inflammatory pain, neuropathic pain, muscular pain, skeletal pain, post-surgery pain, arthritis pain, and diabetes pain. Further, in certain embodiments, the oligonucleotide decoys and/or pharmaceutical compositions thereof are administered to a patient, such as an animal, as a preventative measure against pain including, but not limited to, post-operative pain, chronic pain, inflammatory pain, neuropathic pain, muscular pain, and skeletal pain. In certain embodiments, the oligonucleotide decoys and/or pharmaceutical compositions thereof may be used for the prevention of one facet of pain while concurrently treating another symptom of pain.

Thus, in certain embodiments, the invention provides methods of treating pain in a patient comprising administering to a patient suffering from pain a therapeutically effective amount of an oligonucleotide decoy described herein. In related embodiments, methods of preventing pain in a patient are provided. Such methods comprise administering to a patient in need thereof (e.g., a patient likely to develop pain, e.g., post-operative pain) a therapeutically effective amount of an oligonucleotide decoy described herein. In certain embodiments, the oligonucleotide decoy is administered perineurally, epidurally/peridurally, intrathecally, or intradermally.

In certain embodiments, the invention provides methods for treating or preventing pain in a patient comprising administering to a patient in need thereof a therapeutically effective amount of an oligonucleotide decoy, wherein the oligonucleotide decoy does not bind to the transcription factors AP1, ETS1 and STAT. In other embodiments, the invention provides methods for treating or preventing pain in a patient comprising administering to the patient in need thereof a therapeutically effective amount of one or more oligonucleotide decoys, wherein the oligonucleotide decoys bind to one or more transcription factors selected from the group consisting of AP1, ETS1, GATA and STAT transcription factors, provided that the pain is not lower back pain due to an intervertebral disc disorder.

In certain embodiments, the invention provides methods for modulating transcription of a gene present in a cell involved in nociceptive signaling and/or the perception of pain in a patient. In certain embodiments, modulation comprises suppressing or repressing gene expression. In other embodiments, modulation comprises stabilizing gene expression. In still other embodiments, modulation comprises activating or inducing gene expression. In certain embodiments, the gene is involved in nociceptive signaling. Genes involved in nociceptive signaling include, but are not limited to, genes encoding membrane proteins (e.g., ion channels, membrane receptors, etc.), soluble signaling molecules (e.g., intracellular signaling molecules or neurotransmitters), synthetic enzymes (e.g., neurotransmitter synthesis enzymes), and transcription factors. Specific examples of such genes include, but are not limited to, BDKRB2, HTR3A, SCN9A, BDNF, GRM5, NOS1, GCH1, CDK5R1, CACNA1B, P2XR3 and PNMT.

In other embodiments, the invention provides methods for modulating nociceptive signaling in a cell. In certain embodiments, modulation comprises suppressing or repressing nociceptive signaling. In certain embodiments, modulating nociceptive signaling in a cell comprises modulating, e.g., increasing, proteolysis of a protein involved in nociceptive signaling in said cell. For instance, abnormally high proteasome activity has been linked to strong deficits of neuronal plasticity (i.e., a major cellular feature of pain). EGR1 is known to repress the expression of selected proteasome factors, thus limiting EGR1-dependent nociceptive signaling activity is relevant for treating pain. Further, neutrophines activate specific receptors in pain neurons that trigger nociceptive signalings. USF factors activate the expression of CGRP and Substance P, two major neurotrophins capable of inducing pain. Inhibiting USF factors is a potential approach to inhibit nociceptive signaling. In certain embodiments, modulation comprises activation of an inhibitor of nociceptive signaling.

In still other embodiments, the invention provided methods for modulating, e.g., increasing, proteolytic degradation of a protein involved in nociceptive signaling in a cell. In certain embodiments, modulation of protein degradation comprises stimulating proteosome function. In certain embodiments, the protein is involved in nociceptive signaling. Proteins involved in nociceptive signaling include, but are not limited to membrane proteins (e.g., ion channels, membrane receptors, etc.), soluble signaling molecules (e.g., intracellular signaling molecules or neurotransmitters), synthetic enzymes (e.g., neurotransmitter synthesis enzymes), and transcription factors. Specific examples of such proteins include, but are not limited to, BDKRB2, HTR3A, SCN9A, BDNF, GRM5, NOS1, GCH1, CDK5R1, CACNA1B, P2XR3 and PNMT.

In certain embodiments, the cell of the various methods is provided in vivo (e.g., in a patient suffering from pain or likely to suffer from pain). A cell provided in vivo can be located in different locations including, but not limited to, a dorsal root ganglia and/or the spinal cord. In other embodiments, the cell of the various methods is provided in vitro (e.g., in a petri dish). The cell can be any cell involved in nociceptive signaling, including, but not limited to, a neuron (e.g., a pain neuron from dorsal root ganglia and/or the spinal cord or from the sympathetic nervous system), a glial cell, a tissue supportive cell (e.g., fibroblast), an immune cell, or a cell from a cell line (e.g., a PC12 cell).

Methods of Administration and Dosage

The present methods for treatment or prevention of pain require administration of a oligonucleotide decoys, or pharmaceutical compositions thereof, to a patient in need of such treatment or prevention. The compounds and/or pharmaceutical compositions thereof may be administered by any convenient route, for example, by infusion or bolus injection, by absorption through epithelial or mucocutaneous linings (e.g., oral mucosa, rectal and intestinal mucosa, etc.), or orally. Administration can be systemic or local. Various delivery systems are known, including, e.g., encapsulation in liposomes, microparticles, microcapsules, capsules, etc., that can be used to administer a compound and/or pharmaceutical composition thereof. Methods of administration include, but are not limited to, intradermal, intramuscular, intraperitoneal, intravenous, subcutaneous, intranasal, epidural/peridural, oral, sublingual, intranasal, intracerebral, intravaginal, transdermal, rectally, by inhalation or topically, particularly to the ears, nose, eyes, or skin. In certain embodiments, more than one oligonucleotide decoy is administered to a patient. The preferred mode of administration is left to the discretion of the practitioner, and will depend in-part upon the site of the medical condition.

In specific embodiments, it may be desirable to administer one or more oligonucleotide decoys locally to the area in need of treatment. This may be achieved, for example, and not by way of limitation, by local infusion during surgery, topical application (e.g., in conjunction with a wound dressing after surgery), by injection, by means of a catheter, by means of a suppository, or by means of an implant, said implant being of a porous, non-porous, or gelatinous material, including membranes, such as sialastic membranes, or fibers. In some embodiments, administration can be by direct injection at the site (e.g., former, current, or expected site) of pain.

In certain embodiments, it may be desirable to introduce one or more oligonucleotide decoys into the nervous system by any suitable route, including but not restricted to intraventricular, intrathecal, perineural and/or epidural/peridural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant.

The amount of oligonucleotide decoy that will be effective in the treatment or prevention of pain in a patient will depend on the specific nature of the condition and can be determined by standard clinical techniques known in the art. In addition, in vitro or in vivo assays may optionally be employed to help identify optimal dosage ranges. The amount of a oligonucleotide decoy administered will, of course, be dependent on, among other factors, the subject being treated, the weight of the subject, the severity of the affliction, the manner of administration, and the judgment of the prescribing physician. In certain embodiments, a single dose of oligonucleotide decoy comprises about 5 µgs to 5 mgs, 50 µgs to 2.5 mgs, 100 µgs to 1 mg, 250 µgs to 750 µgs, or about 500 µgs of oligonucleotide decoy per kilogram of body weight.

Preferably, the dosage forms are adapted to be administered to a patient no more than twice per day, more preferably, only once per day. Dosing may be provided alone or in combination with other drugs and may continue as long as required for effective treatment or prevention of pain.

Combination Therapy

In certain embodiments, oligonucleotide decoys and/or pharmaceutical compositions thereof can be used in combination therapy with at least one other therapeutic agent which may include but is not limited to an oligonucleotide decoy. The oligonucleotide decoy and/or pharmaceutical composition thereof and the therapeutic agent can act additively or, more preferably, synergistically. In some embodiments, an oligonucleotide decoy and/or a pharmaceutical composition thereof is administered concurrently with the administration of another therapeutic agent, including another oligonucleotide decoy. In other embodiments, an oligonucleotide decoy or a pharmaceutical composition thereof is administered prior or subsequent to administration of another therapeutic agent, including another oligonucleotide decoy.

Experimental Protocols

The invention is further defined by reference to the following experimental protocol. It will be apparent to those skilled in the art that many modifications, both to materials and methods, may be practiced without departing from the scope of the invention.

The experimental model consists of mimicking a pain situation by applying to neuronal cell lines, primary dorsal root ganglion (DRG), and/or spinal cord neurons a combination of pro-inflammatory mediators (e.g., nerve growth factor, interleukin-1β, bradykinin, serotonin, substance P, etc.) known to trigger the modulation of pain genes. Pain genes expression profiling is realized by semi-quantitative Reverse Transcription-Polymerase Chain Reaction (sqRT-PCR) in several experimental situations, including but not restricted to, following pro-inflammatory mediator stimulation, with or without double stranded oligonucleotide treatment. An overview of the experiment is shown below:

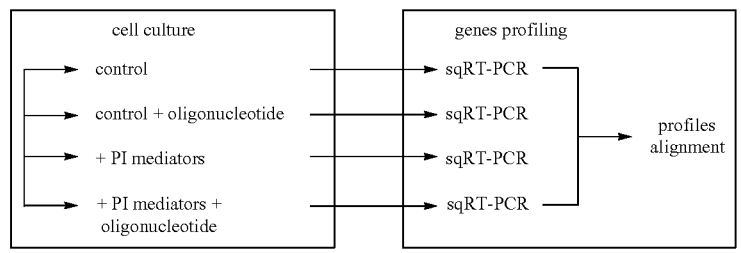

Oligonucleotide = oligonucleotide decoy(s), PI = pro-inflammatory mediator(s), sqRT-PCR = Semi-quantitative reverse transcription-polymerase chain reaction.

Cells are cultured in vitro and may be submitted to independent situations including but not limited to:
- no treatment, as a control for normal gene expression;
- oligonucleotide decoy(s) treatment to measure the effect of the later on basal gene expression;
- treatment with pro-inflammatory mediators to mimic an in vivo pain situation by changing pain gene(s) expression; and
- double treatment of pro-inflammatory mediator(s) plus oligonucleotide decoy(s) to measure the modulation level of the later in a pain-like situation.

After treatment, cells are collected and the RNA is extracted. Pain gene expression levels are measured possibly by semi-quantitative RT-PCR and the expression profiles of each situation are compared to each other.

Oligonucleotide decoy treatment consists of transfecting one ore more (concurrently or in a sequence at a time interval yet to be determined) oligonucleotide decoys of sequences selected from SEQ ID NOs.: 1-45 in neuronal cell lines, DRG, and/or spinal cord neurons. Cell lines include, but are not limited to, PC12 cells (NGF-differentiated or not), SH-SY5Y cells, Weri cells, Hela, HEK293, F-11, NS20Y, and ND7/23 cells, or any other cell line expressing one or more genes that may be selected (e.g. ACCN1-3, BDKRB1-2, BDNF, CACNA1G-H, CALCA, GRIN1, GRM1, GRM5, HTR1-3, NTRK1, P2RX3, PLC, PRKC, etc.). One or more transfection(s) is applied to the same set of cells, including or not including the same single (or set of) oligonucleotide decoys. Cells, either cell lines or primary neurons, are collected at a time after oligonucleotide decoy treatment (e.g., 24 or 48 hours post-treatment). The transfection efficiency is measured by following the uptake of a labeled oligonucleotide decoy, possibly with a dye such as fluoresceine. The efficiency is given in percentage of total cells that contain the labeled oligonucleotide decoy.

Cultured cells are collected after treatment with oligonucleotide decoy and their RNA is extracted. Extracted RNA is transformed into cDNA by reverse transcription. The amount of cDNA of each selected gene, which reflects the amount of endogenous mRNA, is measured by PCR. The same amount of PCR reaction product is loaded on an agarose gel saturated with ethidium bromide or any other suitable agent for DNA detection. Detection of DNA is performed under a UV lamp or any other suitable device and gels images are analyzed with quantification software. The amount of DNA produced during each PCR reaction is normalized on the amount of DNA produced by the control PCR reactions from housekeeping genes (e.g., ACTB, GAPDH) which reflects the total quantity of RNA initially present in cells. The comparison of ratio signal/control values obtained for each gene with and without oligonucleotide decoy treatment(s) will give a relative measure of the impact of each oligonucleotide decoy on the level of expression of genes.

Control experiments with mismatched (e.g., SEQ ID NO.: 43 annealed to SEQ ID NO.: 46, referred to hereinafter as SEQ ID NO.: 43/46), scrambled, and/or mutated double-stranded oligonucleotides are performed in parallel to ensure the measured effect is specific to each oligonucleotide decoy. Cell viability after oligonucleotide decoy treatment may be measured.

The same approach may be used with current pain drugs such as nonsteroid anti-inflammatory drugs or coxibs to compare with oligonucleotide decoys.

In certain embodiments, oligonucleotide decoys produce an effect in the expression pattern(s), which includes, but is not limited to, an inhibition and/or an induction of one or more gene(s) that may be involved in nociceptive signaling and/or the perception of pain in a patient. In certain embodiments, the inhibited gene(s) may encode pro-pain factors, like receptors of pro-inflammatory mediators, and the activated genes may encode anti-pain factors, like opioids receptors.

Strand Annealing

For oligonucleotide decoys consisting of a pair of complementary strands, the complementary strands are annealed, at equimolar concentration, in a saline buffer, e.g., Tris-EDTA (TE). The standard procedure includes maintaining the solution of both strands at a high denaturing temperature (e.g., 100° C.) for a period of time which may vary depending on the complementary strands, followed by a slow decrease in temperature (e.g., 0.3-1° C./min) until the solution reaches a low temperature of annealing (e.g., 20° C.). The proper annealing of complementary strands may be verified by any suitable standard technique, including but not restricted to running samples of annealed oligonucleotides next to un-annealed ones on a non-denaturing polyacrylamide gel. For oligonucleotide decoys that are self-annealing, substantially the same protocol is followed.

Cell Culture

DRG and/or spinal cord cells can be collected from an animal (e.g., a mammal, such as a rat or mouse) and the neurons can be freshly dissociated, using collagenase (e.g., collagenase type II) at 37° C. Cells isolated in such fashion can be plated on suitable Petri dishes (e.g., collagen coated). Neurons are maintained in appropriate media culture (e.g., DMEM). Cell lines are thawed and maintained in adequate media and Petri dishes according to the supplier recommendations. Cells are typically incubated at 37° C., 5% $CO_2$. Cell lines are cultured according to supplier recommendations.

The invention is further illustrated by the following examples which should not be construed as limiting.

EXAMPLES

Example 1

Oligonucleotide decoys of the invention include, but are not limited to, sequences presented in Table 1. In general, the oligonucleotide decoy is generated by annealing the sequence provided in the table with a complementary sequence. To generate a mismatch double-stranded oligonucleotide, the sequence provided in the table can be annealed to a sequence that is only partially complementary. For example, SEQ ID NO.: 43 can be annealed to SEQ ID NO.: 46 to produce the mismatched sequence, SEQ ID NO.: 43/46, described in the following Examples.

TABLE 1

| Oligonucleotide Sequences (5'-3') | SEQ ID NO. |
|---|---|
| GGCTTATGCAAATTCGAATGCAAATTTGTCG | SEQ ID NO.: 1 |
| CTAAGCCCACGTGACCATTGGCCAGGTGACCAGATC | SEQ ID NO.: 2 |
| GTTATGCGTGGGCGATAATGCGGGGCGTTATAG | SEQ ID NO.: 3 |
| GCCTCCCTGAGCTCATTGACGTATCTCGG | SEQ ID NO.: 4 |
| CGAATATGACTGAGAATGACTCAGATTTGC | SEQ ID NO.: 5 |
| GGTTCTATGATTTTGGAATCGGATTGTGCAAAGAAGC | SEQ ID NO.: 6 |
| GCTTCAGGATGTCCATATTAGGAGATCTTGTTCG | SEQ ID NO.: 7 |
| GGCCACAGGATGTAGGATGTCCATATTAGGATGC | SEQ ID NO.: 8 |
| GTTCTCTAAAAATAAAAGGCTAAAAATAAAAGTCG | SEQ ID NO.: 9 |
| ATTAGGGGCGGGGTCCGGGGCGGGGTATTA | SEQ ID NO.: 10 |
| GTTATGGCGGGGCGGGGCGGGGCCGGGCGGTTTAC | SEQ ID NO.: 11 |
| GGCAATGTGGTTTTAGTGTGGTTTTACGG | SEQ ID NO.: 12 |
| GCCGTTTGGGGTCATAGAACCACAGGAACCACACGG | SEQ ID NO.: 13 |
| CATTGCCCGGAAATGGACCGGATGTAATTTCC | SEQ ID NO.: 14 |

TABLE 1-continued

| Oligonucleotide Sequences (5'-3') | SEQ ID NO. |
|---|---|
| GTTCTTGGAAAATAAATGGAAAATAGTGGAAAATAAGTCG | SEQ ID NO.: 15 |
| CGTTCCCACTTCCTGCGACCACTTCCTGCCGGG | SEQ ID NO.: 16 |
| CTGCACCTATAAATGGCCTATAAATGGGGATGC | SEQ ID NO.: 17 |
| GCTTATTTCGCGGAAGGTTTCCCGGAAGTGGCG | SEQ ID NO.: 18 |
| GCTGTGCCTTATCTCTTTGGGATAACTGGCG | SEQ ID NO.: 19 |
| GCTTAATGAATAAGAGGAAAAATGCATGCTGG | SEQ ID NO.: 20 |
| GTTCTGAGATTGCACGATGAGATTTCACAGTCG | SEQ ID NO.: 21 |
| GTCCCGCATAAATAATGGCATCCTTAATCGCG | SEQ ID NO.: 22 |
| GTGCAGGCAAGAGTAGAGACAGGCAAGAGTAGATGC | SEQ ID NO.: 23 |
| CCGCCAATAATTAATTATTAAGGCC | SEQ ID NO.: 24 |
| GCTTCGTTCCATTTCCGGTCTCGGTTTCCCCATTC | SEQ ID NO.: 25 |
| GCTGCTGTGGAATATCGACCTGTGGAATATCGTG | SEQ ID NO.: 26 |
| GCCGTATAAATGTGCTATAAAAGTTTTAAGACCGTGC | SEQ ID NO.: 27 |
| GCCGTATAAATGTGCTATAAAAGCCGTGC | SEQ ID NO.: 28 |
| ATGCTGCGCTTTTCTCCAATCTGCGG | SEQ ID NO.: 29 |
| CGTTCTCCGATTGGTCACGGACTCTCCGATTGGTCACGGC | SEQ ID NO.: 30 |
| GCGCACCCCAGCCTGGCTCACCCACGCG | SEQ ID NO.: 31 |
| GATCCTTTGCCTCCTTCGATCCTTTGCCTCCTTCAAG | SEQ ID NO.: 32 |
| GGTGTTTGGGAGAGCTTTGGGAGGATACG | SEQ ID NO.: 33 |
| GCTAATCACTCAGCATTTCGGTGAGGGAAGTGAAAG | SEQ ID NO.: 34 |
| CCTTTCAGCACCACGGACAGCGCCAGCTTCAGCACCACGGACAGCGCCTCG | SEQ ID NO.: 35 |
| GGATCGAACATGGAGTCAGTGAGAAATCAGGATCGG | SEQ ID NO.: 36 |
| GGATCGAAGCCGGAGTCAAGGAGGCCCCTGATCGG | SEQ ID NO.: 37 |
| CCGAAAGGACAAAGGTCAAGTCGAAAGGACAAAGGTCAG | SEQ ID NO.: 38 |
| CGGGAGAAAATTCGGGAACGTTCAAGAATTGTCGG | SEQ ID NO.: 39 |
| GTTATGCGTGGGCGTAGATGCGGGGCGTTATAG | SEQ ID NO.: 40 |
| GATGCGTGGGCGTAGG | SEQ ID NO.: 41 |
| GTATGCGTGGGCGGTGGGCGTAG | SEQ ID NO.: 42 |
| GTTATGCGTTTGTAGATGCTTTCGTTATAG | SEQ ID NO.: 43 |
| GTTATGCGTGGGCGATATAG | SEQ ID NO.: 44 |
| GATGCGTGGGCGTTGACGTGGAAAATGC | SEQ ID NO.: 45 |
| CTATTTCGAAACGATCTACATTGGCATAAC | SEQ ID NO.: 46 |
| CGTTCCCACTTCCTGCGACCGG | SEQ ID NO.: 47 |
| GGGTGAAGGCAAGAGTAGAGCGGCGG | SEQ ID NO.: 48 |
| CGTTCTCCGATTGGTCACGCG | SEQ ID NO.: 49 |
| GTACTCCCTTTGCCTCCTTCAACCGG | SEQ ID NO.: 50 |

TABLE 1-continued

| Oligonucleotide Sequences (5'-3') | SEQ ID NO. |
|---|---|
| CCTTATTCAGCACCACGGACAGCGCCATTCG | SEQ ID NO.: 51 |
| GCGAAAGGACAAAGGTCAGGCGG | SEQ ID NO.: 52 |
| GGCTTGCTGTGGAATATCGATGGTG | SEQ ID NO.: 53 |

Example 2: Affinity and Specificity of EGR1 Oligonucleotide Decoy Sequences

SEQ ID NO.: 3, which is designed to bind EGR1 transcription factor, has a structure that is typical of class of oligonucleotide decoys of the invention. The structure of SEQ ID NO.: 3 includes, in order from 5' to 3', a 5' flanking sequence, a first transcription factor binding site, a linker sequence, a second transcription factor binding site, and a 3' flanking sequence. SEQ ID NO.: 40, which has 94% identity with SEQ ID NO.: 3 and the same basic structure, is predicted in silico to bind EGR1 better than SEQ ID NO.: 3. Pharmacological analysis of SEQ ID NO.: 40 was performed using a transcription factor ELISA kit specific for EGR1 binding detection. The sensitivity of transcription factor ELISA technology is ten times more sensitive than classical EMSA experiments, allowing detailed pharmacological studies of transcription factor decoys.

The proper annealing of forward and reverse strands of SEQ ID NO.: 40 was confirmed on a 2.5% agarose gel, as shown in FIG. 1A. Binding experiments were conducted with the human form of EGR1 (hEGR1) present in nuclear extracts of TPA-stimulated K-562 cells. See, e.g., FIG. 1B.

Figure 2B:
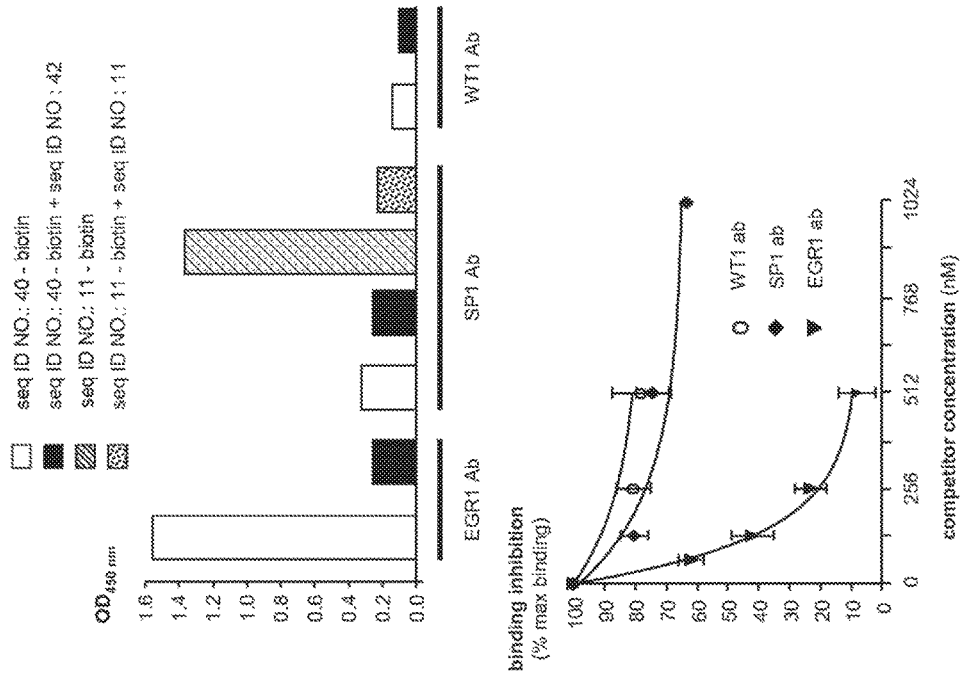
FIGS. 2A-2B. A. Relative affinity. Quantitative competition ELISA involving hEGR1 were performed using a constant concentration of biotinylated SEQ ID NO.: 40 (128 nM) as the probe and 10 µg of protein extract. The probe-protein mix was incubated with increasing concentrations of SEQ ID NO.: 40, SEQ ID NO.: 41 or SEQ ID NO.: 42 competitors. The inhibition of hEGR1 binding by the probe was measured for each competitor at various concentrations and the resulting inhibition curves were fitted to an exponential decay model. Respective $IC_{50}$ are 215 nM, 250 nM and 99 nM. Mean±SEM are given as a percentage of the maximum hEGR1 binding obtained with the probe in absence of competitor; n=2-4. B. Relative specificity. The relative binding of EGR1 oligonucleotide decoy sequences to hSP1 and hWT1 transcription factors was measured using quantitative ELISA. Top graph: representative OD binding values of SEQ ID NO.: 40 (128 nM) to either hSP1 or hWT1 transcription factors, as compared to hEGR1 binding, was detected with transcription factor-specific antibodies in either the presence or absence of SEQ ID NO.: 42 competitor (512 nM). For comparison, SEQ ID NO.: 11 binding to hSP1 is shown. Bottom graph: binding inhibition curves for each factor are displayed. Mean and SEM are given as a percentage of the maximum binding for each transcription factor observed in absence of competitor; Ab=antibody, n=1-3.
Figure 2A:
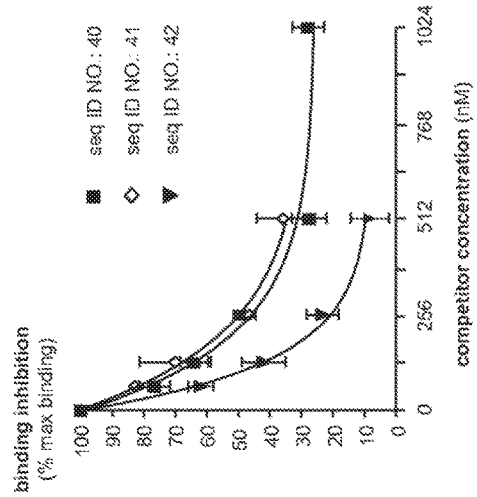

Quantitative competition ELISA using SEQ ID NO.: 40 and SEQ ID NO.: 41 show that SEQ ID NO.: 40 exhibits strong hEGR1 binding activity, as shown in FIG. 2A. In our experimental context, an half-inhibition concentration ($IC_{50}$) value represents the concentration of competitor that gives 50% inhibition of the probe binding measured in absence of the competitor and, thus, is a measure of the relative affinities of sequences against each other. The results indicate that SEQ ID NO.: 40, which contains two EGR1 transcription factor binding sites, bares a relative affinity to hEGR1 similar to the consensus SEQ ID NO.: 41, which contains a single EGR1 transcription factor binding site, with $IC_{50}$ of 215 nM and 250 nM, respectively.

We discovered that SEQ ID NO.: 42, which is 70% homologous to SEQ ID NO.: 3 but includes a specific fusion of the two EGR1 transcription factor binding sites present in SEQ ID NO.: 3, has an affinity for EGR1 two times higher than the single consensus sequence, SEQ ID NO.: 41, with an $IC_{50}$ of 99 nM. See FIG. 2A.

Crystal structure experiments studies have shown that a single EGR1 protein is able to bind its consensus binding sequence through three zinc finger domains. It is known that protein-protein interactions can directly change DNA binding activities, as proven for the AP1 factors c-jun and c-fos, where the c-jun:c-fos dimer binds to AP1 response elements five to thirty times better than c-jun:c-jun dimers. Without intending to be bound, we believe that the fusion of the two EGR1 transcription factor binding sites present in SEQ ID NO.: 42 induces protein-protein interactions between two EGR1 factors and thereby mutually increases their DNA binding affinity. In any event, the very high affinity of SEQ ID NO.: 42 for EGR1, as compare to known binding sequences, makes SEQ ID NO.: 42 particularly attractive as a pharmaceutical inhibitor of hEGR1.

Figure 1C:
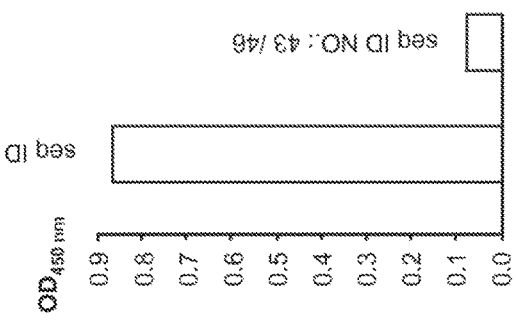
Figure 1B:
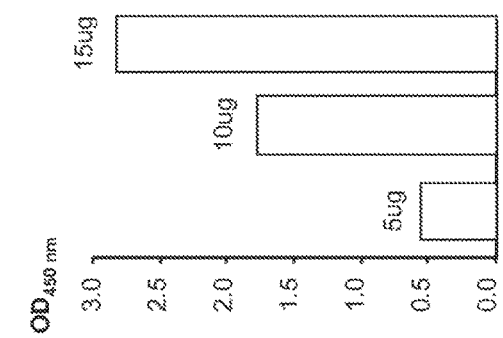

The absence of non-specific oligonucleotides binding effect in our ELISA experiments was demonstrated by the lack of EGR1 binding to the mismatch sequence, SEQ ID NO.: 43/46, as shown in FIG. 1C. In addition, SP1 and WT1 transcription factors, which are structurally related to EGR1 and are able to bind GC-rich DNA sequences similar to the EGR1 consensus binding sequence, bound poorly to EGR1 oligonucleotide decoys. ELISA experiments detecting hSP1 binding demonstrated that SEQ ID NO.: 40 bound poorly to SP1 as compare to the SP1-specific oligonucleotide decoy, SEQ ID NO.: 11, with an OD value 80% lower. See FIG. 2B (top panel). Furthermore, competition experiments demonstrated that SEQ ID NO.: 42 does not bind efficiently to hSP1, even at high excess concentrations, as shown in FIG. 2B, top and bottom panels. A similar lack of affinity was observed for EGR1 oligonucleotide binding to hWT1. See FIG. 2B, top and bottom panels.

Altogether, pharmacological experiments reveal that SEQ ID NO.: 42 is a powerful hEGR1 inhibitor compound as (i) it has a higher relative affinity for hEGR1 as compare to both the single consensus binding site decoy (SEQ ID NO.: 41) and the double consensus binding site decoy (SEQ ID NO.: 40) and, (ii) it is highly specific.

Example 3: Inhibition of hEGR1 Transcriptional Activity in Cells

The capacity of SEQ ID NO.: 40 and SEQ ID NO.: 42 to inhibit hEGR1 transcriptional activity in human cells was measured through their effect on CDK5R1 gene expression. CDK5R1 is an activator of the CDK5 kinase. Both are up-regulated in pain neurons following peripheral inflammation and regulate nociceptive signaling, notably via phosphorylation of the capsaicin receptor, TRPV1. hEGR1 directly binds to the CDK5R1 promoter in human HL60 cells and controls its up-regulation following cell differentiation by 1,25-Dihydroxyvitamin D3. Segment of the natural CDK5R1 promoter used as a decoy in HL60 cells are already known to inhibit CDK5R1 expression. We assessed the efficiency of our decoy sequences to inhibit hEGR1 activity by measuring the level of inhibition of CDK5R1 they confer following HL60 cell differentiation. CDK5R1 mRNA expression level was measured by sq RT-PCR (see, e.g., FIG. 3A) and half-inhibition concentrations $IC_{50}$ refers to the decoy concentration needed to produce 50% inhibition of the maximum CDK5R1 mRNA expression level measured after 1,25-Dihydroxyvitamin D3 differentiation.

We confirmed the up-regulation of CDK5R1 mRNA expression level following 1,25-Dihydroxyvitamin D3 application, as well as the presence of hEGR1 in HL60 cells, as shown in FIG. 3B. The high transfection yield (70%) of our decoy sequences into HL60 cells is illustrated in FIG. 3C. FIG. 3D shows that we did not measure any significant difference in the number of dead cells between 1,25-Dihydroxyvitamin D3 treatment alone and combined with decoy sequences at concentrations up to 1 μM, demonstrating the lack of toxicity of EGR1 decoy in HL60 cells.

Figure 4A:
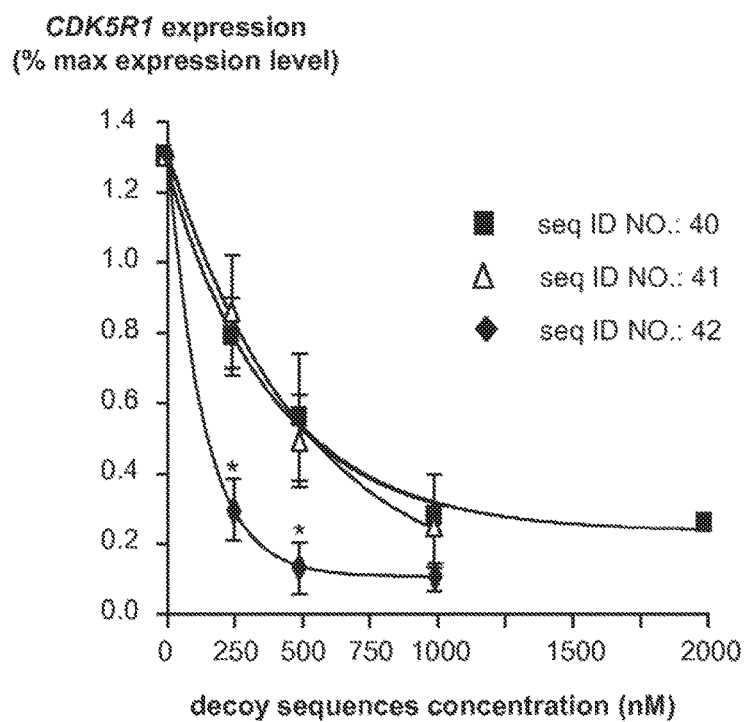
FIGS. 4A-4B. Dose responses. CDK5R1 mRNA expression level was measured by sqRT-PCR after transfection of increasing concentrations of EGR1 oligonucleotide decoys (250 nM, 500 nM, and 1000 nM). CDK5R1 mRNA expression level was normalized against ACTB mRNA expression level and results are given as a percentage of inhibition of the maximum CDK5R1 expression level 48 hours after 1,25-Dihydroxyvitamin D3 application. The concentrations of SEQ ID NO.: 40, SEQ ID NO.: 41 and SEQ ID NO.: 42 needed to obtain 50% of CDK5R1 mRNA expression inhibition ($IC_{50}$) were 443 nM, 502 nM, and 136 nM, respectively; values are given as Mean±SEM, *=different from consensus SEQ ID NO.: 41, p≤0.05, n≥3. D. Decoys efficacy illustration. Representative CDK5R1 sqRT-PCR products separated on a 1% agarose gel are displayed before and after treatment with either SEQ ID NO.: 40 or SEQ ID NO.: 42; CTR=control, VIT=1,25-Dihydroxyvitamin D3 treatment.
Figure 4B:
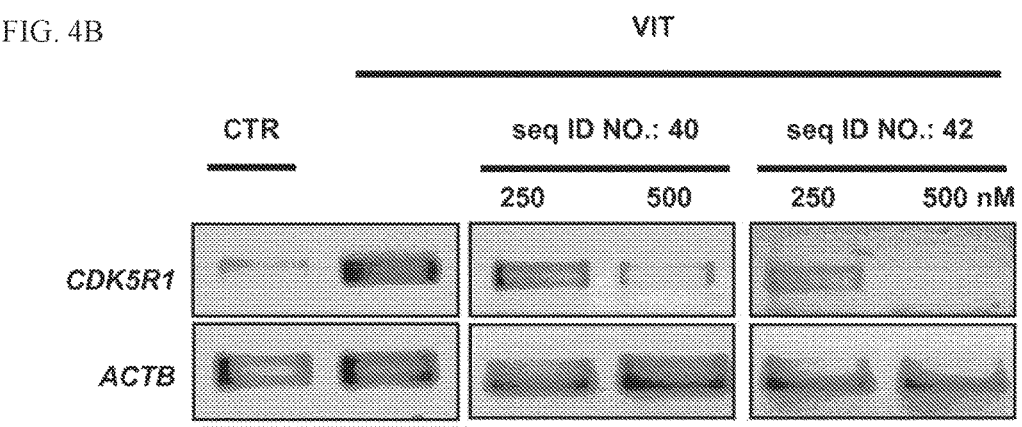

Dose response experiments from 250 nM to 2 μM conducted with our hEGR1 decoy sequences are displayed in FIG. 4A. SEQ ID NO.: 40 and SEQ ID NO.: 41 have a similar $IC_{50}$, with values of 544 nM and 529 nM, respectively. This is directly consistent with the fact that the two sequences display roughly the same binding affinity for hEGR1. SEQ ID NO.: 42 is over three time more effective at inhibiting CDK5R1 mRNA expression than the other decoys, with an $IC_{50}$=150 nM, reflecting its higher affinity for hEGR1. Typical pictures of CDK5R1 mRNA expression detection on agarose gels illustrating the differential $IC_{50}$ of SEQ ID NO.: 40 and SEQ ID NO.: 42 are displayed in FIG. 4B. Those data reveal a direct relationship between the relative affinities of hEGR1 decoy sequences and their efficiency in a cellular context and further confirm the therapeutic potential of SEQ ID NO.: 42 as an hEGR1 inhibitor and for treating pain.

The specificity of SEQ ID NO: 42 activity was verified using two methods. First, we verified the absence of CDK5R1 expression inhibition from the mismatch sequence SEQ ID NO.: 43/46, which indicates the lack of non-specific nucleotide exposure effects. See FIG. 3E, left panel. Second, we confirmed the specificity of SEQ ID NO.: 42 activity by showing its lack of effect on the regulation of BCL2, a anti-apoptotic gene that lacks hEGR1 response element within its promoter and is not known to be regulated by hEGR1 in HL60 cells. Consistent with previous observations, we measured a down-regulation of BCL2 mRNA expression after HL60 differentiation, and this down-regulation was not altered by SEQ ID NO.: 42 oligonucleotide decoy treatment. See FIG. 3E, right panel.

Example 4: Inhibition of Pain Genes Expression

PC12 are pheochromocytoma cells extensively used as a model to investigate pain signaling pathways because they express and regulate numerous pain genes in a fashion similar to endogenous pain neurons in response to pro-inflammatory mediators such as NGF or cAMP elevating compounds. We measured the effect of seq ID NO.: 42 decoy treatment on pain genes expression profile. We selected 11 pain genes based on (i) their critical roles in multiple pain syndromes, (ii) their different positions along pain signaling pathways and (iii) the strong parallel between the regulation of their expression between endogenous pain neurons and PC12 cells. They belong to four genes classes: ion channels (Scn9a, Cacna1b), membrane receptors (Grm5, Bdkrb2, P2rx3, Htr3a), signaling and neurotransmitter synthesis enzymes and related proteins (Cdk5r1, Gch1, Pnmt, Nos1) and neurotransmitter (Bdnf).

We obtained similar transfection yield in PC12 (80%) cells as compare to HL60 cells, as shown in FIG. 5A. FIG. 5B displays the basal expression level of the selected pain genes normalized upon Gapdh expression level, with and without SEQ ID NO.: 42 decoy treatment. The results indicate that the basal expression of Bdkrb2, Htr3a and Scn9a is strongly inhibited by SEQ ID NO.: 42 treatment. Interestingly, all three of the genes encode membrane proteins—two receptors and one ion channel. The absence of impact on the other genes expression level emphasizes the specificity of the EGR1 decoy treatment in PC12 cells.

In further experiments, we treated PC12 cells with two pain mimicking stimuli that are known to mobilize EGR1—NGF and forskolin. NGF induces the expression of EGR1 and forskolin acts as a permissive factor for EGR1 activity in PC12 cells. Twenty-four hours after NGF/forskolin treatment of PC12 cells, we observed significant up-regulation of 7 of the 11 genes examined, including Bdnf Grm5, Scn9a, Nos1, Gch1, Cdk5r1 and Pnmt. Our results are in agreement with several other studies showing the up-regulation of such pain genes in PC12 cells following NGF exposure. Treatment with SEQ ID NO.: 42 fully prevented the endogenous up-regulation of five of the genes, including Scn9a, Nos1, Gch1, Cdk5r1 and Pnmt. Interestingly, all of these genes except Scn9a encode enzymes-related proteins. Typical pictures of pain gene cDNA detection on agarose gels illustrating the two complementary effect of SEQ ID NO.: 42 treatment, basal expression inhibition and up-regulation block, are shown in FIG. 5D. We verified the lack of non-specific oligonucleotides exposure effect in PC12 cells by showing the absence inhibition by the mismatch sequence SEQ ID NO.: 43/46 on two pain genes, as shown in FIG. 5E.

SEQ ID NO.: 42 inhibits the expression level of seven out of eleven pain genes on two different levels, basal transcription and pain-induced up-regulation. It is possible that the two effects operate on distinct classes of genes, as within our small scale experiments, basal transcription levels were inhibited among essentially only membrane proteins while under pain-like conditions the normal up-regulation of pain-associated genes was inhibited among essentially only genes encoding enzymes. The high proportion of genes regulated and their complementary qualities reflects the importance of EGR1 in pain and is in agreement with animal knockout and antisense studies demonstrating that in absence of EGR1, major pain syndromes are not maintained. From a therapeutic prospective, the interest of inhibiting EGR1 activity using SEQ ID NO.: 42 is the ability to concurrently modulate the expression of a high number of pain genes that are active at multiple steps of pain signaling pathways. For instance, a unique treatment with SEQ ID NO.: 42 would be sufficient to concurrently inhibit a receptor like BDRKD2 that perceive pain signals, an ion channel like SCN9A that relays pain signals within neurons, and a neurotransmitter synthesis enzyme like GCH1 that participate to its synaptic transmission between neurons, whereas normally a complex polypharmacy approach would be necessary to simultaneously affect such different targets. Altogether, the experimental data showing the strong inhibitory effect of SEQ ID NO.: 42 on EGR1-dependent pain gene expression reveals its therapeutic potential for pain treatment.

Example 5: Complementary Decoy Studies

We analyzed several other oligonucleotide decoys sequences that target transcription factors with distinct roles, including (i) CREB/ATF and NFAT, which are immediate early genes that are critical in pain gene expression plasticity and complement the role of EGR1, and (ii) AML1 and SP1 factors, which are critical in the maintenance of basal expression and tissue specific expression of numerous pain genes.

Figure 6A:
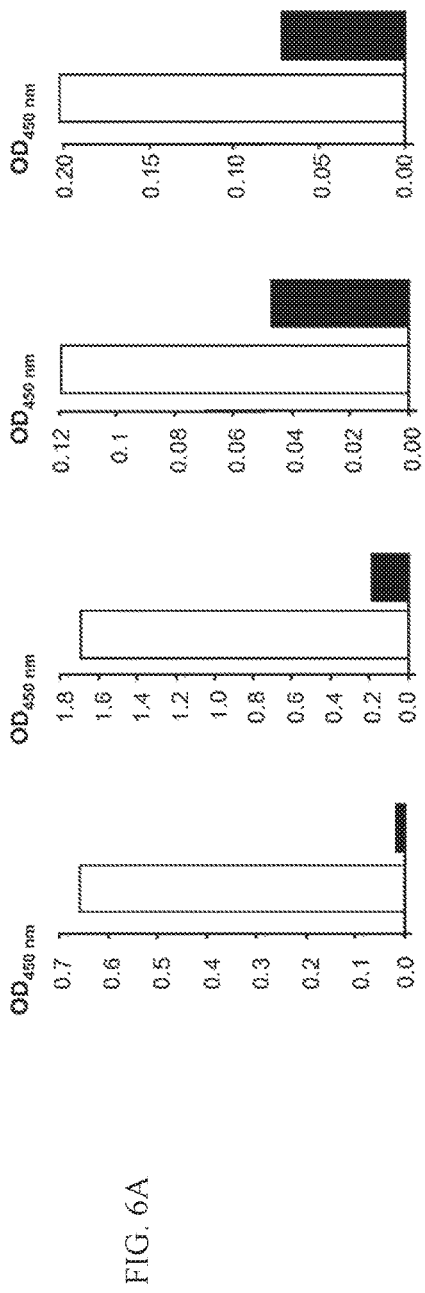
FIGS. 6A-6B. A. Decoys binding and specificity. ELISA were run as previously described with biotinylated SEQ ID NO.: 4, SEQ ID NO.: 11, SEQ ID NO.: 12, and SEQ ID NO.: 15 (128 nM). CREB/ATF, SP1, RUNX1 and NFATC1 primary antibodies were used, respectively, to detect transcription factor binding to the sequences (white bars). The specificity of each binding was checked in presence of respective competitors (2 µM, black bars). B. Inhibition of up-regulation of pain genes. Bdnf, Scn9a, Cdk5r1, Pnmt and Nos1 genes are up-regulated 24 h after NGF+forskolin treatment (control=white bars, NGF+forskolin=black bars). The graph displays the effect of decoy treatments with SEQ ID NO.: 4 (horizontal dashed bars), SEQ ID NO.: 12 (small dots bars), and SEQ ID NO.: 15 (large dots bars); values are given as Mean±SEM, expression values were normalized to Gapdh expression level (arbitrary units); p≤0.1, p≤0.05 for different from control, n=2-5.

FIG. 6A shows ELISA experiments for SEQ ID NO.: 4, which targets CREB/ATF, SEQ ID NO.: 11, which targets SP1, SEQ ID NO.: 12, which targets RUNX1, and SEQ ID NO.: 15, which targets NFAT. Graphs display the binding OD values obtained for each sequence with either the biotinylated version used as a probe alone or in presence of respective competitor. All sequences bound their targeted factors, as shown by binding ODs higher than the background. Differences in the binding ODs from one sequence to another likely reflect, aside from the individual qualities of the antibodies used for ELISA detection, differences in the quantity of each transcription factor within nuclear extracts, and in their relative activation levels. The binding inhibition observed in the presence of competitors for each sequence indicates their specificity for their respective targets.

Figure 6B:
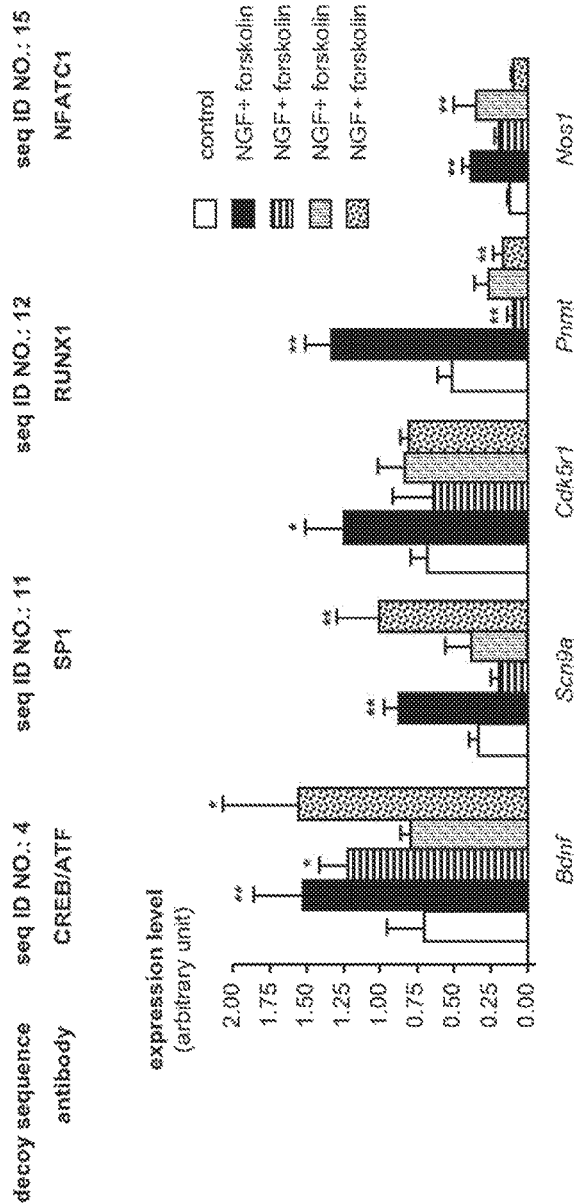

The therapeutic potential of three of the sequences was assessed in PC12 cells, as described for SEQ ID NO.: 42. The presence of CREB/ATF, NFAT and RUNX factors has been previously described in PC12 cells. Expression levels of pain genes before and after SEQ ID NO.: 4, SEQ ID NO.: 12, and SEQ ID NO.: 15 decoy treatment are shown in Table 2A. FIG. 6B illustrates the effect of oligonucleotide decoy treatment measured under pain-like conditions. Each sequence inhibited the expression of multiple genes under both basal and pain-like conditions. See Tables 2A and 2B, FIG. 6B. For example, SEQ ID NO.: 4, which targets CREB/ATF transcription factors, inhibited the basal expression level of Bdkrb2, Grm5, Htr3a, Pnmt and Nos1 and prevents the up-regulation of Scn9a, Cdk5r1, Pnmt and Nos1. We observed some overlap in the inhibition profiles of decoy sequences over the regulation of pain genes expression. Such redundancy is not surprising in the light of gene expression being controlled by scaffolds of transcription factors rather than by a single one and that all investigated factors are involved in pain signaling. In vivo, the respective involvement of each of transcription factor in the regulation of genes expression may depend on the type of pain neuron it is expressed in and in its global activity resulting from the integration of complex pain signaling pathways. Therefore, the therapeutic relevance of a particular decoy may depend on the pain syndrome, intensity and stage.

Some important pain genes like Scn9a, which is critical in the genesis of action potential in pain neurons (e.g., nonsense mutations in Scn9a generate insensitivity to pain), are very sensitive to transcription regulation. Scn9a up-regulation after NGF and forskolin treatment appears to implicate a transcriptional network that includes the three immediate early genes Egr1, Creb/Atf and Nfat. If the activity of a single one of those factors is inhibited with one of our decoy sequences, the regulation is lost. This represents an important potential therapeutic advantage to the decoy approach as the expression of a given gene may be inhibited without the need to target all the transcription factors involved in its regulation.

Altogether, those experiments demonstrate that our decoy sequences have the potential to concurrently inhibit a high number of pain genes, a unique property for pain therapy.

Example 6: Composite Oligonucleotide Decoys

Considering that a certain level of redundancy operates between transcription factor activities, we developed a composite decoy sequence, SEQ ID NO.: 45, for the concurrent inhibition of EGR1, CREB/ATF and NFAT. The interest of such a sequence is the simultaneous inhibition of three major immediate early genes involved in neuronal plasticity and that integrate complementary signaling pathways critical for pain sensation. Signaling kinases like the MAPK/ERK pathways, which are activated by numerous metabotropic pain receptors (e.g., the NGF receptors NTRK1/NGFR), mobilize EGR1, while the calcium signaling pathways mobilized by calcium- and cationic-channels activate CREB and NFAT. The sequence of SEQ ID NO.: 45 includes, in 5' to 3' order, transcription factor binding sites for EGR1, CREB/ATF and NFAT, each selected from the individual response elements of SEQ ID NO.: 3 (EGR1), SEQ ID NO.: 4 (CREB/ATF), and SEQ ID NO.: 15 (NFAT).

The binding properties of SEQ ID NO.: 45 for each factor are displayed FIG. 7A,B. Parallel ELISA competition experiments with SEQ ID NO.: 41 and SEQ ID NO.: 45 show that the relative binding affinity of this composite sequence for EGR1 is as high as the oligonucleotide decoy SEQ ID NO.: 41. Furthermore, the inhibition of hEGR1 activity in HL60 cells induced by SEQ ID NO.: 45 treatment matches the inhibition induced by SEQ ID NO.: 41 (FIG. 7C), both having overlapping dose-response curves. These results are consistent with our prior observation that cell efficiency is directly linked to the relative affinity measured in ELISA experiments. Finally, further ELISA competition experiments show that, in plus of binding to hEGR1, SEQ ID NO.: 45 also specifically binds to hCREB/hATF and hNFAT factors (FIG. 7B).

We investigated the impact of SEQ ID NO.: 45 on pain gene expression in PC12 cells (table 2). Use of a composite sequence provides two benefits: (i) a potentially additive effect on the number and type of genes inhibited; and (ii) potentially greater inhibition of particular genes that are only partially inhibited by oligonucleotide decoys specific to single transcription factors. The additive effect was illustrated for SEQ ID NO.: 45 by the differential inhibition among the composite, NFAT, and EGR1 decoys. For example, SEQ ID NO.: 42 does not inhibit Grm5 basal expression, while both SEQ ID NO.: 15 (NFAT) and SEQ ID NO.: 45 (composite) do. Similarly, in pain-like condition, SEQ ID NO.: 15 (NFAT) does not prevent Scn9a up-regulation after NGF and forskolin treatment, while SEQ ID NO.: 42 (EGR1) and SEQ ID NO.: 45 (composite) do.

The intensity effect appears strongly in the regulation of Bdrkb2 and Scn9a genes expression, as shown in FIG. 7D. When one gene is inhibited by at least 2 transcription factors targeted by the composite sequence, the intensity of the inhibition is stronger than the inhibition conferred by the individual sequences. For instance, Bdrkb2 basal expression is individually inhibited by a factor of 5 by both SEQ ID NO.: 4 and SEQ ID NO.: 15, while it is inhibited by a factor of 10 by the composite oligonucleotide decoy, SEQ ID NO.: 45.

Example 7: Treatment of Pain In Vivo

Inflammation is a major source of pain. It is a feature common to numerous pain syndromes, such as arthritic and post-operative pain. The Complete Freund Adjuvant model (CFA) is a well-characterized inflammatory pain model that is commonly used to reproduces features of human inflammatory pain. For instance, following inflammation in the hindpaw, animals develop a robust and long-lasting mechanical allodynia (i.e., a pain in response to a mechanical stimulus normally non-painful), a phenomenon that is a major source of pain and limitations for patients ambulation, breathing and feeding in a post-operative context.

Figure 8A:
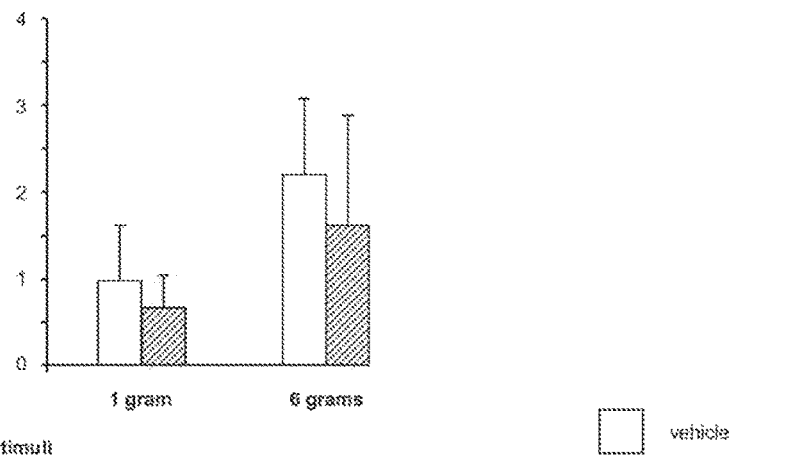
FIG. 8A-8B. A. SEQ ID NO.: 42 anti-allodynic effect at day 1. Rats mechanical sensitivity was tested at day 1 post-CFA injection using Von Frey filaments of 2 different forces: 1 gram and 6 grams. Vehicle and SEQ ID NO.: 42 treatment conditions were tested. B. SEQ ID NO.: 42 anti-allodynic effect at day 4. Mechanical sensitivity was tested again at day 4 post-CFA. Again, both vehicle and SEQ ID NO.: 42 treatment conditions were tested; values are given as mean±SEM n=7.
Figure 8B:
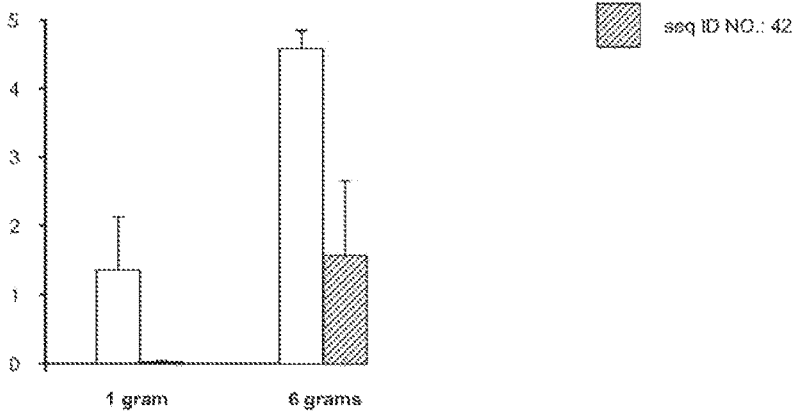

In our experiments and accordingly to the literature, mechanical allodynia was measurable on the inflamed hindpaw at day 1 post-CFA and reached its maximum within 4 days, as shown in FIG. 8. Treatment with SEQ ID NO.: 42 resulted in an anti-allodynic tendency at day 1 post-CFA (FIG. 8A) and a robust reversal of allodynia at day 4 post-CFA for each stimulus force tested (FIG. 8B). This is in agreement with EGR1 being involved in the maintenance of neuronal plasticity events, like neuronal sensitization and long-term potentiation, rather than their onset.

TABLE 2

| | BDNF | | NOS1 | | BDKRB2 | | P2RX3 | | Grm5 | | HTR3A | |
|---|---|---|---|---|---|---|---|---|---|---|---|---|
| | Mean | SEM | Mean | SEM | Mean | SEM | Mean | SEM | Mean | SEM | Mean | SEM |
| Pain Genes Basal Expression | | | | | | | | | | | | |
| control | 0.7 | 0.29 | 0.13 | 0.02 | 1.16 | 0.09 | 0.94 | 0.32 | 0.15 | 0.05 | 0.6 | 0.1 |
| ID No. 4 | 0.54 | 0.14 | 0.06 | 0.01 | 0.28 | 0.02 | 0.72 | 0.39 | 0.04 | 0.01 | 0.01 | 0.00 |
| ID No. 12 | 0.92 | 0.05 | 0.04 | 0.003 | 0.38 | 0.07 | 0.66 | 0.18 | 0.15 | 0.11 | 0.06 | 0.04 |
| ID No. 15 | 0.63 | 0.04 | 0.12 | 0.05 | 0.22 | 0.03 | 0.59 | 0.20 | 0.03 | 0.01 | 0.02 | 0.01 |
| ID No. 42 | 0.89 | 0.26 | 0.08 | 0.03 | 0.51 | 0.24 | 0.80 | 0.27 | 0.20 | 0.19 | 0.04 | 0.01 |
| ID No. 45 | 0.626 | 0.08 | 0.021 | 0.005 | 0.05 | 0.002 | 1.038 | 0.21 | 0.048 | 0.01 | 0.06 | 0.02 |
| NGF and Forskolin Stimulation | | | | | | | | | | | | |
| NGF + FSK | 1.52 | 0.33 | 0.38 | 0.06 | 1.22 | 0.17 | 1.00 | 0.23 | 1.07 | 0.18 | 0.83 | 0.09 |
| ID No: 4 | 1.22 | 0.20 | 0.19 | 0.03 | 0.80 | 0.22 | 0.89 | 0.34 | 0.98 | 0.11 | 0.53 | 0.13 |
| ID No: 12 | 0.79 | 0.06 | 0.35 | 0.15 | 0.67 | 0.25 | 0.92 | 0.51 | 1.13 | 0.23 | 0.46 | 0.04 |
| ID No: 15 | 1.55 | 0.52 | 0.10 | 0.01 | 1.10 | 0.19 | 1.32 | 0.31 | 0.81 | 0.17 | 0.28 | 0.09 |
| ID No: 42 | 1.33 | 0.03 | 0.11 | 0.06 | 1.49 | 0.13 | 0.79 | 0.42 | 0.83 | 0.34 | 0.37 | 0.18 |
| ID No: 45 | ■ | ■ | 0.04 | 0.01 | 1.27 | 0.38 | 0.83 | 0.21 | 0.63 | 0.32 | 0.87 | 0.18 |

| | CACNA1b | | GCH1 | | CDKR1 | | PNMT | |
|---|---|---|---|---|---|---|---|---|
| | Mean | SEM | Mean | SEM | Mean | SEM | Mean | SEM |
| Pain Genes Basal Expression | | | | | | | | |
| SCN9Q | | | | | | | | |
| control | 1.08 | 0.21 | 0.33 | 0.06 | 0.76 | 0.10 | 0.68 | 0.11 | 0.51 | 0.10 |
| ID No. 4 | 1.02 | 0.15 | 0.17 | 0.15 | 1.07 | 0.30 | 0.98 | 0.12 | 0.05 | 0.01 |
| ID No. 12 | 0.84 | 0.19 | 0.04 | 0.01 | 0.98 | 0.22 | 0.29 | 0.02 | 0.06 | 0.02 |
| ID No. 15 | 0.30 | 0.13 | 0.11 | 0.002 | 1.03 | 0.05 | 0.98 | 0.40 | 0.08 | 0.01 |
| ID No. 42 | 1.03 | 0.29 | 0.11 | 0.01 | 1.04 | 0.08 | 0.86 | 0.23 | 0.41 | 0.17 |
| ID No. 45 | 0.826 | 0.06 | 0.045 | 0.02 | 1.025 | 0.14 | 0.578 | 0.06 | 0.07 | 0.02 |
| NGF and Forskolin Stimulation | | | | | | | | |
| SCN9A | | | | | | | | |
| NGF + FSK | 0.91 | 0.14 | 0.87 | 0.11 | 1.81 | 0.35 | 1.25 | 0.26 | 1.34 | 0.18 |
| ID No: 4 | 0.80 | 0.13 | 0.19 | 0.06 | 2.18 | 0.69 | 0.65 | 0.27 | 0.09 | 0.05 |
| ID No: 12 | 1.49 | 0.40 | 0.38 | 0.16 | 1.59 | 0.25 | 0.84 | 0.18 | 0.26 | 0.09 |
| ID No: 15 | 1.04 | 0.14 | 1.00 | 0.28 | 1.95 | 0.21 | 0.80 | 0.05 | 0.17 | 0.06 |
| ID No: 42 | 1.36 | 0.46 | 0.28 | 0.09 | 0.99 | 0.12 | 0.66 | 0.20 | 0.58 | 0.18 |
| ID No: 45 | 1.63 | 0.40 | 0.10 | 0.01 | 0.68 | 0.32 | ■ | ■ | 0.19 | 0.09 |

Values are given as Mean and SEM, and represent the expression level in PC12 cells of each gene normalized on the Gapdh expression level. Units are arbitrary. Black cases represent experiments not done. n=2-4.

Altogether, those results indicate that SEQ ID NO.: 42 treatment has a robust anti-allodynic effect, demonstrating its therapeutic potential for treating pain in vivo. Particularly, SEQ ID NO.: 42 treatment is relevant in preventing the maintenance of long-lasting pain syndromes, e.g., chronic post-operative pain.

Example 8: Materials and Methods

Cell Culture and Biological Reagents

HL60 (human peripheral blood, acute promyelocytic leukemia) and PC12 (rat adrenal gland, pheochromocytomal cells) cell lines were purchased from the UCSF Cell culture facility (CA, USA). HL-60 cells were grown in RPMI media 1640+L-Glutamine (Invitrogen, CA, USA) supplemented with 10% heat-inactivated fetal bovine serum and 1% penicillin-streptomycin (Invitrogen, CA, USA). Cells were splits into 6-well plates (BD Biosciences, USA) at about $200 \times 10^4$ cells/well 24 h before treatment with 1 µM 1,25-Dihydroxyvitamin D3 with or without decoy transfection as described previously. PC12 cells were grown in DMEM containing 1,000 mg/L D-glucose, L-glutamine, 25 mM HEPES buffer, and 110 mg/L sodium pyruvate (Invitrogen, CA, USA) and supplemented with 10% heat-inactivated fetal bovine serum, 5% heat-inactivated horse serum and 1% penicillin-streptomycin (Invitrogen, CA, USA). PC12 cells were split into CellBind 6-well plates (Corning, USA) 24 h before treatment with 100 nM NGF (Invitrogen, CA, USA) and 5 µM forskolin (Sigma-Aldrich, MO, USA) with or without decoy transfection. All cells were grown at 37° C. with 5% CO2. Dead cells counting were realized using Tryptan blue (Invitrogen, CA, USA) exclusion technique on a Malassez counting chamber.

Decoy Sequences Annealing

Forward and reverse strands for each decoy sequence were synthesized by Integrated DNA Technology (IA, USA) and resuspended in either 1×TE buffer, pH 7.4 or pH 8. Each strand pair was annealed in presence of 50 mM NaCl with a 7 min 95° C. denaturation step and a slow cooling to 25° C. at 0.5° C./min. Annealing success was checked on a 2.5% agarose gel with ethidium bromide by observing the slower migration speeds of the duplexes versus a corresponding single strand.

Decoy Sequences Transfection

Transfections of decoy sequences were realized using Oligofectamine (Invitrogen, CA, USA) according to the manufacturer protocol. For HL60 experiments, decoy sequences transfections (250 nM, 500 nM, 1000 nM and 2000 nM) were immediately followed by 1,25-Dihydroxyvitamin D3 (1 µM) treatment. Cells were collected 48 h later and prepared for RNA extraction. For PC12 cells, NGF (100 ng/ml) and forskolin (5 µM) were applied immediately after decoy sequences transfections (500 nM). Cells were collected 24 h after for RNA extraction.

For both cell lines, transfection yield was measured using SEQ ID NO.: 40 coupled to fluorescein (Integrated DNA Technology, IA, USA) 24 h post-transfection. The yield of transfection was calculated based upon the counting of fluorescent versus non-fluorescent cells observed under a fluorescent microscope.

Semi-Quantitative Reverse Transcription and Polymerase Chain Reactions (sqRT-PCR)

Total RNA was extracted from cells using the RNeasy Plus kit (Qiagen, USA) that ensures removal of genomic DNA during RNA extraction. Equivalent RNA quantities are reverse transcribed into cDNA per condition, using either the First-strand cDNA synthesis kit (GE healthcare, NJ, USA) or the Superscript $1^{st}$ strand system (Invitrogen, CA, USA) and one-sixteenth of each RT was used per PCR reaction. PCR were realized in 20 µL total using the Promega master mix (Promega, WI, USA) with the following cycles: 95° C. 1 min, 55° C. 1 min, 72° C. 1 min (25 cycles for housekeeping genes ACTB and Gapdh, 35 cycles for other genes for material detection in the linear detection range and before signal saturation). All primers used (see Table 3) have been previously described.

TABLE 3

| Primer | Sequence 5'-3' | SEQ ID NO. |
| --- | --- | --- |
| hACTB S | AAGAGAGGCATCCTCACCCT | SEQ ID NO.: 54 |
| hACTB AS | TACATGGCTGGGGTGTTGAA | SEQ ID NO.: 55 |
| hBCL2 S | GGAAGTGAACATTTCGGTGAC | SEQ ID NO.: 56 |
| hBCL2 AS | GCCTCTCCTCACGTTCCC | SEQ ID NO.: 57 |
| hCDK5R1 S | GCCGTACAGAACAGCAAGAA | SEQ ID NO.: 58 |
| hCDK5R1 AS | GTCGGCATTTATCTGCAGCA | SEQ ID NO.: 59 |
| rBdkrb2 S | GAACATCTTTGTCCTCAGC | SEQ ID NO.: 60 |
| rBdkrb2 AS | CCGTCTGGACCTCCTTGAAC | SEQ ID NO.: 61 |
| rBdnf S | GGCTTTGATGAGACCGGGTTCCCT | SEQ ID NO.: 62 |
| rBdnf AS | GTAGGCCAAGTTGCCTTGTCCGT | SEQ ID NO.: 63 |
| rCacna1b S | ATGCTGTTCTTCATCTACGC | SEQ ID NO.: 64 |
| rCacna1b AS | TTGTCCATGATCACAGCAAC | SEQ ID NO.: 65 |
| rEgr1 S | AGATGATGCTGCTGAGCAAC | SEQ ID NO.: 66 |
| rEgr1 AS | AGTAAATGGGACTGCTGTCG | SEQ ID NO.: 67 |
| rGapdh S | CCGCTGATGCCCCCATGTTTGTGAT | SEQ ID NO.: 68 |
| rGapdh AS | GGCATGTCAGATCCACAACGGATAC | SEQ ID NO.: 69 |
| rGch1 S | CCACGCCATGCAGTTCTTCACCA | SEQ ID NO.: 70 |
| rGch1 AS | AGGCTGCAAGGCTTCTGTGATGGC | SEQ ID NO.: 71 |
| rGrm5 S | GTGGCGGAGGCAGAGGAGAGC | SEQ ID NO.: 72 |
| rGrm5 AS | GTGGCCGCGGTGGACAACAT | SEQ ID NO.: 73 |
| rHtr3a S | AATCAGGGCGAGTGGGAGC | SEQ ID NO.: 74 |
| rHtr3a AS | GAGGACAGCTCTTGCAAGAGGC | SEQ ID NO.: 75 |
| rNos1 S | GAATACCAGCCTGATCCATGGAAC | SEQ ID NO.: 76 |
| rNos1 AS | TCCTCCAGGAGGGTGTCCACCGCA | SEQ ID NO.: 77 |
| rP2rx3 S | TGGCGTTCTGGGTATTAAGATCGG | SEQ ID NO.: 78 |
| rP2rx3 AS | CAGTGGCCTGGTCACTGGCGA | SEQ ID NO.: 79 |
| rCdk5r1 S | GCTCTGCAGGGATGTTATCTCC | SEQ ID NO.: 80 |
| rCdk5r1 AS | CTTCTTGTCCTCCTGACCACTC | SEQ ID NO.: 81 |

TABLE 3-continued

| Primer | Sequence 5'-3' | SEQ ID NO. |
|---|---|---|
| rPnmt S | CAGACTTCTTGGAGGTCAACCTG | SEQ ID NO.: 82 |
| rPnmt AS | TTATTAGGTGCCACTTCGGGTG | SEQ ID NO.: 83 |
| rScn9a S | TTCATGACCTTGAGCAACCC | SEQ ID NO.: 84 |
| rScn9a AS | TCTCTTCGAGTTCCTTCCTG | SEQ ID NO.: 85 |

S = sense,
AS = anti-sense,
h = human,
r = rat.

12.5 µl of each PCR reaction was detected on 1% agarose gel (Invitrogen, CA, USA) with ethidium bromide (Fisher Scientific, PA, USA). Gel bands images were captured with a FluorChem SP gel imager system (Alpha Innotech, CA, USA) and analyzed using the Image J software (NIH, MD, USA). Expression levels were normalized on ACTB levels for HL60 experiments and Gapdh levels for PC12 experiments. Statistical significance was measured with the two-tails student t-test. Dose-responses curves were fitted with the exponential decay equation.

Transcription Factor ELISA Experiments

The affinity and specificity of decoy sequences for their transcription factor targets was measured with colorimetric transcription factor ELISA (Enzyme linked immuno adsorbent) kits (Panomics, CA, USA). Briefly, designated decoy sequences coupled to biotin were incubated for 30 minutes with nuclear protein extracts from TPA-stimulated K-562 cells expressing targeted transcription factors (Activemotif, CA, USA). The mixes of proteins and decoy sequences were loaded on 96-well plates coated with streptavidin provided in the kit. The quantity of transcription factor captured by each decoy sequence was revealed according to the supplier protocol using specific primary antibodies and secondary antibodies coupled to the horseradish peroxidase (HRP) enzyme. Reactions optical densities (ODs) were read at 450 nM with a Thermomax microplate reader (Molecular Device, CA, USA).

Experiments were conducted in 50 µl with 6.4 pmoles of biotin-coupled decoy sequence (probe) mixed with 10 µg of nuclear protein extract in the kit binding buffer. When the probe is incubated alone with the protein extracts, the resulting OD represents the binding activity of the probe for its target. When increasing concentration of competing, not biotinylated versions of the probe are added to the binding reaction, a reduction of OD values demonstrates binding specificity. The use of sequence variants as competitors allows measuring their relative affinities for the targeted factor as compared to the probe. The use of primary antibodies against several transcription factors (CREB/ATF, WT1, NFATC1 from Santa Cruz Biotechnology, CA, USA, SP1 from emd biosciences, WI, USA and EGR1 from Panomics, CA, USA) allows detecting the relative specificity of decoy sequences for multiple factors. Competition curves were fitted with the exponential decay equation.

Behavioural Experiments

The plantar surface of left hind paw of Sprague-Dawley Rats (male, 250-300 g) was injected (30G needle) with 150 µl of Complete Freund Adjuvant (CFA). Von Frey filaments of 1 g and 6 g were used to test for mechanical responsiveness (i.e., allodynia) of the hind paw. Briefly, each Von Frey filament was applied 5 times and the number of paw withdrawals was counted. Animals were habituated on a mesh floor 1 hour prior to testing. Basal mechanical sensitivity of animals was tested before SEQ ID NO.: 42 and CFA treatments. All experiments were conducted blinded.

SEQ ID NO.: 42 was synthesized and HPLC-purified by Integrated DNA Technology (IA, USA). Decoy duplexes were annealed as described previously, in TE pH 8 at a 2 mM final concentration and injected intrathecally in rats with 13 nmoles/injection (20 µl total, diluted 1:3, TE pH 8). The injection/testing schedule was as follows:

day 0: basal Von Frey sensitivity testing followed by SEQ ID NO.: 42 injection 1
    day 1: SEQ ID NO.: 42 injection 2, 1 h prior to CFA treatment
    day 2: SEQ ID NO.: 42 injection 3, 1 h prior to Von Frey testing
    day 5: SEQ ID NO.: 42 injection 4, 1 h prior to Von Frey testing Control animals are injected with only TE as a vehicle following the same schedule. For intrathecal injections, rats were anesthetized with 2% Isoflurane, their backs shaved and prepared with Betadine. Rats were then was placed on a bottle to keep the back arched. A 17G 1/2 needle was slid rostrally along left side of L6 transverse process till it reached L5. The needle was then inserted between L5 and L6 until the intrathecal space was reached as indicated by tail twitch.

It will be apparent to those skilled in the art that many modifications, both to materials and methods, may be practiced without departing from the scope of this disclosure. Accordingly, the present embodiments are to be considered as illustrative and not restrictive, and the invention is not to be limited to the details given herein, but may be modified within the scope and equivalents of the appended claims.

All publications and patents cited herein are incorporated by reference in their entirety.

What is claimed:

1. An oligonucleotide decoy, comprising a sequence that is at least 85% identical with SEQ ID NO:33, and comprising a KLF7 transcription factor binding site.

2. The oligonucleotide decoy of claim 1, comprising a sequence that is at least 90% identical with SEQ ID NO:33.

3. The oligonucleotide decoy of claim 2, comprising a sequence that is at least 95% identical with SEQ ID NO:33.

4. The oligonucleotide decoy of claim 3, comprising SEQ ID NO:33.

5. The oligonucleotide decoy of claim 1, which is less than 65 base pairs in length.

6. The oligonucleotide decoy of claim 5, which is less than 50 base pairs in length.

7. The oligonucleotide decoy of claim 6, which is less than 45 base pairs in length.

8. The oligonucleotide decoy of claim 1, further comprising a second transcription factor binding site, wherein said second transcription factor binding site binds to a transcription factor selected from the group consisting of POU1F1, POU2F, POU3F, POU5F1, USF, EGR1, CREB/ATF, AP1, CEBP, SRF, ETS1, MEF2, SP1, RUNX, NFAT, ELK1, ternary complex factors, STAT, GATA1, ELF1, nuclear factor-granulocyte/macrophage a, POU4F1, HNF1, ZFHX3, IRF, TEAD1, TBP, NFY, caccc-box binding factors, KLF4, KLF7, IKZF, MAF, REST, HSF, KCNIP3 and PPAR transcription factors.

9. The oligonucleotide decoy of claim 8, further comprising a third transcription factor binding site, wherein said third transcription factor binding site binds to a transcription factor selected from the group consisting of POU1F1, POU2F, POU3F, POU5F1, USF, EGR1, CREB/ATF, AP1, CEBP, SRF, ETS1, MEF2, SP1, RUNX, NFAT, ELK1, ternary complex factors, STAT, GATA1, ELF1, nuclear factor-granulocyte/macrophage a, POU4F1, HNF1, ZFHX3, IRF, TEAD1, TBP, NFY, caccc-box binding factors, KLF4, KLF5, KLF7, IKZF, MAF, REST, HSF, KCNIP3 and PPAR transcription factors.

10. A pharmaceutical composition comprising an oligonucleotide decoy of claim 1 and a pharmaceutically acceptable carrier.

11. A kit comprising an oligonucleotide decoy of claim 1 and, optionally, an instruction for using said oligonucleotide decoy.

* * * * *

SEQUENCE LISTING

```
<160> NUMBER OF SEQ ID NOS: 131

<210> SEQ ID NO 1
<211> LENGTH: 31
<212> TYPE: DNA
<213> ORGANISM: Artificial Sequence
<220> FEATURE:
<223> OTHER INFORMATION: Oligonucleotide decoy

<400> SEQUENCE: 1
ggcttatgca aattcgaatg caaatttgtc g                                    31
```

```
<210> SEQ ID NO 2
<211> LENGTH: 36
<212> TYPE: DNA
<213> ORGANISM: Artificial Sequence
<220> FEATURE:
<223> OTHER INFORMATION: Oligonucleotide decoy

<400> SEQUENCE: 2
ctaagcccac gtgaccattg gccaggtgac cagatc                              36

<210> SEQ ID NO 3
<211> LENGTH: 34
<212> TYPE: DNA
<213> ORGANISM: Artificial Sequence
<220> FEATURE:
<223> OTHER INFORMATION: Oligonucleotide decoy

<400> SEQUENCE: 3
gttatgcgtg ggcgataatg cggggcgtt atag                                34

<210> SEQ ID NO 4
<211> LENGTH: 29
<212> TYPE: DNA
<213> ORGANISM: Artificial Sequence
<220> FEATURE:
<223> OTHER INFORMATION: Oligonucleotide decoy

<400> SEQUENCE: 4
gcctccctga gctcattgac gtatctcgg                                     29

<210> SEQ ID NO 5
<211> LENGTH: 30
<212> TYPE: DNA
<213> ORGANISM: Artificial Sequence
<220> FEATURE:
<223> OTHER INFORMATION: Oligonucleotide decoy

<400> SEQUENCE: 5
cgaatatgac tgagaatgac tcagatttgc                                    30

<210> SEQ ID NO 6
<211> LENGTH: 37
<212> TYPE: DNA
<213> ORGANISM: Artificial Sequence
<220> FEATURE:
<223> OTHER INFORMATION: Oligonucleotide decoy

<400> SEQUENCE: 6
ggttctatga ttttggaatc ggattgtgca aagaagc                            37

<210> SEQ ID NO 7
<211> LENGTH: 34
<212> TYPE: DNA
<213> ORGANISM: Artificial Sequence
<220> FEATURE:
<223> OTHER INFORMATION: Oligonucleotide decoy

<400> SEQUENCE: 7
gcttcaggat gtccatatta ggagatcttg ttcg                               34

<210> SEQ ID NO 8
<211> LENGTH: 34
<212> TYPE: DNA
<213> ORGANISM: Artificial Sequence
<220> FEATURE:
<223> OTHER INFORMATION: Oligonucleotide decoy
```

```
<400> SEQUENCE: 8
ggccacagga tgtaggatgt ccatattagg atgc                           34

<210> SEQ ID NO 9
<211> LENGTH: 35
<212> TYPE: DNA
<213> ORGANISM: Artificial Sequence
<220> FEATURE:
<223> OTHER INFORMATION: Oligonucleotide decoy

<400> SEQUENCE: 9
gttctctaaa aataaaaggc taaaaataaa agtcg                          35

<210> SEQ ID NO 10
<211> LENGTH: 30
<212> TYPE: DNA
<213> ORGANISM: Artificial Sequence
<220> FEATURE:
<223> OTHER INFORMATION: Oligonucleotide decoy

<400> SEQUENCE: 10 attagggggcg gggtccgggg cggggtatta                               30

<210> SEQ ID NO 11
<211> LENGTH: 35
<212> TYPE: DNA
<213> ORGANISM: Artificial Sequence
<220> FEATURE:
<223> OTHER INFORMATION: Oligonucleotide decoy

<400> SEQUENCE: 11
gttatggcgg ggcggggcgg ggccgggcgg tttac                          35

<210> SEQ ID NO 12
<211> LENGTH: 29
<212> TYPE: DNA
<213> ORGANISM: Artificial Sequence
<220> FEATURE:
<223> OTHER INFORMATION: Oligonucleotide decoy

<400> SEQUENCE: 12
ggcaatgtgg ttttagtgtg gttttacgg                                 29

<210> SEQ ID NO 13
<211> LENGTH: 36
<212> TYPE: DNA
<213> ORGANISM: Artificial Sequence
<220> FEATURE:
<223> OTHER INFORMATION: Oligonucleotide decoy

<400> SEQUENCE: 13
gccgtttggg gtcatagaac cacaggaacc acacgg                         36

<210> SEQ ID NO 14
<211> LENGTH: 32
<212> TYPE: DNA
<213> ORGANISM: Artificial Sequence
<220> FEATURE:
<223> OTHER INFORMATION: Oligonucleotide decoy

<400> SEQUENCE: 14
cattgcccgg aaatggaccg gatgtaattt cc                             32

<210> SEQ ID NO 15
<211> LENGTH: 40
```

<210> SEQ ID NO 15
<211> LENGTH: 40
<212> TYPE: DNA
<213> ORGANISM: Artificial Sequence
<220> FEATURE:
<223> OTHER INFORMATION: Oligonucleotide decoy

<400> SEQUENCE: 15
gttcttggaa aataaatgga aaatagtgga aaataagtcg                                40

<210> SEQ ID NO 16
<211> LENGTH: 33
<212> TYPE: DNA
<213> ORGANISM: Artificial Sequence
<220> FEATURE:
<223> OTHER INFORMATION: Oligonucleotide decoy

<400> SEQUENCE: 16
cgttcccact tcctgcgacc acttcctgcc ggg                                       33

<210> SEQ ID NO 17
<211> LENGTH: 33
<212> TYPE: DNA
<213> ORGANISM: Artificial Sequence
<220> FEATURE:
<223> OTHER INFORMATION: Oligonucleotide decoy

<400> SEQUENCE: 17
ctgcacctat aaatggccta taatggggga tgc                                       33

<210> SEQ ID NO 18
<211> LENGTH: 33
<212> TYPE: DNA
<213> ORGANISM: Artificial Sequence
<220> FEATURE:
<223> OTHER INFORMATION: Oligonucleotide decoy

<400> SEQUENCE: 18
gcttatttcg cggaaggttt cccggaagtg gcg                                       33

<210> SEQ ID NO 19
<211> LENGTH: 31
<212> TYPE: DNA
<213> ORGANISM: Artificial Sequence
<220> FEATURE:
<223> OTHER INFORMATION: Oligonucleotide decoy

<400> SEQUENCE: 19
gctgtgcctt atctctttgg gataactggc g                                         31

<210> SEQ ID NO 20
<211> LENGTH: 32
<212> TYPE: DNA
<213> ORGANISM: Artificial Sequence
<220> FEATURE:
<223> OTHER INFORMATION: Oligonucleotide decoy

<400> SEQUENCE: 20
gcttaatgaa taagaggaaa aatgcatgct gg                                        32

<210> SEQ ID NO 21
<211> LENGTH: 33
<212> TYPE: DNA
<213> ORGANISM: Artificial Sequence
<220> FEATURE:
<223> OTHER INFORMATION: Oligonucleotide decoy

<400> SEQUENCE: 21
gttctgagat tgcacgatga gatttcacag tcg                                    33

<210> SEQ ID NO 22
<211> LENGTH: 32
<212> TYPE: DNA
<213> ORGANISM: Artificial Sequence
<220> FEATURE:
<223> OTHER INFORMATION: Oligonucleotide decoy

<400> SEQUENCE: 22
gtcccgcata aataatggca tccttaatcg cg                                     32

<210> SEQ ID NO 23
<211> LENGTH: 36
<212> TYPE: DNA
<213> ORGANISM: Artificial Sequence
<220> FEATURE:
<223> OTHER INFORMATION: Oligonucleotide decoy

<400> SEQUENCE: 23
gtgcaggcaa gagtagagac aggcaagagt agatgc                                 36

<210> SEQ ID NO 24
<211> LENGTH: 25
<212> TYPE: DNA
<213> ORGANISM: Artificial Sequence
<220> FEATURE:
<223> OTHER INFORMATION: Oligonucleotide decoy

<400> SEQUENCE: 24
ccgccaataa ttaattatta aggcc                                             25

<210> SEQ ID NO 25
<211> LENGTH: 35
<212> TYPE: DNA
<213> ORGANISM: Artificial Sequence
<220> FEATURE:
<223> OTHER INFORMATION: Oligonucleotide decoy

<400> SEQUENCE: 25
gcttcgttcc atttccggtc tcggtttccc cattc                                  35

<210> SEQ ID NO 26
<211> LENGTH: 34
<212> TYPE: DNA
<213> ORGANISM: Artificial Sequence
<220> FEATURE:
<223> OTHER INFORMATION: Oligonucleotide decoy

<400> SEQUENCE: 26
gctgctgtgg aatatcgacc tgtggaatat cgtg                                   34

<210> SEQ ID NO 27
<211> LENGTH: 37
<212> TYPE: DNA
<213> ORGANISM: Artificial Sequence
<220> FEATURE:
<223> OTHER INFORMATION: Oligonucleotide decoy

<400> SEQUENCE: 27
gccgtataaa tgtgctataa aagttttaag accgtgc                                37

<210> SEQ ID NO 28
<211> LENGTH: 29
<212> TYPE: DNA
<213> ORGANISM: Artificial Sequence

```
<220> FEATURE:
<223> OTHER INFORMATION: Oligonucleotide decoy

<400> SEQUENCE: 28
gccgtataaa tgtgctataa aagccgtgc                                    29

<210> SEQ ID NO 29
<211> LENGTH: 26
<212> TYPE: DNA
<213> ORGANISM: Artificial Sequence
<220> FEATURE:
<223> OTHER INFORMATION: Oligonucleotide decoy

<400> SEQUENCE: 29
atgctgcgct tttctccaat ctgcgg                                       26

<210> SEQ ID NO 30
<211> LENGTH: 40
<212> TYPE: DNA
<213> ORGANISM: Artificial Sequence
<220> FEATURE:
<223> OTHER INFORMATION: Oligonucleotide decoy

<400> SEQUENCE: 30
cgttctccga ttggtcacgg actctccgat tggtcacggc                        40

<210> SEQ ID NO 31
<211> LENGTH: 28
<212> TYPE: DNA
<213> ORGANISM: Artificial Sequence
<220> FEATURE:
<223> OTHER INFORMATION: Oligonucleotide decoy

<400> SEQUENCE: 31
gcgcacccca gcctggctca cccacgcg                                     28

<210> SEQ ID NO 32
<211> LENGTH: 37
<212> TYPE: DNA
<213> ORGANISM: Artificial Sequence
<220> FEATURE:
<223> OTHER INFORMATION: Oligonucleotide decoy

<400> SEQUENCE: 32
gatcctttgc ctccttcgat cctttgcctc cttcaag                           37

<210> SEQ ID NO 33
<211> LENGTH: 29
<212> TYPE: DNA
<213> ORGANISM: Artificial Sequence
<220> FEATURE:
<223> OTHER INFORMATION: Oligonucleotide decoy

<400> SEQUENCE: 33
ggtgtttggg agagctttgg gaggatacg                                    29

<210> SEQ ID NO 34
<211> LENGTH: 36
<212> TYPE: DNA
<213> ORGANISM: Artificial Sequence
<220> FEATURE:
<223> OTHER INFORMATION: Oligonucleotide decoy

<400> SEQUENCE: 34
gctaatcact cagcatttcg gtgagggaag tgaaag                            36
```

<210> SEQ ID NO 35
<211> LENGTH: 51
<212> TYPE: DNA
<213> ORGANISM: Artificial Sequence
<220> FEATURE:
<223> OTHER INFORMATION: Oligonucleotide decoy

<400> SEQUENCE: 35
cctttcagca ccacggacag cgccagcttc agcaccacgg acagcgcctc g       51

<210> SEQ ID NO 36
<211> LENGTH: 36
<212> TYPE: DNA
<213> ORGANISM: Artificial Sequence
<220> FEATURE:
<223> OTHER INFORMATION: Oligonucleotide decoy

<400> SEQUENCE: 36
ggatcgaaca tggagtcagt gagaaatcag gatcgg                         36

<210> SEQ ID NO 37
<211> LENGTH: 35
<212> TYPE: DNA
<213> ORGANISM: Artificial Sequence
<220> FEATURE:
<223> OTHER INFORMATION: Oligonucleotide decoy

<400> SEQUENCE: 37
ggatcgaagc cggagtcaag gaggcccctg atcgg                          35

<210> SEQ ID NO 38
<211> LENGTH: 39
<212> TYPE: DNA
<213> ORGANISM: Artificial Sequence
<220> FEATURE:
<223> OTHER INFORMATION: Oligonucleotide decoy

<400> SEQUENCE: 38
ccgaaaggac aaaggtcaag tcgaaaggac aaaggtcag                      39

<210> SEQ ID NO 39
<211> LENGTH: 35
<212> TYPE: DNA
<213> ORGANISM: Artificial Sequence
<220> FEATURE:
<223> OTHER INFORMATION: Oligonucleotide decoy

<400> SEQUENCE: 39
cgggagaaaa ttcgggaacg ttcaagaatt gtcgg                          35

<210> SEQ ID NO 40
<211> LENGTH: 34
<212> TYPE: DNA
<213> ORGANISM: Artificial Sequence
<220> FEATURE:
<223> OTHER INFORMATION: Oligonucleotide decoy

<400> SEQUENCE: 40
gttatgcgtg ggcgtagatg cggggcgtt atag                            34

<210> SEQ ID NO 41
<211> LENGTH: 16
<212> TYPE: DNA
<213> ORGANISM: Artificial Sequence
<220> FEATURE:
<223> OTHER INFORMATION: Oligonucleotide decoy

```
<400> SEQUENCE: 41
gatgcgtggg cgtagg                                                16

<210> SEQ ID NO 42
<211> LENGTH: 23
<212> TYPE: DNA
<213> ORGANISM: Artificial Sequence
<220> FEATURE:
<223> OTHER INFORMATION: Oligonucleotide decoy

<400> SEQUENCE: 42
gtatgcgtgg gcggtgggcg tag                                        23

<210> SEQ ID NO 43
<211> LENGTH: 30
<212> TYPE: DNA
<213> ORGANISM: Artificial Sequence
<220> FEATURE:
<223> OTHER INFORMATION: Oligonucleotide decoy

<400> SEQUENCE: 43
gttatgcgtt tgtagatgct ttcgttatag                                 30

<210> SEQ ID NO 44
<211> LENGTH: 20
<212> TYPE: DNA
<213> ORGANISM: Artificial Sequence
<220> FEATURE:
<223> OTHER INFORMATION: Oligonucleotide decoy

<400> SEQUENCE: 44
gttatgcgtg ggcgatatag                                            20

<210> SEQ ID NO 45
<211> LENGTH: 28
<212> TYPE: DNA
<213> ORGANISM: Artificial Sequence
<220> FEATURE:
<223> OTHER INFORMATION: Oligonucleotide decoy

<400> SEQUENCE: 45
gatgcgtggg cgttgacgtg gaaaatgc                                   28

<210> SEQ ID NO 46
<211> LENGTH: 30
<212> TYPE: DNA
<213> ORGANISM: Artificial Sequence
<220> FEATURE:
<223> OTHER INFORMATION: Oligonucleotide decoy

<400> SEQUENCE: 46
ctatttcgaa acgatctaca ttggcataac                                 30

<210> SEQ ID NO 47
<211> LENGTH: 22
<212> TYPE: DNA
<213> ORGANISM: Artificial Sequence
<220> FEATURE:
<223> OTHER INFORMATION: Oligonucleotide decoy

<400> SEQUENCE: 47
cgttcccact tcctgcgacc gg                                         22

<210> SEQ ID NO 48
```

```
<211> LENGTH: 26
<212> TYPE: DNA
<213> ORGANISM: Artificial Sequence
<220> FEATURE:
<223> OTHER INFORMATION: Oligonucleotide decoy

<400> SEQUENCE: 48
gggtgaaggc aagagtagag cggcgg                                          26

<210> SEQ ID NO 49
<211> LENGTH: 21
<212> TYPE: DNA
<213> ORGANISM: Artificial Sequence
<220> FEATURE:
<223> OTHER INFORMATION: Oligonucleotide decoy

<400> SEQUENCE: 49
cgttctccga ttggtcacgc g                                               21

<210> SEQ ID NO 50
<211> LENGTH: 26
<212> TYPE: DNA
<213> ORGANISM: Artificial Sequence
<220> FEATURE:
<223> OTHER INFORMATION: Oligonucleotide decoy

<400> SEQUENCE: 50
gtactccctt tgcctccttc aaccgg                                          26

<210> SEQ ID NO 51
<211> LENGTH: 31
<212> TYPE: DNA
<213> ORGANISM: Artificial Sequence
<220> FEATURE:
<223> OTHER INFORMATION: Oligonucleotide decoy

<400> SEQUENCE: 51
ccttattcag caccacggac agcgccattc g                                    31

<210> SEQ ID NO 52
<211> LENGTH: 23
<212> TYPE: DNA
<213> ORGANISM: Artificial Sequence
<220> FEATURE:
<223> OTHER INFORMATION: Oligonucleotide decoy

<400> SEQUENCE: 52
gcgaaaggac aaaggtcagg cgg                                             23

<210> SEQ ID NO 53
<211> LENGTH: 25
<212> TYPE: DNA
<213> ORGANISM: Artificial Sequence
<220> FEATURE:
<223> OTHER INFORMATION: Oligonucleotide decoy

<400> SEQUENCE: 53
ggcttgctgt ggaatatcga tggtg                                           25

<210> SEQ ID NO 54
<211> LENGTH: 20
<212> TYPE: DNA
<213> ORGANISM: Artificial Sequence
<220> FEATURE:
<223> OTHER INFORMATION: PCR primer

<400> SEQUENCE: 54
```
aagagaggca tcctcaccct                                               20

<210> SEQ ID NO 55
<211> LENGTH: 20
<212> TYPE: DNA
<213> ORGANISM: Artificial Sequence
<220> FEATURE:
<223> OTHER INFORMATION: PCR primer

<400> SEQUENCE: 55
tacatggctg gggtgttgaa                                               20

<210> SEQ ID NO 56
<211> LENGTH: 21
<212> TYPE: DNA
<213> ORGANISM: Artificial Sequence
<220> FEATURE:
<223> OTHER INFORMATION: PCR primer

<400> SEQUENCE: 56
ggaagtgaac atttcggtga c                                             21

<210> SEQ ID NO 57
<211> LENGTH: 18
<212> TYPE: DNA
<213> ORGANISM: Artificial Sequence
<220> FEATURE:
<223> OTHER INFORMATION: PCR primer

<400> SEQUENCE: 57
gcctctcctc acgttccc                                                 18

<210> SEQ ID NO 58
<211> LENGTH: 20
<212> TYPE: DNA
<213> ORGANISM: Artificial Sequence
<220> FEATURE:
<223> OTHER INFORMATION: PCR primer

<400> SEQUENCE: 58
gccgtacaga acagcaagaa                                               20

<210> SEQ ID NO 59
<211> LENGTH: 20
<212> TYPE: DNA
<213> ORGANISM: Artificial Sequence
<220> FEATURE:
<223> OTHER INFORMATION: PCR primer

<400> SEQUENCE: 59
gtcggcattt atctgcagca                                               20

<210> SEQ ID NO 60
<211> LENGTH: 19
<212> TYPE: DNA
<213> ORGANISM: Artificial Sequence
<220> FEATURE:
<223> OTHER INFORMATION: PCR primer

<400> SEQUENCE: 60
gaacatcttt gtcctcagc                                                19

<210> SEQ ID NO 61
<211> LENGTH: 20
<212> TYPE: DNA

```
<213> ORGANISM: Artificial Sequence
<220> FEATURE:
<223> OTHER INFORMATION: PCR primer

<400> SEQUENCE: 61
ccgtctggac ctccttgaac                                              20

<210> SEQ ID NO 62
<211> LENGTH: 24
<212> TYPE: DNA
<213> ORGANISM: Artificial Sequence
<220> FEATURE:
<223> OTHER INFORMATION: PCR primer

<400> SEQUENCE: 62
ggctttgatg agaccgggtt ccct                                         24

<210> SEQ ID NO 63
<211> LENGTH: 23
<212> TYPE: DNA
<213> ORGANISM: Artificial Sequence
<220> FEATURE:
<223> OTHER INFORMATION: PCR primer

<400> SEQUENCE: 63
gtaggccaag ttgccttgtc cgt                                          23

<210> SEQ ID NO 64
<211> LENGTH: 20
<212> TYPE: DNA
<213> ORGANISM: Artificial Sequence
<220> FEATURE:
<223> OTHER INFORMATION: PCR primer

<400> SEQUENCE: 64
atgctgttct tcatctacgc                                              20

<210> SEQ ID NO 65
<211> LENGTH: 20
<212> TYPE: DNA
<213> ORGANISM: Artificial Sequence
<220> FEATURE:
<223> OTHER INFORMATION: PCR primer

<400> SEQUENCE: 65
ttgtccatga tcacagcaac                                              20

<210> SEQ ID NO 66
<211> LENGTH: 20
<212> TYPE: DNA
<213> ORGANISM: Artificial Sequence
<220> FEATURE:
<223> OTHER INFORMATION: PCR primer

<400> SEQUENCE: 66
agatgatgct gctgagcaac                                              20

<210> SEQ ID NO 67
<211> LENGTH: 20
<212> TYPE: DNA
<213> ORGANISM: Artificial Sequence
<220> FEATURE:
<223> OTHER INFORMATION: PCR primer

<400> SEQUENCE: 67
agtaaatggg actgctgtcg                                              20
```

<210> SEQ ID NO 68
<211> LENGTH: 25
<212> TYPE: DNA
<213> ORGANISM: Artificial Sequence
<220> FEATURE:
<223> OTHER INFORMATION: PCR primer

<400> SEQUENCE: 68
ccgctgatgc ccccatgttt gtgat                                   25

<210> SEQ ID NO 69
<211> LENGTH: 25
<212> TYPE: DNA
<213> ORGANISM: Artificial Sequence
<220> FEATURE:
<223> OTHER INFORMATION: PCR primer

<400> SEQUENCE: 69
ggcatgtcag atccacaacg gatac                                   25

<210> SEQ ID NO 70
<211> LENGTH: 23
<212> TYPE: DNA
<213> ORGANISM: Artificial Sequence
<220> FEATURE:
<223> OTHER INFORMATION: PCR primer

<400> SEQUENCE: 70
ccacgccatg cagttcttca cca                                     23

<210> SEQ ID NO 71
<211> LENGTH: 24
<212> TYPE: DNA
<213> ORGANISM: Artificial Sequence
<220> FEATURE:
<223> OTHER INFORMATION: PCR primer

<400> SEQUENCE: 71
aggctgcaag gcttctgtga tggc                                    24

<210> SEQ ID NO 72
<211> LENGTH: 21
<212> TYPE: DNA
<213> ORGANISM: Artificial Sequence
<220> FEATURE:
<223> OTHER INFORMATION: PCR primer

<400> SEQUENCE: 72
gtggcggagg cagaggagag c                                       21

<210> SEQ ID NO 73
<211> LENGTH: 20
<212> TYPE: DNA
<213> ORGANISM: Artificial Sequence
<220> FEATURE:
<223> OTHER INFORMATION: PCR primer

<400> SEQUENCE: 73
gtggccgcgg tggacaacat                                         20

<210> SEQ ID NO 74
<211> LENGTH: 19
<212> TYPE: DNA
<213> ORGANISM: Artificial Sequence
<220> FEATURE:

<223> OTHER INFORMATION: PCR primer

<400> SEQUENCE: 74
aatcagggcg agtgggagc                                                    19

<210> SEQ ID NO 75
<211> LENGTH: 22
<212> TYPE: DNA
<213> ORGANISM: Artificial Sequence
<220> FEATURE:
<223> OTHER INFORMATION: PCR primer

<400> SEQUENCE: 75
gaggacagct cttgcaagag gc                                                22

<210> SEQ ID NO 76
<211> LENGTH: 24
<212> TYPE: DNA
<213> ORGANISM: Artificial Sequence
<220> FEATURE:
<223> OTHER INFORMATION: PCR primer

<400> SEQUENCE: 76
gaataccagc ctgatccatg gaac                                              24

<210> SEQ ID NO 77
<211> LENGTH: 24
<212> TYPE: DNA
<213> ORGANISM: Artificial Sequence
<220> FEATURE:
<223> OTHER INFORMATION: PCR primer

<400> SEQUENCE: 77
tcctccagga gggtgtccac cgca                                              24

<210> SEQ ID NO 78
<211> LENGTH: 24
<212> TYPE: DNA
<213> ORGANISM: Artificial Sequence
<220> FEATURE:
<223> OTHER INFORMATION: PCR primer

<400> SEQUENCE: 78
tggcgttctg ggtattaaga tcgg                                              24

<210> SEQ ID NO 79
<211> LENGTH: 21
<212> TYPE: DNA
<213> ORGANISM: Artificial Sequence
<220> FEATURE:
<223> OTHER INFORMATION: PCR primer

<400> SEQUENCE: 79
cagtggcctg gtcactggcg a                                                 21

<210> SEQ ID NO 80
<211> LENGTH: 22
<212> TYPE: DNA
<213> ORGANISM: Artificial Sequence
<220> FEATURE:
<223> OTHER INFORMATION: PCR primer

<400> SEQUENCE: 80
gctctgcagg gatgttatct cc                                                22

-continued

```
<210> SEQ ID NO 81
<211> LENGTH: 22
<212> TYPE: DNA
<213> ORGANISM: Artificial Sequence
<220> FEATURE:
<223> OTHER INFORMATION: PCR primer

<400> SEQUENCE: 81
cttcttgtcc tcctgaccac tc                                              22

<210> SEQ ID NO 82
<211> LENGTH: 23
<212> TYPE: DNA
<213> ORGANISM: Artificial Sequence
<220> FEATURE:
<223> OTHER INFORMATION: PCR primer

<400> SEQUENCE: 82
cagacttctt ggaggtcaac ctg                                             23

<210> SEQ ID NO 83
<211> LENGTH: 22
<212> TYPE: DNA
<213> ORGANISM: Artificial Sequence
<220> FEATURE:
<223> OTHER INFORMATION: PCR primer

<400> SEQUENCE: 83
ttattaggtg ccacttcggg tg                                              22

<210> SEQ ID NO 84
<211> LENGTH: 20
<212> TYPE: DNA
<213> ORGANISM: Artificial Sequence
<220> FEATURE:
<223> OTHER INFORMATION: PCR primer

<400> SEQUENCE: 84
ttcatgacct tgagcaaccc                                                 20

<210> SEQ ID NO 85
<211> LENGTH: 20
<212> TYPE: DNA
<213> ORGANISM: Artificial Sequence
<220> FEATURE:
<223> OTHER INFORMATION: PCR primer

<400> SEQUENCE: 85
tctcttcgag ttccttcctg                                                 20

<210> SEQ ID NO 86
<211> LENGTH: 31
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(17)
<223> OTHER INFORMATION: n is a, c, g, or t
<220> FEATURE:
```

```
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(30)
<223> OTHER INFORMATION: n is a, c, g, or t

<400> SEQUENCE: 86
snnnnatdbn ddnnnnnatd bnhhnnnnnn s                              31

<210> SEQ ID NO 87
<211> LENGTH: 36
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (30)..(35)
<223> OTHER INFORMATION: n is a, c, g, or t

<400> SEQUENCE: 87
snnnnnycvy rngnncvydb gycvyrbgrn nnnnns                         36

<210> SEQ ID NO 88
<211> LENGTH: 34
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (14)..(16)
<223> OTHER INFORMATION: n is a, c, g, or t
<220> FEATURE:
<221> NAME/KEY: misc_feature
<222> LOCATION: (29)..(33)
<223> OTHER INFORMATION: n is a, c, g, or t

<400> SEQUENCE: 88
snnwwgsgkr ggmnnnwwwg sgkrggmdnn nnns                           34

<210> SEQ ID NO 89
<211> LENGTH: 29
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(7)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
```

```
<220> FEATURE:
<221> NAME/KEY: misc_feature
<222> LOCATION: (24)..(28)
<223> OTHER INFORMATION: n is a, c, g, or t

<400> SEQUENCE: 89
snnnnnntka ssbmnntkas sbmnnnnns                                              29

<210> SEQ ID NO 90
<211> LENGTH: 30
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (26)..(28)
<223> OTHER INFORMATION: n is a, c, g, or t

<400> SEQUENCE: 90
ssnnnntgas knhrrrtgas knhrrnnnss                                             30

<210> SEQ ID NO 91
<211> LENGTH: 37
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(5)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (34)..(36)
<223> OTHER INFORMATION: n is a, c, g, or t

<400> SEQUENCE: 91 snnnnwwga ttktssaaks ngattktcsa aksnnns                                      37

<210> SEQ ID NO 92
<211> LENGTH: 34
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(6)
<223> OTHER INFORMATION: n is a, c, g, or t
<220> FEATURE:
<221> NAME/KEY: misc_feature
<222> LOCATION: (27)..(30)
<223> OTHER INFORMATION: n is a, c, g, or t

<400> SEQUENCE: 92
```
snnnnnggat rtccatatta ggagatnnnn wwss         34

<210> SEQ ID NO 93
<211> LENGTH: 34
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(5)
<223> OTHER INFORMATION: n is a, c, g, or t
<220> FEATURE:
<221> NAME/KEY: misc_feature
<222> LOCATION: (30)..(33)
<223> OTHER INFORMATION: n is a, c, g, or t

<400> SEQUENCE: 93
snnnncagga dddddddddt ccatattagn nnns         34

<210> SEQ ID NO 94
<211> LENGTH: 35
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(5)
<223> OTHER INFORMATION: n is a, c, g, or t
<220> FEATURE:
<221> NAME/KEY: misc_feature
<222> LOCATION: (16)..(19)
<223> OTHER INFORMATION: n is a, c, g, or t
<220> FEATURE:
<221> NAME/KEY: misc_feature
<222> LOCATION: (32)..(34)
<223> OTHER INFORMATION: n is a, c, g, or t

<400> SEQUENCE: 94
snnnnctawa mwtaannnnc tawaaataaa annns         35

<210> SEQ ID NO 95
<211> LENGTH: 30
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (14)..(16)
<223> OTHER INFORMATION: n is a, c, g, or t
<220> FEATURE:
<221> NAME/KEY: misc_feature
<222> LOCATION: (25)..(30)
<223> OTHER INFORMATION: n is a, c, g, or t

<400> SEQUENCE: 95
nnnnrrgscs krrnnnrrgs ckrrnnnnnn         30

<210> SEQ ID NO 96
<211> LENGTH: 35
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature

```
<222> LOCATION: (1)..(5)
<223> OTHER INFORMATION: n is a, c, g, or t

<400> SEQUENCE: 96
nnnnnggcgg ggsssssssss ssscgggcgg tttac                                35

<210> SEQ ID NO 97
<211> LENGTH: 29
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(5)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t

<400> SEQUENCE: 97
snnnnwgygg tddddgwgyg gtddddnns                                        29

<210> SEQ ID NO 98
<211> LENGTH: 36
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(5)
<223> OTHER INFORMATION: n is a, c, g, or t
<220> FEATURE:
<221> NAME/KEY: misc_feature
<222> LOCATION: (17)..(20)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 98
snnnnttggg gtcatannnn cacaggaacc acanns                                36

<210> SEQ ID NO 99
<211> LENGTH: 32
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(6)
<223> OTHER INFORMATION: n is a, c, g, or t
<220> FEATURE:
<221> NAME/KEY: misc_feature
<222> LOCATION: (15)..(17)
<223> OTHER INFORMATION: n is a, c, g, or t
<220> FEATURE:
<221> NAME/KEY: misc_feature
<222> LOCATION: (26)..(31)
<223> OTHER INFORMATION: n is a, c, g, or t

<400> SEQUENCE: 99
snnnnnchgg ahrynnnccg gahrynnnnn ns                                    32

<210> SEQ ID NO 100
<211> LENGTH: 40
<212> TYPE: DNA
```

```
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (34)..(39)
<223> OTHER INFORMATION: n is a, c, g, or t

<400> SEQUENCE: 100
snnmwwggaa aanndwwgga aaanndwgga aaannnnnns                     40

<210> SEQ ID NO 101
<211> LENGTH: 33
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(6)
<223> OTHER INFORMATION: n is a, c, g, or t
<220> FEATURE:
<221> NAME/KEY: misc_feature
<222> LOCATION: (17)..(19)
<223> OTHER INFORMATION: n is a, c, g, or t
<220> FEATURE:
<221> NAME/KEY: misc_feature
<222> LOCATION: (30)..(32)
<223> OTHER INFORMATION: n is a, c, g, or t

<400> SEQUENCE: 101
snnnnncact tccyvmnnny vcttcctgcn nns                            33

<210> SEQ ID NO 102
<211> LENGTH: 33
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(6)
<223> OTHER INFORMATION: n is a, c, g, or t

<400> SEQUENCE: 102
snnnnnctat aaatggccta taaatgggggg ggs                           33

<210> SEQ ID NO 103
<211> LENGTH: 33
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(7)
<223> OTHER INFORMATION: n is a, c, g, or t
<220> FEATURE:
<221> NAME/KEY: misc_feature
<222> LOCATION: (28)..(32)
<223> OTHER INFORMATION: n is a, c, g, or t
```

<400> SEQUENCE: 103
snnnnnnwwc gcggwwggww wccggwwnnn nns                33

<210> SEQ ID NO 104
<211> LENGTH: 31
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(4)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (27)..(30)
<223> OTHER INFORMATION: n is a, c, g, or t

<400> SEQUENCE: 104
snnntgcctt atctctnngg gataasnnnn s                  31

<210> SEQ ID NO 105
<211> LENGTH: 32
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(6)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t

<400> SEQUENCE: 105
snnnnntgaa twwgaggaaa awwgcatgcn ns                 32

<210> SEQ ID NO 106
<211> LENGTH: 33
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(5)
<223> OTHER INFORMATION: n is a, c, g, or t
<220> FEATURE:
<221> NAME/KEY: misc_feature
<222> LOCATION: (16)..(18)
<223> OTHER INFORMATION: n is a, c, g, or t
<220> FEATURE:
<221> NAME/KEY: misc_feature
<222> LOCATION: (29)..(32)
<223> OTHER INFORMATION: n is a, c, g, or t

<400> SEQUENCE: 106
snnnngagat tkcacnnnga gattkcacnn nns                33

<210> SEQ ID NO 107
<211> LENGTH: 32
<212> TYPE: DNA
<213> ORGANISM: Artificial Sequence
<220> FEATURE:

```
<223> OTHER INFORMATION: Oligonucleotide decoy
<220> FEATURE:
<221> NAME/KEY: misc_feature
<222> LOCATION: (2)..(5)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (29)..(31)
<223> OTHER INFORMATION: n is a, c, g, or t

<400> SEQUENCE: 107
snnnnkcmtw awtrmwnrmw kcmtwawtnn ns                               32

<210> SEQ ID NO 108
<211> LENGTH: 36
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(4)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 108
snnnagkyaa dndthhhnnn hhhyaadndt wvmtgc                           36

<210> SEQ ID NO 109
<211> LENGTH: 25
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(5)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (22)..(24)
<223> OTHER INFORMATION: n is a, c, g, or t

<400> SEQUENCE: 109
snnnnaataa tnnattattw wnnns                                      25

<210> SEQ ID NO 110
<211> LENGTH: 35
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
```

<222> LOCATION: (2)..(4)
<223> OTHER INFORMATION: n is a, c, g, or t
<220> FEATURE:
<221> NAME/KEY: misc_feature
<222> LOCATION: (31)..(34)
<223> OTHER INFORMATION: n is a, c, g, or t

<400> SEQUENCE: 110
snnnsdhwms hkwwmcssdh wmshkwwmcs nnnns        35

<210> SEQ ID NO 111
<211> LENGTH: 34
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(4)
<223> OTHER INFORMATION: n is a, c, g, or t
<220> FEATURE:
<221> NAME/KEY: misc_feature
<222> LOCATION: (17)..(19)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t

<400> SEQUENCE: 111
snnnykgykg aayhbbnnny hbbkgaatat cnns         34

<210> SEQ ID NO 112
<211> LENGTH: 37
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(4)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (32)..(36)
<223> OTHER INFORMATION: n is a, c, g, or t

<400> SEQUENCE: 112
snnntataww wnndntataw wwnnwwtaad wnnnnns      37

<210> SEQ ID NO 113
<211> LENGTH: 29
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(4)
<223> OTHER INFORMATION: n is a, c, g, or t
<220> FEATURE:

```
<221> NAME/KEY: misc_feature
<222> LOCATION: (12)..(15)
<223> OTHER INFORMATION: n is a, c, g, or t
<220> FEATURE:
<221> NAME/KEY: misc_feature
<222> LOCATION: (24)..(28)
<223> OTHER INFORMATION: n is a, c, g, or t

<400> SEQUENCE: 113
snnntataaw wnnnnwwwaa wwknnnnns                                        29

<210> SEQ ID NO 114
<211> LENGTH: 26
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (23)..(25)
<223> OTHER INFORMATION: n is a, c, g, or t

<400> SEQUENCE: 114
nnnctgmkyk kytmbycaat sdnnns                                           26

<210> SEQ ID NO 115
<211> LENGTH: 40
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (20)..(22)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 115
snntctcyga ttggyyhybn nnyyhhvgat tggytcbyns                             40

<210> SEQ ID NO 116
<211> LENGTH: 28
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (25)..(27)
<223> OTHER INFORMATION: n is a, c, g, or t

<400> SEQUENCE: 116
snncacccsa ssswssswca cccannns                                         28

<210> SEQ ID NO 117
<211> LENGTH: 37
```

```
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 117
snncctwtgc ctyyyyynnn yyyyygcctc ctwsnns                            37

<210> SEQ ID NO 118
<211> LENGTH: 29
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(4)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (25)..(28)
<223> OTHER INFORMATION: n is a, c, g, or t

<400> SEQUENCE: 118 snnnwwggg wdgnnwwgg gwdgnnnns                                       29

<210> SEQ ID NO 119
<211> LENGTH: 36
<212> TYPE: DNA
<213> ORGANISM: Artificial Sequence
<220> FEATURE:
<223> OTHER INFORMATION: Oligonucleotide decoy

<400> SEQUENCE: 119
swwwwwcact cagcwwwwcg gwgwgggwwg wwwwws                             36

<210> SEQ ID NO 120
<211> LENGTH: 51
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(27)
```

```
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

<400> SEQUENCE: 120
snnwbyagya ccdnrghsag cnnhnnnwby agyaccdnrg hsagcnnhnn s            51

<210> SEQ ID NO 121
<211> LENGTH: 36
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(5)
<223> OTHER INFORMATION: n is a, c, g, or t
<220> FEATURE:
<221> NAME/KEY: misc_feature
<222> LOCATION: (17)..(20)
<223> OTHER INFORMATION: n is a, c, g, or t
<220> FEATURE:
<221> NAME/KEY: misc_feature
<222> LOCATION: (32)..(35)
<223> OTHER INFORMATION: n is a, c, g, or t

<400> SEQUENCE: 121
snnnngarma wksagknnnn garmawksag knnnns                            36

<210> SEQ ID NO 122
<211> LENGTH: 35
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(5)
<223> OTHER INFORMATION: n is a, c, g, or t
<220> FEATURE:
<221> NAME/KEY: misc_feature
<222> LOCATION: (17)..(20)
<223> OTHER INFORMATION: n is a, c, g, or t
<220> FEATURE:
<221> NAME/KEY: misc_feature
<222> LOCATION: (32)..(34)
<223> OTHER INFORMATION: n is a, c, g, or t

<400> SEQUENCE: 122
snnnngargc csswgwnnnn gargccsswg wnnns                             35

<210> SEQ ID NO 123
<211> LENGTH: 39
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
```

```
<222> LOCATION: (19)..(21)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t

<400> SEQUENCE: 123
scgaaaggac aaassnvvnn nsgdnnggac aaaggtcas                                    39

<210> SEQ ID NO 124
<211> LENGTH: 35
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(4)
<223> OTHER INFORMATION: n is a, c, g, or t
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: misc_feature
<222> LOCATION: (31)..(34)
<223> OTHER INFORMATION: n is a, c, g, or t

<400> SEQUENCE: 124
snnnarmrww ywmgnnarmr wwywmgaatt nnnns                                        35

<210> SEQ ID NO 125
<211> LENGTH: 22
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(6)
<223> OTHER INFORMATION: n is a, c, g, or t
<220> FEATURE:
<221> NAME/KEY: misc_feature
<222> LOCATION: (17)..(21)
<223> OTHER INFORMATION: n is a, c, g, or t

<400> SEQUENCE: 125
snnnnncact tcctgcnnnn ns                                                      22

<210> SEQ ID NO 126
<211> LENGTH: 26
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(6)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (20)..(25)
<223> OTHER INFORMATION: n is a, c, g, or t

<400> SEQUENCE: 126
snnnnnagky aadndtwvmn nnnnns                                                  26
```

```
<210> SEQ ID NO 127
<211> LENGTH: 21
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 127
snntctcyga ttggytcbyn s                                        21

<210> SEQ ID NO 128
<211> LENGTH: 26
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(6)
<223> OTHER INFORMATION: n is a, c, g, or t
<220> FEATURE:
<221> NAME/KEY: misc_feature
<222> LOCATION: (23)..(25)
<223> OTHER INFORMATION: n is a, c, g, or t

<400> SEQUENCE: 128
snnnnncctw tgcctcctws rrnnns                                   26

<210> SEQ ID NO 129
<211> LENGTH: 31
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (2)..(5)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(30)
<223> OTHER INFORMATION: n is a, c, g, or t

<400> SEQUENCE: 129
snnnnwbyag yaccdnrghs agcnnhnnnn s                             31

<210> SEQ ID NO 130
<211> LENGTH: 23
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (9)..(9)
<223> OTHER INFORMATION: n is a, c, g, or t
```

```
<220> FEATURE:
<221> NAME/KEY: misc_feature
<222> LOCATION: (19)..(22)
<223> OTHER INFORMATION: n is a, c, g, or t

<400> SEQUENCE: 130
smrmwaggnc aaaggtcann nns                                           23

<210> SEQ ID NO 131
<211> LENGTH: 25
<212> TYPE: DNA
<213> ORGANISM: Artificial Sequence
<220> FEATURE:
<223> OTHER INFORMATION: Oligonucleotide decoy
<220> FEATURE:
<221> NAME/KEY: misc_feature
<222> LOCATION: (20)..(24)
<223> OTHER INFORMATION: n is a, c, g, or t

<400> SEQUENCE: 131
sscttgykgy kgaatatcgn nnnns                                         25
```